US012576154B2

(12) United States Patent
Bassi et al.

(10) Patent No.: US 12,576,154 B2
(45) Date of Patent: Mar. 17, 2026

(54) CONJUGATES OF PSMA-BINDING MOIETIES WITH CYTOTOXIC AGENTS

(71) Applicant: PHILOCHEM AG, Otelfingen (CH)

(72) Inventors: Gabriele Bassi, Otelfingen (CH); Samuele Cazzamalli, Otelfingen (CH); Tony Georgiev, Otelfingen (CH); Aureliano Zana, Otelfingen (CH); Dario Neri, Otelfingen (CH)

(73) Assignee: PHILOCHEM AG, Otelfingen (CH)

( * ) Notice: Subject to any disclaimer, the term of this patent is extended or adjusted under 35 U.S.C. 154(b) by 0 days.

(21) Appl. No.: 18/992,944

(22) PCT Filed: Jul. 31, 2023

(86) PCT No.: PCT/EP2023/071140
§ 371 (c)(1),
(2) Date: Jan. 9, 2025

(87) PCT Pub. No.: WO2024/028258
PCT Pub. Date: Feb. 8, 2024

(65) Prior Publication Data

US 2025/0262307 A1 Aug. 21, 2025

(30) Foreign Application Priority Data

Aug. 1, 2022 (EP) .................................... 22188049

(51) Int. Cl.
*A61K 47/54* (2017.01)
*A61K 47/65* (2017.01)
*A61P 35/00* (2006.01)

(52) U.S. Cl.
CPC ............ *A61K 47/542* (2017.08); *A61K 47/65* (2017.08); *A61P 35/00* (2018.01)

(58) Field of Classification Search
CPC ........ A61K 47/542; A61K 47/65; A61P 35/00
See application file for complete search history.

(56) References Cited

U.S. PATENT DOCUMENTS 8,097,254 B2 1/2012 Neri et al.

FOREIGN PATENT DOCUMENTS

WO WO 99/58570 A2 11/1999
WO WO 01/62298 A2 8/2001
WO WO 03/076469 A2 9/2003
WO WO 2020/070150 A1 4/2020
WO WO-2021151984 A1 * 8/2021 ....... A61K 47/68037
WO WO 2022/108992 A1 5/2022
WO WO-2023086833 A1 * 5/2023 ......... A61K 51/0485

OTHER PUBLICATIONS

Suzawa T et al. Enhanced tumor cell selectivity of adriamycin-monoclonal antibody conjugate via a poly(ethylene glycol)-based cleavable linker. (Journal of Controlled Release 2002 79(1-3) 19, 229-242) (Year: 2002).*
Kratochwil C et al. PSMA-Targeted Radionuclide Therapy of Metastatic Castration-Resistant Prostate Cancer with 177Lu-Labeled PSMA-617. (Journal of Nuclear Medicine Aug. 2016, 57 (8) 1170-1176) (Year: 2016).*
Alam R et al. Multivalent Cyclic RGD Conjugates for Targeted Delivery of Small Interfering RNA. (Bioconjugate Chem. 2011, 22, 8, 1673-1681). (Year: 2011).*
Lichtman MA et al. A Bacterial Cause of Cancer: An Historical Essay. (The Oncologist 2017; 22(5); 542-548) (Year: 2017).*
Hanahan D et al. Hallmarks of Cancer: The Next Generation. (Cell 2011 144(5) 646-674) (Year: 2011).*
Lee KW et al. Molecular targets of phytochemicals for cancer prevention. (Nature Reviews Cancer 2011 11 211-218). (Year: 2011).*
Boinapally et al., "A prostate-specific membrane antigen (PSMA)-targeted prodrug with a favorable in vivo toxicity profile", Scientific Reports, 2021, 11:7114, 10 pages.
Edosada et al., "Selective Inhibition of Fibroblast Activation Protein Protease Based on Dipeptide Substrate Specificity", The Journal of Biological Chemistry, 2006, 281(11): 7437-7444.
Fattorusso et al., "NMR structure of the human oncofoetal fibronectin ED-B domain, a specific marker for angiogenesis", Structure, 1999, 7(4): 381-390.
Israeli et al., "Molecular Cloning of a Complementary DNA Encoding a Prostate-specific Membrane Antigen", Cancer Research, 1993, 53: 227-230.
Neri et al., "High-affinity Antigen Binding by Chelating Recombinant Antibodies (CRAbs)", J. Mol. Biol., 1995, 246: 367-373.

(Continued)

*Primary Examiner* — Karen A. Canella
*Assistant Examiner* — John J Skoko, III
(74) *Attorney, Agent, or Firm* — James S. Keddie; Bozicevic, Field & Francis LLP

(57) ABSTRACT

A conjugate of Formula I or a pharmaceutically acceptable salt thereof, wherein: PB is a PSMA binding moiety which has a molecular weight of below 1000 Da; $L^1$ is a linker covalently attaching PB to Gly-Pro, said linker being a saturated or a partially or fully unsaturated framework comprising C and H atoms and at least one heteroatom, wherein said framework has end points of attachment 'a' and 'b' and a length between 6 and 30 atoms (via the shortest path between PB and Gly-Pro) between 'a' and 'b'; wherein said framework may include one or more straight and/or branched chains and/or rings and is optionally substituted on any available C atom(s) by one or more F; $L^2$ is a either a single bond or a self-immolative linker; and Drug is a cytotoxic agent linked to Gly-Pro.

Formula I

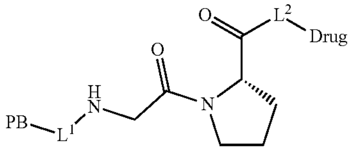

Gly-Pro

9 Claims, 8 Drawing Sheets

Specification includes a Sequence Listing.

(56) References Cited

OTHER PUBLICATIONS

Sartor et al., "Lutetium-177-PSMA-617 for Metastatic Castration-Resistant Prostate Cancer", The New English Journal of Medicine, 2021, 385: 1091-1103.
Scher et al., "Prevalence of Prostate Cancer Clinical States and Mortality in the United States: Estimates Using a Dynamic Progression Model", PLoS ONE, 2015, 10(10): e0139440, 12 pages.
Sung et al., "Global Cancer Statistics 2020: GLOBOCAN Estimates of Incidence and Mortality Worldwide for 36 Cancers in 185 Countries", CA Cancer J Clin, 2021, 71: 209-249.
Zana et al., "Abstract LB522: Fibroblast activation protein triggers the release of drug payload from non-internalizing small molecule-drug conjugates in solid tumors", Cancer Research, Jun. 15, 2022, retrieved from the Internet: URL: https://aacrjournals.org/cancerres/article/82/12_Supplement/LB522/700248/Abstract-LB522-Fibroblast-activation-protein [retrieved on Apr. 20, 2023].
Balamkundu et al., "Lysosomal-Cleavable Peptide Linkers in Antibody-Drug Conjugates", Biomedicines, Nov. 16, 2023, 11, 3080, https://doi.org/10.3390/biomedicines11113080.
Beck et al., "Strategies and challenges for the next generation of antibody-drug conjugates", Nature Reviews | Drug Discovery, May 2017, 16: 315-337.
Kostova et al., "The Chemistry Behind ADCs", Pharmaceuticals, May 7, 2021, 14, 442, https://doi.org/10.3390/ph14050442.

* cited by examiner

CONJUGATES OF PSMA-BINDING MOIETIES WITH CYTOTOXIC AGENTS

CROSS-REFERENCE TO RELATED APPLICATIONS

This application is a § 371 national phase of International Application No. PCT/EP2023/071140, filed on Jul. 31, 2023, which claims the benefit of European Patent Application No. 22188049.5, filed on Aug. 1, 2022, which applications are incorporated by reference herein.

INCORPORATION BY REFERENCE OF SEQUENCE LISTING PROVIDED AS A SEQUENCE LISTING XML FILE

A Sequence Listing is provided herewith as a Sequence Listing XML, "008443970.xml", created on Jul. 13, 2023, and having a size of 15,833 bytes. The contents of the Sequence Listing XML are incorporated herein by reference in their entirety.

FIELD OF THE INVENTION

The present invention relates to conjugates of a small-molecule Prostate-Specific Membrane Antigen (PS MA) binder with a cytotoxic agent, and their use in treating malignancies characterized by PSMA overexpression, such as prostate cancer.

BACKGROUND

Prostate cancer is the second most common cancer in men. With an estimated 375,304 deaths in 2020 worldwide, prostate cancer is the fifth leading cause of death from cancer in men and represents 6.8% of total cancer death in males (Sung 2021).

Treatment of prostate cancer with androgen deprivation therapy (ADT) such as luteinising hormone-releasing hormone (LHRH) analogues or orchidectomy is usually initially effective at controlling metastatic diseases. However, patients inevitably progress from an androgen sensitive to a castration-resistant phenotype which is associated with 90% of overall mortality (Scher 2015).

Prostate specific membrane antigen (PSMA) is a transmembrane glycoprotein associated with tumour grade and development and is over-expressed in cancerous prostate cells. PSMA represents an ideal target for the development of targeted drug conjugates due to its low expression in normal organs.

The development of targeted drugs, able to selectively localize at the site of the disease after systemic administration, is highly desirable. A strategy to generate such drugs is represented by the chemical conjugation of a therapeutic payload, like cytotoxic drugs or radionuclides, to a ligand specific for a disease marker. Disease-specific monoclonal antibodies, peptides and small molecule ligands have been considered as ligands of choice for the development of targeted drugs. The use of small ligands for targeting applications has several advantages compared to bigger molecules like peptides and antibodies: more rapid and efficient tumour penetration, lower immunogenicity and lower manufacturing costs.

Small organic ligands specific to prostate-specific membrane antigen have shown excellent biodistribution profiles in preclinical models of cancer and in patients. These ligands have been conjugated to cytotoxic drugs to generate small molecule-drug conjugate (SMDCs) and to radionuclides to enable the formation of small molecule-radio conjugate products (SMRCs) for the treatment of cancer. $^{177}$Lu[Lu]-PSMA-617 (Pluvicto™—Novartis) is a SMRC approved for the treatment of metastatic castrate-resistant prostate cancer (mCRPC) patients in the US. WO2022/108992 discloses SMDCs with a PSMA targeting moiety, and a cleavable linker which is cathepsin cleavable, comprising, for example, Val-Cit.

SUMMARY OF THE INVENTION

The first aspect of the present invention provides a conjugate of Formula I:

Formula I

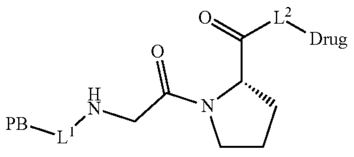

Gly-Pro or a pharmaceutically acceptable salt thereof, wherein:

PB is a PSMA binding moiety which has a molecular weight of below 1000 Da;

$L^1$ is a linker covalently attaching PB to Gly-Pro, said linker being a saturated or a partially or fully unsaturated framework comprising C and H atoms and at least one heteroatom, wherein said framework has end points of attachment 'a' and 'b' and a length between 6 and 30 atoms (via the shortest path between PB and Gly-Pro) between 'a' and 'b'; wherein said framework may include one or more straight and/or branched chains and/or rings and is optionally substituted on any available C atom(s) by one or more F;

$L^2$ is a either a single bond or a self-immolative linker; and

Drug is a cytotoxic agent linked to Gly-Pro.

In some embodiments, one of $L^1$ and $L^2$ may be branched so that there are two drugs in the conjugate.

The second aspect of the present invention provides a pharmaceutical composition comprising the conjugate of the first aspect and a pharmaceutically acceptable excipient. The second aspect of the present invention further provides the conjugate of the first aspect or said pharmaceutical composition for use in a method for treatment of the human or animal body.

The third aspect of the present invention provides the conjugate of the first aspect or the pharmaceutical composition of the second aspect for use in therapy or prophylaxis of an individual suffering from or at risk for malignancies characterized by PSMA overexpression. The third aspect of the present invention further provides a method for treatment or prophylaxis of malignancies characterized by PSMA overexpression comprising administering a therapeutically effective amount of said conjugate or pharmaceutical composition to a subject suffering from or having risk for said disease or disorder. The third aspect of the present invention further provides the use of a conjugate of the first aspect of the invention in the manufacture of a medicament for the treatment or prophylaxis of malignancies characterized by PSMA overexpression.

Malignancies characterized by PSMA overexpression may be prostate cancer, including metastatic prostate cancer, hormone sensitive prostate cancer (HSPC), and castration resistant prostate cancer (CRPC). In some embodiments, the metastatic prostate cancer may be metastatic hormone sensitive prostate cancer (mHSPC) or metastatic castration resistant prostate cancer (mCRPC).

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which:

FIGS. 1E and 1F show the release when the experiments were repeated in triplicate for Conjugates 1 (FIG. 1E) and 2 (FIG. 1F).

FIG. 3E shows a timepoint study of the MMAE release of Conjugate 1 in the HT1080.hPSMA tumor model (n=3).

DETAILED DESCRIPTION OF THE INVENTION

Figure 1:
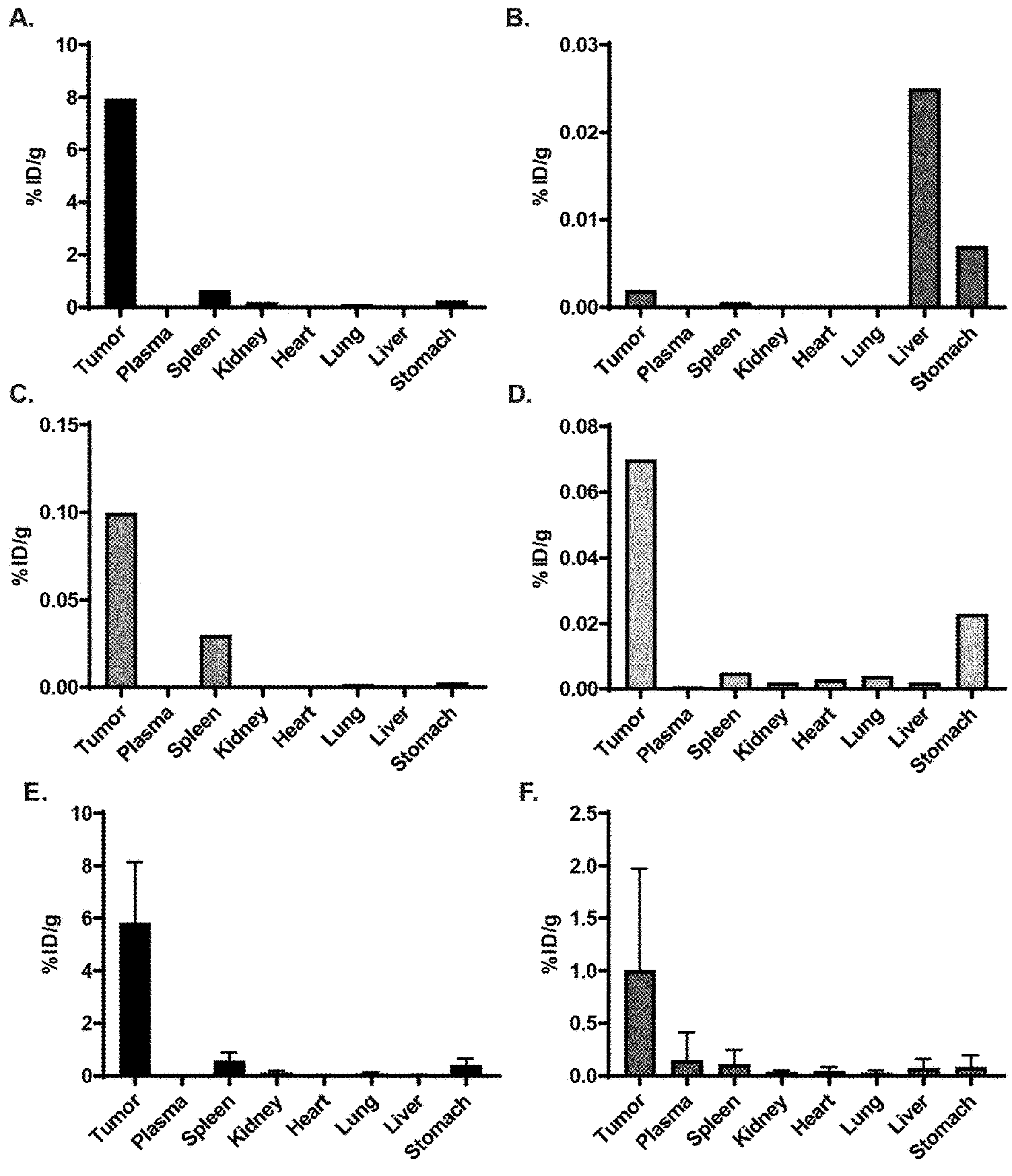
FIG. 1 shows the efficacy of in vivo drug release after systemic administration of a conjugate of the invention (Conjugate 1 (FIG. 1A)) and comparative Conjugates 2 (FIG. 1B), 3 (FIG. 1C) and 4 (FIG. 1D) in a LNCaP tumor model.

Aspects and embodiments of the present invention will now be discussed with reference to the accompanying figures. Further aspects and embodiments will be apparent to those skilled in the art. All documents mentioned in this text are incorporated herein by reference.

The present inventors have identified conjugates of a small-molecule Prostate-Specific Membrane Antigen (PSMA) binder with a cytotoxic agent. The conjugates according to the invention have a high affinity for PSMA and/or are suitable for targeted delivery of the payload (the cytotoxic agent), to a site afflicted by or at risk of disease or disorder characterized by PSMA overexpression.

The conjugates of the present invention may form a stable complex with PSMA.

The conjugates of the invention further may have an increased tumour-to-prostate uptake ratio; a more potent anti-tumour effect (e.g., measured by mean tumour volume decrease), and/or lower toxicity (e.g., as assessed by the evaluation of changes (%) in body weight). The conjugates of the invention may have a higher Therapeutic Index (e.g. Toxic Dose/Effective Dose).

The conjugates may have improved efficacy based on superior release of the cytotoxic payload in the tumor with respect to the prior art.

Conjugates of the present invention are of Formula I:

PB

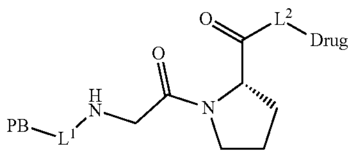

Gly-Pro

PB is a small-molecule PSMA binding moiety, wherein the moiety has a molecular weight of below 1000 Da.

Preferably, PB is the binding portion of PSMA-617, i.e. of formula II:

Formula II

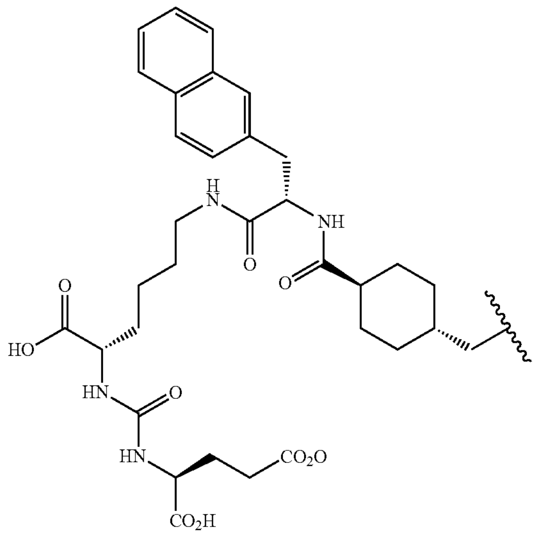

wherein the wavy bond represents a point of attachment to linker $L^1$.

PSMA-617

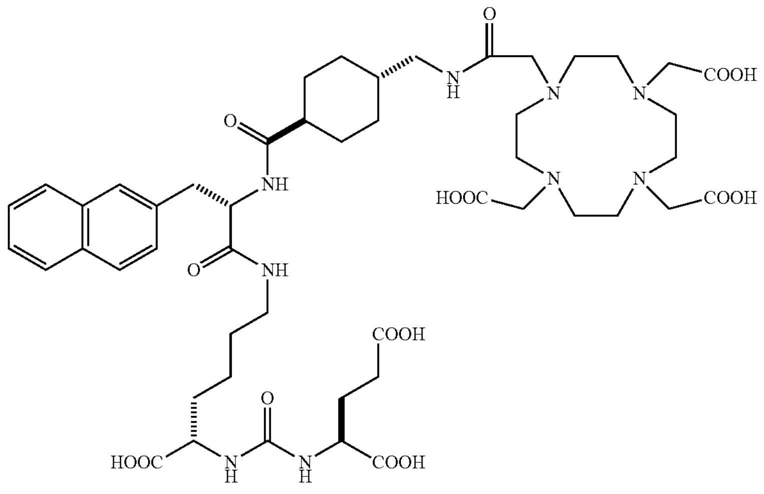

when complexing $Lu^{177}$ is used in the treatment of metastatic castration-resistant prostate cancer (Sartor 2021). The binding moiety part has been shown to effectively target PSMA, which is highly expressed on prostate cancer cells (Israeli 1993).

$L^1$

In reference to the Linker, as described herein, it is to be understood that the branching, where present, may be located on a chain (even a chain of 1 atom length) or a ring. The skilled person would generally interpret in this manner, but for the avoidance of doubt, it is to be understood that the "branching" that occurs inherently in order to form a ring is not considered as "branching" in the context of the Linker embodiments described herein. It is further to be understood that 'branches' (and definitions for branches provided herein) refer to branches that branch off the main chain/rings of atoms between 'a' and 'b', leading to a 'dead end' in the molecular structure.

$L^1$ is a linker covalently connecting PB to Gly-Pro, which is a saturated or a partially or fully unsaturated framework comprising C and H atoms and at least one heteroatom, wherein said framework has end points of attachment 'a' and 'b' and a length between 6 and 30 atoms (via the shortest path between PB and Gly-Pro) between 'a' and 'b'; wherein said framework may include one or more straight and/or branched chains and/or rings and is optionally substituted on any available C atom(s) by one or more F.

Where $L^1$ is branched so that there are two drugs in the conjugate, this means that there are two Gly-Pro-$L^2$-Drug moieties attached to PB.

In some embodiments the framework of the Linker is a saturated or partially unsaturated framework.

In some embodiments the framework of the Linker comprises C and H atoms and at least two heteroatoms. It is to be understood that "heteroatom" may represent an oxygen, nitrogen or sulphur atom unless explicitly further limited in a given context.

In some embodiments the framework of the Linker comprises C and H atoms and at least one N heteroatom.

In some embodiments the framework of the Linker comprises C and H atoms and at least two heteroatoms.

In some embodiments the framework of the Linker comprises C and H atoms and at least four heteroatoms.

In some embodiments the framework of the Linker comprises C and H atoms and at least six heteroatoms.

In some embodiments the framework of the Linker comprises C and H atoms and at least two N heteroatoms, at least two O heteroatoms and at least one S heteroatom.

In some embodiments the framework of the Linker includes from 1 to 12 heteroatoms.

In some embodiments the framework of the Linker includes from 2 to 12 heteroatoms.

In some embodiments the framework of the Linker includes from 4 to 12 heteroatoms.

In some embodiments the Linker has a minimum length from 8 to 26 atoms between 'a' and 'b'.

In some embodiments the total number of C and hetero atoms in the Linker framework is from 8 to 30.

In some embodiments the total number of C and hetero atoms in the Linker framework is from 10 to 28.

In some embodiments the framework of the Linker may include (or consist of) one or more straight and/or branched chains and/or rings (wherein the total number of branches is from 0 to 7) that are optionally substituted on any available C atom(s) by one or more F.

In some embodiments the framework of the Linker may include (or consist of) one or more straight and/or branched chains and/or rings (wherein the total number of branches is from 3 to 7) that are optionally substituted on any available C atom(s) by one or more F.

In some embodiments the framework of the Linker may include (or consist of) one or more straight and/or branched chains and/or rings (wherein the total number of branches is 5 to 7) that are optionally substituted on any available C atom(s) by one or more F.

In some embodiments the total number of branches is 6.

In some embodiments, the branches are selected from $NH_2$ and =O

In some embodiments the total number of branches is 6, 5 branches consist of =O and 1 branch consists of $NH_2$.

In some embodiments the framework of the Linker is not substituted by any F.

Where $L^1$ is branched so that there are two drugs in the conjugate, the number of branches may be double those discussed above, i.e. the total number of branches may be from 0 to 14.

In some of these embodiments the total number of branches is 12, 10 branches consist of =O and 2 branches consist of $NH_2$.

Where $L^1$ is branched so that there are two drugs in the conjugate, in some embodiments the total number of C and hetero atoms in the Linker framework is from 14 to 70.

Where $L^1$ is branched so that there are two drugs in the conjugate, in some embodiments the total number of C and hetero atoms in the Linker framework is from 30 to 64.

In some embodiments, a ring in the framework of the Linker may comprise one or two heteroatoms. In some of these embodiments, the heteroatoms in the ring are selected from N and O. In certain embodiments, the heteroatoms in the ring are N.

In some embodiments, the framework of the Linker comprises a single ring.

In some embodiments, the framework of the Linker comprises a single ring with a single N heteroatom.

In some embodiments, the framework of the Linker comprises one or more functional groups selected from:

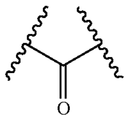
Carbonyl

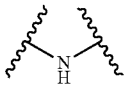
Amino

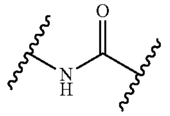
Amide

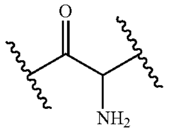
α-amino ketone

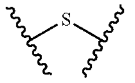
Thio

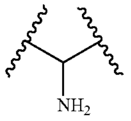
Amine

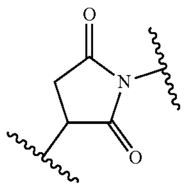
Succinimidyl

-continued

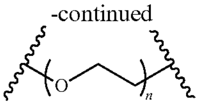
Ethylene glycol
(n = 1 to 6)

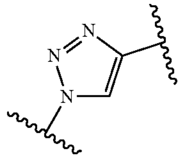
or
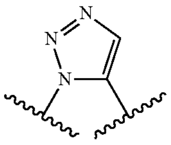
1,2,3-Triazole

In some embodiments, $L^1$ is non-cleavable by membrane-inserted fibroblast activation protein (FAP).

In some embodiments, $L^1$ is of Formula III:

$$^{PB}\text{-}(L^1\text{-}1)\text{-}(L^1\text{-}2)\text{-}(L^1\text{-}3)\text{-}* \qquad \text{Formula III}$$

wherein $^{PB}$- represents the point of attachment to moiety PB; and

-* represents the point of attachment to Gly-Pro;

wherein together the groups $L^1$-1, $L^1$-2 and $L^1$-3 form a linker framework as defined above.

In some embodiments, $L^1$-1 is of formula IV:

Formula IV

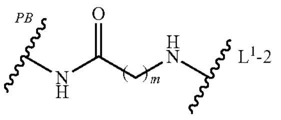

wherein m is 1 to 6.

$^{PB}$ represents the point of attachment to moiety PB; and $L^1$-2 represents the point of attachment to $L^1$-2.

In certain embodiments, m is 5.

In some embodiments, $L^1$-2 is:

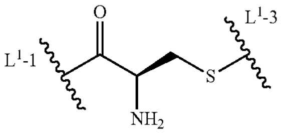 [SMILES: *SC[C@@H](N)C(*)=O]

$L^1$-1 represents the point of attachment to $L^1$-1; and $L^1$-3 represents the point of attachment to $L^1$-3.

In some embodiments, $L^1$-2 is:

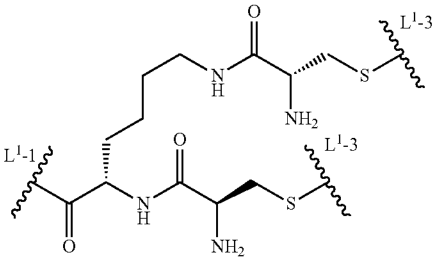 [SMILES: *SC[C@@H](N)C(=O)N[C@@H](CCCCNC(=O)[C@@H](N)CS*)C(*)=O]

$L^1$-1 represents the point of attachment to $L^1$-1; and each $L^1$-3 represents the point of attachment to each $L^1$-3.

In some embodiments, $L^1$-3 is of formula V:

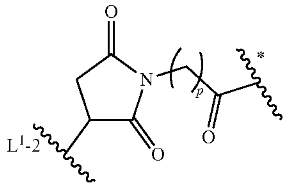

Formula V wherein p is 1 to 6.

$L^1$-2 represents the point of attachment to $L^1$-2; and

* represents the point of attachment to Gly-Pro.

In certain embodiments, p is 5.

In an embodiment, $L^1$ is $L^1$-4:

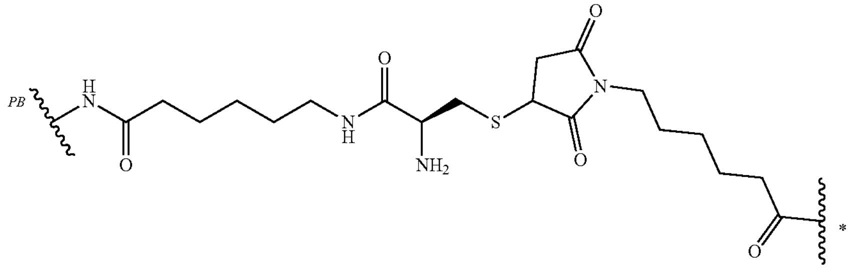

$L^1$-4

In an embodiment, $L^1$ is $L^1$-5:

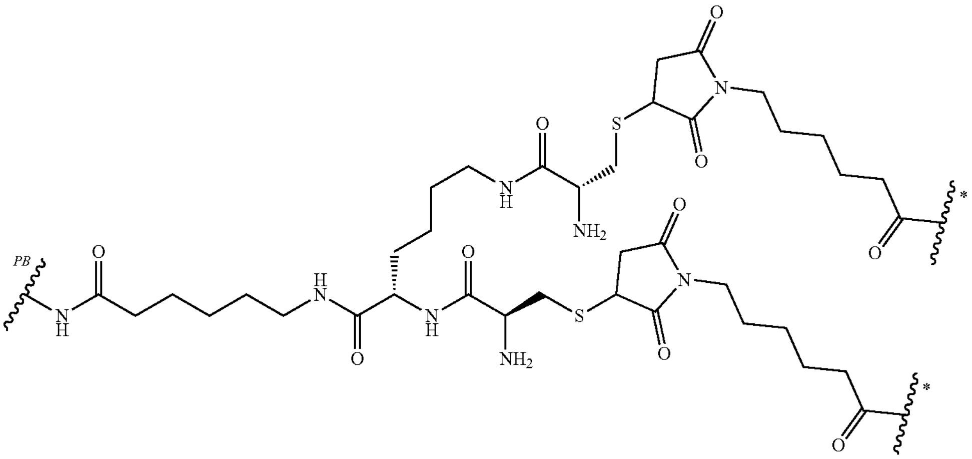

$L^1$-5

Gly-Pro

The dipeptide residue Gly-Pro is cleavable by action of membrane-inserted fibroblast activation protein (FAP), as described in Edosada 2006.

The incorporation of the Gly-Pro motif provides an efficient release of the cytotoxic agent in contrast to other motifs, such as Val-Cit or disulfide.

$L^2$ $L^2$ is a single bond or a self-immolative linker.

Self-immolative linkers are also known as electronic cascade linkers. These linkers undergo elimination and fragmentation upon enzymatic cleavage of a covalently bound peptide residue to release a covalently bound drug.

In embodiments where the self-immolative linker is present, it is coupled to PB through the enzymatically cleavable peptide sequence Gly-Pro, that provides a substrate for an enzyme to cleave the amide bond to initiate the self-immolative reaction. Suitably, Drug is connected to the self-immolative spacer via a chemically reactive functional group such as a primary or secondary amine, imine, hydroxyl, sulfhydryl, carbamate or carboxyl.

In some embodiments, the self-immolative linker is PABC (para-aminobenzyloxycarbonyl), which has the following structure:

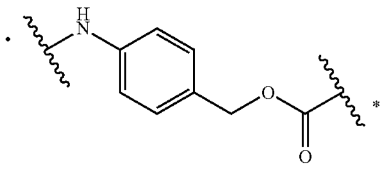 [SMILES: *Nc1ccc(COC(*)=O)cc1]

wherein

. represents a point of attachment to Gly-Pro; and

* represents a point of attachment to Drug.

In some embodiments, $L^2$ is branched so that there are two drugs in the conjugate.

In some embodiments, the self-immolative linker is derived from (4-amino-1,3-phenylene)dimethanol, which has the following structure:

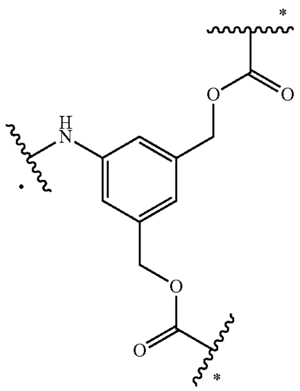 [SMILES: *Nc1cc(COC(*)=O)cc(COC(*)=O)c1]

wherein . represents a point of attachment to Gly-Pro; and each * represents a point of attachment to each Drug.

Drug

Drug is a cytotoxic agent linked to Gly-Pro.

Cytotoxic agents are compounds which can cause destruction of cells.

Drug, the cytotoxic agent, may be selected from different groups including auristatins, camptothecins, DNA minor groove binding agents, DNA minor groove alkylating agents, enediynes, lexitropsins, duocarmycins, taxanes, puromycins, dolastatins, maytansinoids and vinca alkaloids.

In some embodiments, the cytotoxic agent is a camptothecin (i.e., having a structure derived from a camptothecin compound family member) or a camptothecin derivative. Preferably, the camptothecin is derived from exatecan having the following structure:

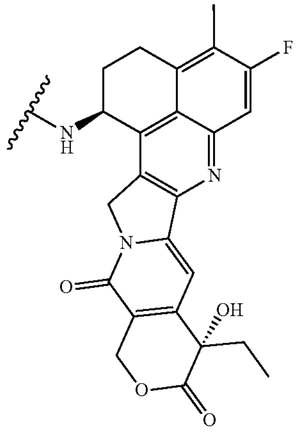

Exatecan wherein the wavy bond represents a point of attachment to linker $L^2$.

In some embodiments, the cytotoxic agent is an auristatin (i.e., having a structure derived from an auristatin compound family member) or an auristatin derivative.

In some embodiments the auristatin is of formula DI:

DI

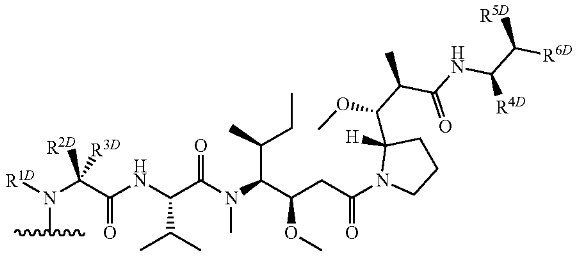

wherein:

$R^{1D}$ is H or $C_{1-6}$ alkyl; preferably H or $CH_3$;

$R^{2D}$ is $C_{1-6}$ alkyl; preferably $CH_3$ or Pr;

$R^{3D}$ is independently H or H or $C_{1-6}$ alkyl; preferably H or $CH_3$;

$R^{4D}$ is independently H, H or $C_{1-6}$ alkyl, COO(H or $C_{1-6}$ alkyl), CONH(H or $C_{1-6}$ alkyl), phenyl, naphthyl or $C_{5-10}$ heteroaryl; preferably H, $CH_3$, COOH, $COOCH_3$ or thiazolyl;

$R^{5D}$ is independently H, OH, H or $C_{1-6}$ alkyl; preferably H or OH; and $R^{6D}$ is independently phenyl, naphthyl or $C_{5-10}$ heteroaryl, which groups are optionally substituted by a group selected from $C_{1-4}$ alkyl (e.g. methyl), —COOH, —$COOCH_3$, —OH, —$OCH_3$ and halo; preferably unsubstituted phenyl or pyridyl.

$C_{1-6}$ alkyl: The term "$C_{1-6}$ alkyl" as used herein, pertains to a monovalent moiety obtained by removing a hydrogen atom from a carbon atom of a hydrocarbon compound having from 1 to 6 carbon atoms, which are saturated and may also be branched. Examples of saturated alkyl groups include, but are not limited to, methyl ($C_1$), ethyl ($C_2$), propyl ($C_3$), butyl ($C_4$), pentyl ($C_5$) and hexyl ($C_6$). Examples of saturated linear alkyl groups include, but are not limited to, methyl ($C_1$), ethyl ($C_2$), n-propyl ($C_3$), n-butyl ($C_4$), n-pentyl (amyl) ($C_5$) and n-hexyl ($C_6$).

Examples of saturated branched alkyl groups include, but are not limited to, iso-propyl ($C_3$), iso-butyl ($C_4$), sec-butyl ($C_4$), tert-butyl ($C_4$), iso-pentyl ($C_5$), neo-pentyl ($C_5$), methylpentyl ($C_6$) (e.g. 2-, 4-,), dimethylpentyl ($C_7$) (e.g. 1,3-, 1,4-, 2,3-), and methylhexyl ($C_7$) (e.g. 1-, 5-).

$C_{5-10}$ heteroaryl: The term "$C_{5-10}$ heteroaryl", as used herein, pertains to a monovalent moiety obtained by removing a hydrogen atom from an aromatic ring atom of an aromatic compound, which moiety has from 5 to 10 ring atoms of which from 1 to 4 are ring heteroatoms. For the avoidance of doubt, substituents on the heteroaryl ring may be linked via either a carbon atom or a heteroatom. Examples of heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Halo: F, Br or Cl

In some embodiments, $R^{1D}$ is H. In some embodiments, $R^{1D}$ is $CH_3$.

In some embodiments, $R^{2D}$ is methyl. In some embodiments, $R^{2D}$ is Pr.

In some embodiments, $R^{3D}$ is H. In some embodiments, $R^{3D}$ is $CH_3$.

In some embodiments, $R^{4D}$ is selected from H, $CH_3$, COOH, $COOCH_3$ and thiazolyl.

In some embodiments, $R^{5D}$ is H. In some embodiments, $R^{5D}$ is OH.

In some embodiments, $R^{6D}$ is phenyl. In some embodiments, $R^{6D}$ is pyridyl.

Preferably, the auristatin is derived from monomethyl auristatin E having the following structure:

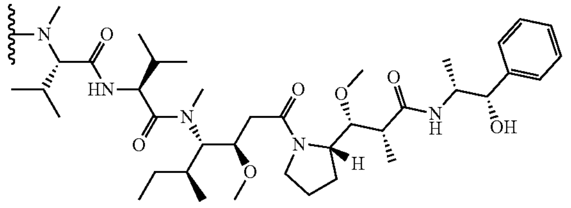

MMAE wherein the wavy bond represents a point of attachment to linker $L^2$.

In other embodiments the auristatin derived from monomethyl auristatin F having the following structure:

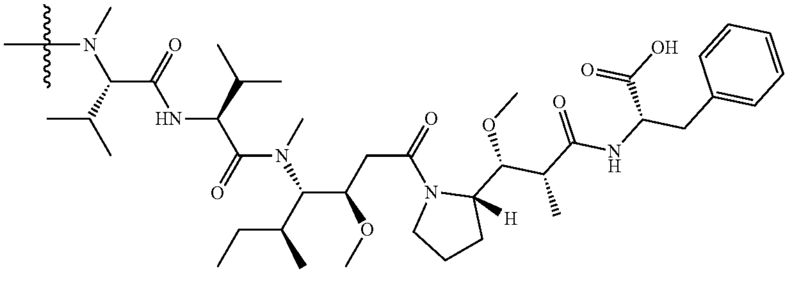

MMAF wherein the wavy bond represents a point of attachment to linker $L^2$.

In some embodiments, the Drug is linked to Gly-Pro by PABC (para-aminobenzyloxycarbonyl) as $L^2$.

In some embodiments, the Drugs are linked to Gly-Pro by a derivative of (4-amino-1,3-phenylene)dimethanol as $L^2$.

Conjugate

In some embodiments:

(a) PB is formula II; and/or (b) $L^1$ is $L^1$-4; and/or (c) $L^2$ is PABC; and/or (d) Drug is selected from Exatecan and MMAE.

In some embodiments:

(i) PB is formula II; and $L^1$ is $L^1$-4; or (ii) PB is formula II; and $L^2$ is PABC; or (iii) PB is formula II; and Drug is selected from Exatecan and MMAE; or (iv) $L^1$ is $L^1$-4; and $L^2$ is PABC; or (v) $L^1$ is $L^1$-4; and Drug is selected from Exatecan and MMAE; or (vi) $L^2$ is PABC; and Drug is selected from Exatecan and MMAE; or (vii) PB is formula II; $L^1$ is $L^1$-4; and $L^2$ is PABC; or (viii) PB is formula II; $L^1$ is $L^1$-4; and Drug is selected from Exatecan and MMAE; or (ix) PB is formula II; $L^2$ is PABC; and Drug is selected from Exatecan and MMAE; or (x) $L^1$ is $L^1$-4; and $L^2$ is PABC; and Drug is selected from Exatecan and MMAE.

In certain embodiments, PB is formula II; $L^1$ is $L^1$-4; $L^2$ is PABC; and Drug is selected from Exatecan and MMAE.

In some embodiments:

(a) PB is formula II; and/or (b) $L^1$ is $L^1$-4 or $L^1$-5; and/or (c) $L^2$ is PABC or a derivative of (4-amino-1,3-phenylene) dimethanol; and/or (d) Drug is selected from Exatecan, MMAE and MMAF.

In some embodiments:

(i) PB is formula II; and $L^1$ is $L^1$-4 or $L^1$-5; or (ii) PB is formula II; and $L^2$ is PABC or a derivative of (4-amino-1,3-phenylene)dimethanol or (iii) PB is formula II; and Drug is selected from Exatecan, MMAE and MMAF; or (iv) $L^1$ is $L^1$-4 or $L^1$-5; and $L^2$ is PABC or a derivative of (4-amino-1,3-phenylene)dimethanol; or (v) $L^1$ is $L^1$-4 or $L^1$-5; and Drug is selected from Exatecan, MMAE and MMAF; or (vi) $L^2$ is PABC or a derivative of (4-amino-1,3-phenylene)dimethanol; and Drug is selected from Exatecan, MMAE and MMAF; or (vii) PB is formula II; $L^1$ is $L^1$-4 or $L^1$-5; and $L^2$ is PABC or a derivative of (4-amino-1,3-phenylene)dimethanol; or (viii) PB is formula II; $L^1$ is $L^1$-4 or $L^1$-5; and Drug is selected from Exatecan, MMAE and MMAF or (ix) PB is formula II; $L^2$ is PABC or a derivative of (4-amino-1,3-phenylene)dimethanol; and Drug is selected from Exatecan, MMAE and MMAF; or (x) $L^1$ is $L^1$-4 or $L^1$-5; and $L^2$ is PABC or a derivative of (4-amino-1,3-phenylene)dimethanol; and Drug is selected from Exatecan, MMAE and MMAF.

In certain embodiments, PB is formula II; $L^1$ is $L^1$-4; $L^2$ is PABC; and Drug is MMAE.

In certain embodiments, PB is formula II; $L^1$ is $L^1$-4; $L^2$ is PABC; and Drug is MMAF.

In certain embodiments, PB is formula II; $L^1$ is $L^1$-5; $L^2$ is PABC; and Drug is MMAE.

In certain embodiments, PB is formula II; $L^1$ is $L^1$-5; $L^2$ is PABC; and Drug is MMAF.

In certain embodiments, PB is formula II; $L^1$ is $L^1$-4; $L^2$ is a derivative of (4-amino-1,3-phenylene)dimethanol; and Drug is MMAE.

In certain embodiments, PB is formula II; $L^1$ is $L^1$-4; $L^2$ is a derivative of (4-amino-1,3-phenylene)dimethanol; and Drug is MMAF.

Other Forms

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereoisomer" refers to a subset of stereoisomer with two or more chiral centers and whose molecules are not mirror images of one another. Diastereomers have different physico-chemical properties such as melting points, boiling points, spectral properties, and reactivities. Mixtures of diastereoisomers can be separated under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropoisomers, as well as mixtures thereof such as racemic mixtures, form part of the present invention. Many organic compounds exist in optically active forms, i.e., they can rotate the plane of polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, $—OCH_3$, is not to be construed as a reference to its structural isomer, a hydroxymethyl group, $—CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

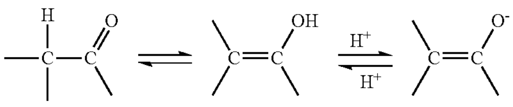

keto enol enolate

The term "tautomer" or "tautomeric form" refers to structural isomers of different energies which are interconvertible via an energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labelled compounds of the present invention, for example those into which radioactive isotopes such as $^3H$, $^{13}C$, and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}F$ labelled compound may be useful for PET or SPECT studies. Isotopically labelled compounds of this invention and prodrugs thereof can generally be prepared by carrying out the procedures disclosed in the schemes or in the examples and preparations described below by substituting a readily available isotopically labelled reagent for a non-isotopically labelled reagent. Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Treatment

The compounds described herein may be used to treat disease. The treatment may be therapeutic and/or prophylactic treatment, with the aim being to prevent, reduce or stop an undesired physiological change or disorder. The treatment may prolong survival as compared to expected survival if not receiving treatment.

The disease that is treated by the compound may be any disease that might benefit from treatment. This includes chronic and acute disorders or diseases including those pathological conditions which predispose to the disorder.

The term "cancer" and "cancerous" is used in its broadest sense as meaning the physiological condition in mammals that is typically characterized by unregulated cell growth. A tumour comprises one or more cancerous cells.

When treating cancer, the therapeutically effect that is observed may be a reduction in the number of cancer cells; a reduction in tumour size; inhibition or retardation of cancer cell infiltration into peripheral organs; inhibition of tumour growth; and/or relief of one or more of the symptoms associated with the cancer.

In animal models, efficacy may be assessed by physical measurements of the tumour during the treatment, and/or by determining partial and complete remission of the cancer. For cancer therapy, efficacy can, for example, be measured by assessing the time to disease progression (TTP) and/or determining the response rate (RR).

Disclosed are also methods for treatment of the human or animal body, the methods involving a step of administering a therapeutically effective amount of a conjugate or a pharmaceutical composition as described herein to a subject in need thereof. More specifically, herein disclosed are methods for treatment, e.g., by therapy or prophylaxis, of a subject suffering from or having risk for malignancies characterized by PSMA overexpression.

When used in the methods disclosed herein, the compound has a prolonged residence at the disease site at a therapeutically or diagnostically relevant level, preferably beyond 1 hour, more preferably beyond 6 hours post injection.

The malignancy characterized by PSMA overexpression may be prostate cancer.

In some embodiments, the prostate cancer is metastatic prostate cancer, hormone sensitive prostate cancer (HSPC) or castrate resistant prostate cancer (CRPC). In some embodiments, the metastatic prostate cancer may be metastatic hormone sensitive prostate cancer (mHSPC) or metastatic castration resistant prostate cancer (mCRPC). Metastatic prostate cancer refers to prostate cancer which has spread or metastasized to another part of the body.

Hormone sensitive prostate cancer (HSPC) refers to prostate cancer whose growth is inhibited by a decrease in androgen levels or by inhibiting androgen action.

Castration resistant prostate cancer (CRPC) refers to prostate cancer which continues to grow even when androgen levels in the body are extremely low or undetectable.

Metastatic hormone sensitive prostate cancer (mHSPC) refers to prostate cancer which has spread or metasised to another part of the body, and whose growth is inhibited by a decrease in androgen levels or by inhibiting androgen action.

Metastatic castration resistant prostate cancer (mCRPC) refers to prostate cancer which has spread or metastasized to another part of the body, and which continues to grow even when androgen levels in the body are extremely low or undetectable.

Combinations

In some embodiments, the present invention provides a method for treatment or prophylaxis of malignancies characterized by PSMA overexpression, comprising administering to the subject a first amount of a conjugate of Formula I or a pharmaceutically acceptable salt thereof, and a second amount of a therapeutic agent. In the method, the first amount and the second amount together comprise a therapeutically effective amount.

In some embodiments, the present invention provides a conjugate of Formula I or a pharmaceutically acceptable salt thereof, for use in the treatment or prophylaxis of malignancies characterized by PSMA overexpression in a subject, wherein said treatment comprises the separate, sequential or simultaneous administration of i) said conjugate of Formula I or a pharmaceutically acceptable salt thereof, and ii) a therapeutic agent, to said subject.

In some embodiments, the present invention provides the use of a conjugate of Formula I or a pharmaceutically acceptable salt thereof in the manufacture of a medicament for use in the treatment or prophylaxis of malignancies characterized by PSMA overexpression, wherein said treatment or prophylaxis comprises the separate, sequential or simultaneous administration of i) said medicament comprising said conjugate of Formula I, or a pharmaceutically acceptable salt thereof, and ii) a therapeutic agent.

In some embodiments, disclosed is a pharmaceutical product comprising i) a conjugate of Formula I or a pharmaceutically acceptable salt thereof, and ii) a therapeutic agent.

In some embodiments, disclosed is a kit comprising: a first pharmaceutical composition comprising a conjugate of Formula I, or a pharmaceutically acceptable salt thereof; a second pharmaceutical composition comprising a therapeutic agent; and instructions for using the first and second pharmaceutical compositions in combination.

In some embodiments the second therapeutic agent is an immunocytokine.

Herein, the term "immunocytokine" refers to a conjugate protein or fusion protein comprising a cytokine and an antibody, antibody fragment or antibody derivative. A fusion protein is a polypeptide that is a translation product resulting from the fusion of two or more genes or nucleic acid coding sequences into one open reading frame (ORF). The fused expression products of the two genes or ORFs may be conjugated by a linker. Herein, the terms conjugate protein or fusion protein are generally used interchangeably. The fusion protein may further comprise a signal peptide sequence, normally located upstream (5') of the specific binding member and subunit.

Immunocytokine Comprising IL2

Preferably, the immunocytokine comprises a sequence having IL2 activity, i.e., an IL2 polypeptide, i.e., the cytokine IL2 or a functional fragment thereof. Preferably, the immunocytokine comprises only one (i.e., a single) IL2 polypeptide per polypeptide chain. Herein the terms "IL2" and "IL2 polypeptide" are used interchangeably.

The IL2 may be derived from any animal, e.g. human, rodent (e.g. rat, mouse), horse, cow, pig, sheep, dog, etc. Human IL2 is preferred in conjugates for administration to humans. The amino acid sequence of human IL2 is set out in SEQ ID NO: 9. The immunocytokine conjugate preferably comprises a single IL2 polypeptide. An IL2 polypeptide in an immunocytokine of the invention retains a biological activity of IL2, e.g., an ability to promote proliferation and/or differentiation of activated T and B lymphocytes and natural killer (NK) cells, and/or to induce cytotoxic T cell (CTL) activity, and/or to induce NK/lymphokine-activated killer (LAK) cell antitumor cytotoxicity.

Antibodies, Fragments or Derivatives Thereof Comprised in the Immunocytokine

Besides a cytokine (e.g., IL2), the immunocytokine comprises an antibody or an antibody fragment or an antibody derivative. Preferably the immunocytokine herein comprises an antibody derivative. The antibody derivative may, e.g., comprise a single-chain variable fragment "scFv", a "SIP" (WO 2003/076469) or a "Crab" (Neri 1995).

Preferably the antibody derivate comprises a scFv. As is known in the art, a scFv comprises a VH domain and a VL domain, wherein the domains are linked by a linker that allows association of VH and VL domains to form an antigen binding site. The scFv may be stabilized by the incorporation of disulphide bridges linking the VH and VL domains.

Single chain Fv (scFv) antibody polypeptide sequences are particularly preferred for incorporation in the immunocytokine (e.g., with a further polypeptide sequence having IL2 activity), owing to their small size of the scFv format, which provides physiological and therapeutic advantages for in vivo use of the immunocytokine conjugates. In addition, scFv lack an Fc region, potentially reducing anti-idiotypic reactions and also minimizing undesirable properties relating to activation of complement and interaction with Fc receptors that may hinder tumour targeting and cause non-specific cell activation.

The linker joining the VH and VL domains within an scFv chain may be a peptide linker sequence that is not long enough to allow pairing of the VH and VL domains within the same scFv polypeptide chain. Thus, a homodimer of scFvs may form instead, in which the VH of one scFv chain pairs with the VL of the other scFv chain (and vice versa). This general format may be referred to as an "scFv2" format, or, alternatively, in some cases, as a "diabody". Examples of suitable short linker sequences are GSSGG (SEQ ID NO: 12) and GGSGG (SEQ ID NO: 13). Preferably the linker is such as the 12-residue linker SEQ ID NO: 11.

Antigen Binding Specificity of the Immunocytokine

The antibody, antibody fragment or antibody derivative suitably binds specifically to an extra-cellular matrix (ECM) component associated with neoplastic growth and/or angiogenesis. The antibody, fragment or derivative thereof comprises an antigen-binding site having the complementarity determining regions (CDRs), or the VH and/or VL domains of an antibody capable of specifically binding to an antigen of interest. In particular, it may comprise one or more CDRs or VH and/or VL domains of an antibody capable of specifically binding to an antigen of the ECM.

The antibody, fragment or derivative thereof may specifically bind fibronectin. Fibronectin is an antigen subject to alternative splicing, and a number of alternative isoforms of fibronectin are known, including alternatively spliced isoforms A-FN and B-FN, comprising domains ED-A or ED-B, respectively, which are known markers of angiogenesis. Preferably, the antibody, fragment or derivative thereof binds to fibronectin isoform B-FN, e.g., most preferably it binds to the ED-B domain (extra domain B) of fibronectin isoform B-FN. The amino acid sequence of the ED-B domain of B-FN is provided by residues 1266-1356 of the UniProt database entry P02751 (human Fibronectin).

Figure 4:
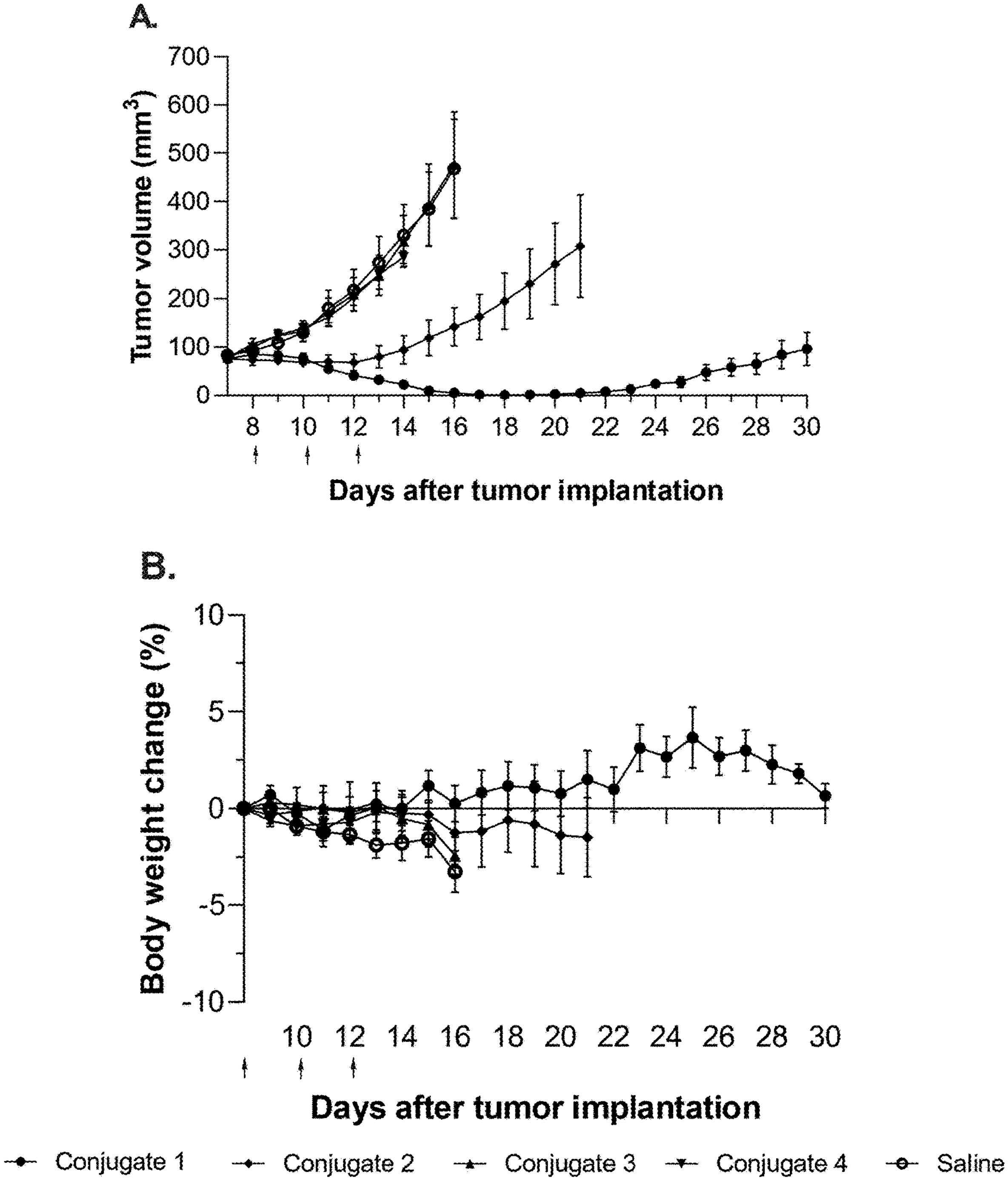
FIG. 4 shows the therapeutic efficacy of Conjugate 1 as compared to Conjugates 2, 3 and 4 in Balb/c nude mice bearing HT1080.hPSMA xenografts: Graph (A) compares the therapeutic activity of the conjugates and a saline group as negative control and Graph (B) outlines the percentage change in body weight over the course of the experiment (n=5).

Preferably, the antibody, fragment or derivative (e.g., an scFv polypeptide sequence) binds to the epitope shown in FIG. 4c of Fattorusso 1999.

Fibronectin isoform B-FN is one of the best-known markers for angiogenesis (WO 97/045544).

Also preferably, the antibody, antibody fragment or antibody derivative (e.g., scFv sequence) that specifically binds to alternatively spliced ED-B domain of fibronectin isoform B-FN comprises an antigen-binding site derived from the antibody L19. The antibody L19 binds specifically to the alternatively spliced ED-B domain of fibronectin isoform B-FN. The sequence of antibody L19 is disclosed in U.S. Pat. No. 8,097,254. An example of a most preferred antibody derivative is thus L19 scFv, which has been described previously (WO 99/058570; WO 2003/076469; see also the L19 scFv-comprising immunocytokine of SEQ ID NO:15 and FIG. 1B in WO 2020/070150).

Most preferably, the immunocytokine comprises (as the antibody derivative) a human monoclonal scFv polypeptide sequence specific for alternatively spliced ED-B domain of fibronectin isoform B-FN and (as the cytokine) IL2 (see, e.g., SEQ ID NO:15 and FIG. 1B in WO2020/070150, and SEQ ID NO:10 herein).

Antigen-Binding Site and Sequences

The antigen-binding site may, e.g., comprise one, two, three, four, five or six CDRs of antibody L19. Amino acid sequences of the CDRs of L19 are: SEQ ID NO:1 (CDR1 VH); SEQ ID NO:2 (CDR2 VH); SEQ ID NO:3 (CDR3 VH); SEQ ID NO:4 (CDR1 VL); SEQ ID NO:5 (CDR2 VL), and/or SEQ ID NO:6 (CDR3 VL).

SEQ ID NOs 1-3 are the amino acid sequences of the VH CDR regions (1-3, respectively) of the human monoclonal antibody L19. SEQ ID NOs 4-6 are the amino acid of the VL CDR regions (1-3, respectively) of the human monoclonal antibody L19.

The amino acid sequence of the VH and VL domains of antibody L19 correspond to SEQ ID NOs 7 and 8, respectively.

Preferably the antibody derivative comprises a VH domain with an amino acid sequence comprising VH CDR1, VH CDR2, and/or VH CDR3 of L19, and a VL domain with an amino acid sequence comprising VL CDR1, VL CDR2, and/or VL CDR3 of L19.

The antibody derivative as described above may comprise a VH domain having an amino acid sequence with at least 60%, 65%, 70%, 75%, 80%, 85%, 90%, 95% or 100% (preferably 80%) sequence identity with the amino acid sequence of the L19 VH domain as set out in SEQ ID NO: 7, and/or may comprise a VL domain having an amino acid sequence with at least 60%, 65%, 70%, 75%, 80%, 85%, 90%, 95% or 100% % (preferably 80%) sequence identity with the amino acid sequence of the L19 VL domain as set out in SEQ ID NO: 8.

Preferably the antibody derivative as described above is an L19 scFv (i.e., an scFv derived from and comprising one or more antigen-specific portions of antibody L19; interchangeably referred to as "scFv(L19)"). An L19 scFv may thus comprise one, two, three, four, five or six CDRs of antibody L19 (preferably all six CDRs). Optionally the L19 scFv may comprise an L19 VH domain (SEQ ID NO: 7) and/or an L19 VL domain (SEQ ID NO: 8), e.g., both the L19 VH and the L19 VL.

In an scFv unit, the VH and VL domains are joined by a linker. The linker may be a peptide linker sequence that is not long enough to allow pairing of the VH and VL domains. Thus, a homodimer of scFvs may form instead, in which the VH of one scFv chain pairs with the VL of the other scFv chain (and vice versa). This general format may be referred to as an "scFv2" format, or, alternatively, in some cases, as a "diabody". Examples of suitable short linker sequences are GSSGG (SEQ ID NO: 12) and GGSGG (SEQ ID NO: 13). Preferably the linker is the 12-residue linker SEQ ID NO: 11.

In a preferred embodiment, the antibody derivative is an scFv(L19) having an amino acid sequence with at least 60%, 65%, 70%, 75%, 80%, 85%, 90%, 95% or 100% (preferably 80%) sequence identity with the amino acid sequence of as set out in SEQ ID NO: 16.

Linkage of Segments within the Immunocytokine

The immunocytokine comprises a cytokine (e.g., an IL2 polypeptide) and is conjugated to an antibody, an antibody fragment or an antibody derivative. This conjugation may be effected through any suitable covalent bond or linker moiety, e.g., a disulphide or peptide bond, most preferably a peptide linker sequence. A peptide linker sequence may be a short (2-30, preferably 10-20) residue stretch of amino acids. Suitable examples of peptide linker sequences are known in the art. Examples of suitable linker sequences are $(G_4S)_3$ (SEQ ID NO:14) or EFSSSSGSSSSGSSSSG (SEQ ID NO: 15). One or more different linkers may be used. Preferably, the linker may be the 17-residue linker of SEQ ID NO: 15.

Thus, the antibody, antibody fragment, or antibody derivative and IL2 may be produced and/or secreted as a single-chain polypeptide.

The IL2 is preferably linked to the C-terminus of the antibody or the antibody fragment or the antibody derivative. Preferably, that linkage may be via a peptide linker sequence, as disclosed herein. Where the IL2 is conjugated to the C-terminus, the N-terminus of the antibody or the antibody fragment or the antibody derivative is preferably free. "Free" in this context refers to the N-terminus not being linked or otherwise conjugated to another moiety, such as IL2.

Preferred L19-IL2 Immunoconjugates.

Preferably, the immunocytokine comprises an L19-derived scFv unit linked to an IL2 polypeptide in a conjugate polypeptide chain that forms a homodimer due to complementary pairing between the VH and VL domains of the scFv unit in two polypeptide chains (in accordance with the scFv2 or diabody format). Thus, preferably, the immunocytokine comprises a sequence having at least 60%, 65%, 70%, 75%, 80%, 85%, 90%, 95% or 100% (preferably 80%) sequence identity with the amino acid sequence of the "L19-IL2" immunocytokine represented by SEQ ID NO: 10, which comprises an L19-derived scFv unit linked to IL2, possesses such functionality and forms a homodimer via the scFv units in this manner. More preferably, the immunocytokine comprises the sequence of SEQ ID NO: 10 (i.e., an amino acid sequence of an scFv-format L19-IL2 polypeptide).

The production and purification of L19-IL2 constructs may be performed as described in WO 01/062298.

Pharmaceutical Compositions

The conjugates described herein may be in the form of pharmaceutical compositions which may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used. There may be different composition/formulation requirements dependent on the different delivery systems. By way of example, the pharmaceutical composition may be formulated to be administered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be administered by different routes. If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration, the compositions may be administered in the form of tablets or lozenges which can be formulated in a conventional manner.

The compound of the present invention may be administered in the form of a pharmaceutically acceptable or active salt. Pharmaceutically acceptable salts are well known to those skilled in the art, and for example, include those mentioned by Berge et al, in J. Pharm. Sci., 66, 1-19 (1977). Salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The routes for administration (delivery) may include, but are not limited to, one or more of oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Typically, a physician will determine the actual dosage which will be most suitable for an individual subject. The specific dose level and frequency of dosage for each patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The formulations may be packaged in unit-dose or multi-dose containers, for example sealed ampoules and vials, and may be stored in a freeze-dried (lyophilized) condition requiring only the addition of the sterile liquid carrier, for example water, for administration. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

Chemical Synthesis

Compounds of the invention may be made as shown in the examples.

Further aspects of the invention provide a method of synthesising the conjugate of the first aspect of the invention, and intermediates in this synthesis.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps. It must be noted that, as used in the specification and the appended claims, the singular forms "," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

General Methods

Reversed-Phase High-Pressure Liquid Chromatography (HPLC)

Final products and conjugates were purified with a semi preparative reversed-phase high-pressure liquid chromatography (RP-HPLC) on an Agilent 1200 Series RP-HPLC with a PDA UV detector. The system was equipped with a Synergi 4 μm, Polar-RP 80 Å 10×150 mm C18 column using flow rate of 5 mL/min with the following gradient of eluent A (mQ millipore water 0.1% TFA) and eluent B (acetonitrile with 0.1% TFA): 0-15 min 90% to 0% A, 15-16 min 0% A, 16-17 min 0% to 90% A, 17-18 min 90% A.

Reversed-Phase Medium-Pressure Liquid Chromatography (MPLC)

Small organic molecules that could be produced at higher quantities (>10 mg) were purified by reversed-phase medium-pressure liquid chromatography (BUCHI) on a C18 40 μM irregular 12 g column using mQ millipore water 0.1% formic acid (FA) (eluent A) and acetonitrile 0.1% FA (eluent B) as mobile phase at following gradient: 0-5 min 98% A, 5-45 min 98% to 0% A, 45-50 min 0% A, 50-50.1 min 0% to 98% A and 50.1-55 min 98% A. The flow rate was set to 30 mL/min.

Analytical LC-MS

Spectra were recorded on an Agilent 6100 Series Single Quadrupole MS system combined with an Agilent 1200 Series LC, using an InfinityLab Poroshell 120 EC-C18 Column, 2.7 μm, 4.6×50 mm, at a flow rate of 0.8 mL/min, acetonitrile:water with 0.1% formic acid. The analyses were performed with the following gradient 10% to 100% acetonitrile in 5 min.

General Solid-Phase Synthesis Procedures (S1)

Solid-phase synthesis was performed with Wang resin (100-200 mesh, 1.1 mmol/g). In brief, resin was swollen for 15 min in dimethylformamide (DMF) previous to any reaction steps. Incubations were performed in 10 mL reaction columns on a rotator mixer at room temperature.

Fmoc Deprotection (S2)

Resin was incubated two times (15 min) with 20% piperidine in DMF. After deprotection, the resin was washed 5-10 times with DMF to remove residual piperidine.

Mini Cleavage for LC-MS Analysis (S3)

A small portion of resin was transferred to an Eppendorf tube and incubated with 40 μL trifluoracetic acid (TFA) for 15 min at room temperature. The cleavage was quenched by addition of 80 μL DMF to centrifuge the suspension (1 min at 10'000 rcf) previous to LC-MS analysis. This method was used to monitor the synthesis after each reaction step on resin.

Amide Coupling (S4)

The carboxylic acids, O-(7-azabenzotriazol-1-yl)-N,N,N',N'-tetramethyluronium hexafluorophosphate (HATU) and diisopropylethylamine (DIPEA) were dissolved in DMF (0.08 M) and added to the resin bound free amino group. After incubation, the resin was subsequently washed five times with DMF. Coupling efficiency was monitored by LC-MS.

Resin Cleavage and Purification (S5)

Cleavage solution was prepared as following: 95% trifluoracetic acid (TFA), 2.5% water and 2.5% triisopropylsilane (TIPS) for general products, or 50% trifluoracetic acid (TFA), 45% dichloromethane (DCM), 2.5% thioanisole and 2.5% triisopropylsilane (TIPS) for cysteine-containing products. Two consecutive cleavages (1 h at room temperature each) were performed. Cleavage fractions were combined and either directly purified via RP HPLC or precipitated in diethyl ether for subsequent purification (see below).

Peptide Precipitation (S6)

Peptides were precipitated from the cleavage solution after addition of 5-10 volumes ice-cold diethyl ether after most of the TFA was removed under reduced pressure. Precipitation proceeded for 30 min at −20° C. to obtain the peptide as pellet by centrifugation (3200 rcf, 5 min, 4° C.). The crude was dissolved in water:acetonitrile (1:1) to be purified by reversed-phase chromatography.

Coupling of Payloads to (4-Nitrophenyl) Carbonate Derivatives (GP1)

The respective (4-nitrophenyl) carbonate derivative (1.0 equiv.) and HOAt (1.0 equiv.) were weighed into an Eppendorf tube and dissolved in DMF (0.05 M). The solution was transferred to another Eppendorf tube containing the respective payload (1.2 equiv.), which was weighed in under appropriate safety conditions. DIPEA (6.0 equiv.) was added, and the mixture was incubated in a shaker incubator overnight (16-24 h) at 25° C. The reaction mixture was diluted with DMF (1:3) and was directly purified via (Agilent 1200 series system equipped with Synergi 4 μm Polar-RP 80 Å 10×150 mm C18 column using a gradient of 90:10 to 0:100 in 14 min water/ACN+0.1% TFA).

Michael Addition Between Compound 12 (Thiol) and Maleimide (Linker-Payload Derivative) (GP2)

The maleimido-containing linker-payload derivative (1 equiv.) was dissolved in DMSO (0.01 M). The solution was transferred into an Eppendorf tube, containing a mixture of compound 12 in PBS (0.01 M) to achieve a final concentration of 0.005 M. Finally, sat. aq. $NaHCO_3$ (5-20 μL) was added and the reaction was incubated in a shaker incubator at 37° C. for 1 h. The reaction mixture was diluted with DMSO (1:3) and was directly purified via (Agilent 1200 series system equipped with Synergi 4 μm Polar-RP 80 Å 10×150 mm C18 column using a gradient of 90:10 to 0:100 in 14 min water/ACN+0.1% TFA).

Disulfide Bond Formation Between Compound 12 (thiol) and 2-(pyridin-2-yldisulfanyl)ethyl Payload Derivative (GP3)

The 2-(pyridin-2-yldisulfanyl)ethyl payload derivative (1 equiv.) was dissolved in DMSO (0.01 M). The solution was transferred into an Eppendorf tube, containing a mixture of compound 12 in 20 mM sodium phosphate buffer (pH=7, 0.01 M) to achieve a final concentration of 0.005 M. The reaction was incubated in a shaker incubator at 37° C. for 1 h. The mixture was diluted with DMSO (1:3) and was directly purified via (Agilent 1200 series system equipped with Synergi 4 μm Polar-RP 80 Å 10×150 mm C18 column using a gradient of 90:10 to 0:100 in 14 min water/ACN+0.1% TFA).

Synthesis of Intermediates

Synthesis of Compounds 11 and 12

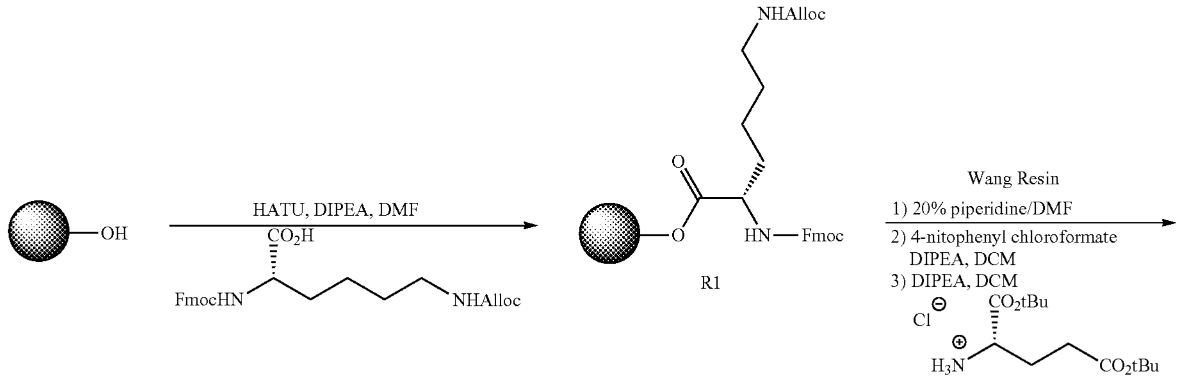

R1

-continued
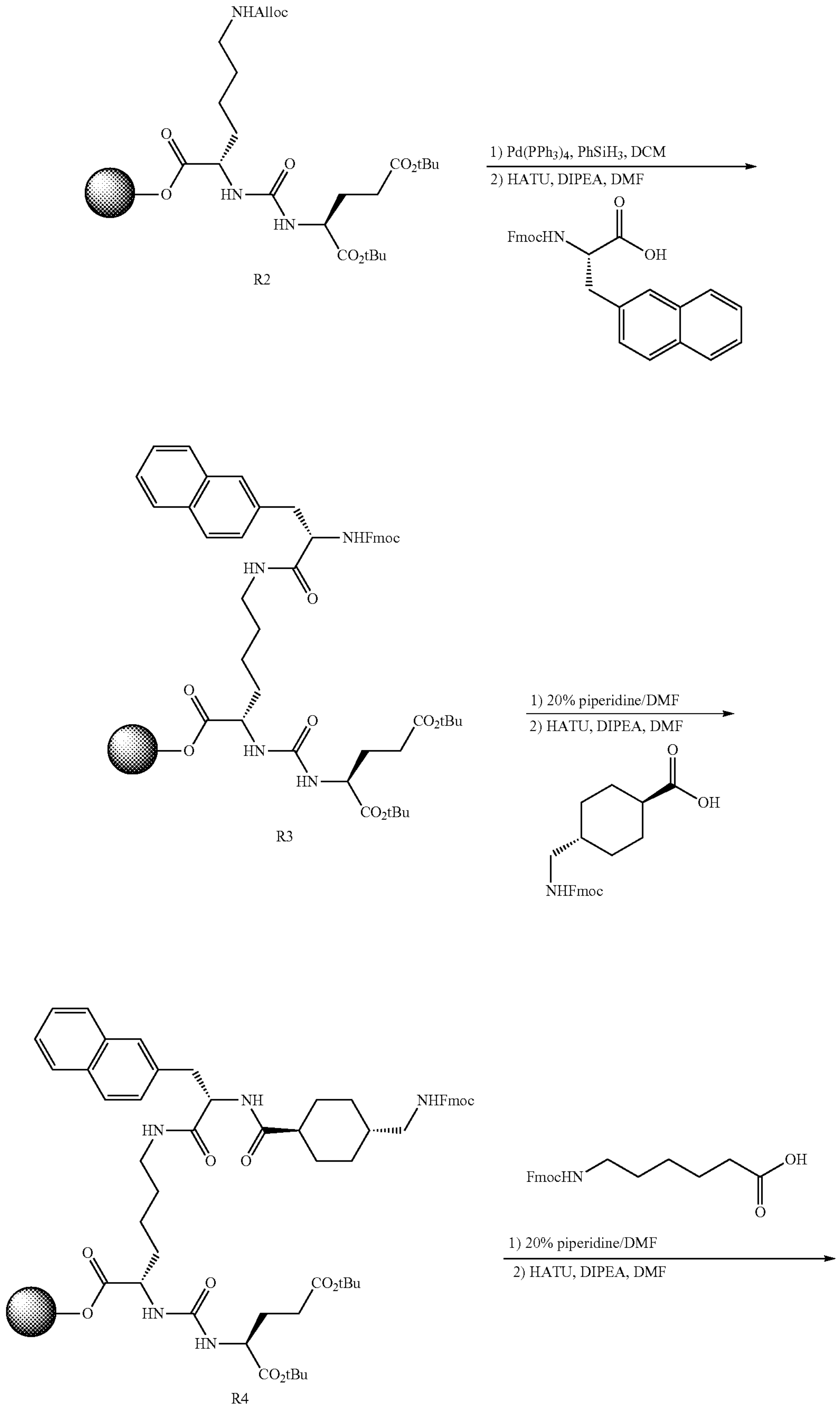

-continued

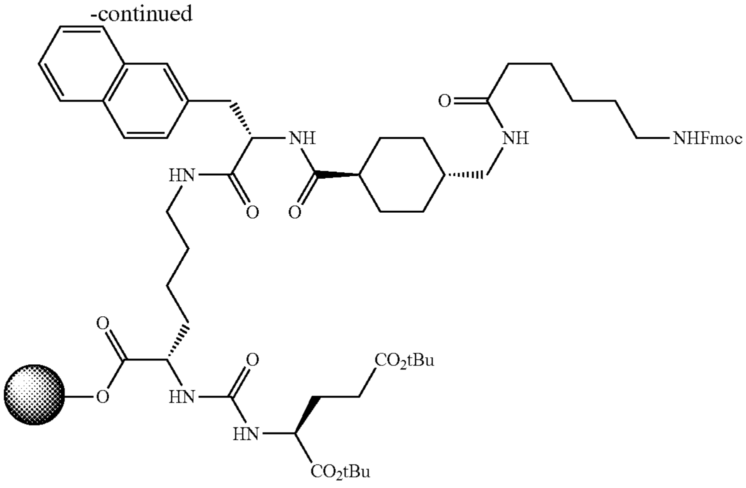

R5

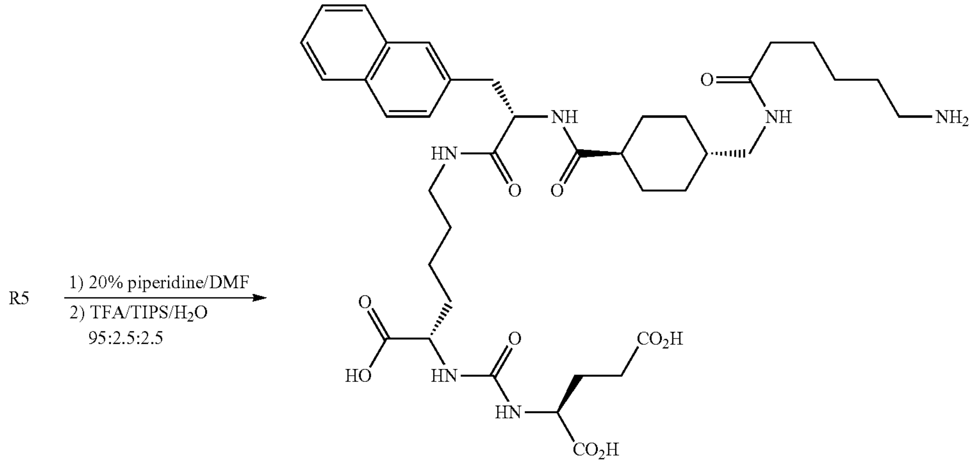

11

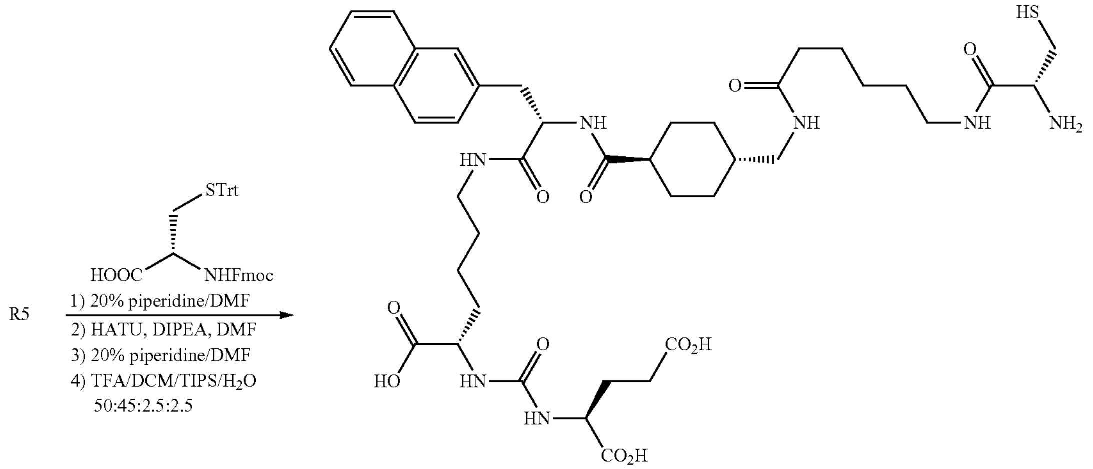

12

Commercially available Wang resin (230 mg, 0.25 mmol, 1.00 equiv.) was coupled to Fmoc-Lys (Alloc)-OH (283 mg, 0.625 mmol, 2.50 equiv.) as described in S4 (2.4 equiv. HATU, 5 equiv. DIPEA, overnight). After Fmoc deprotection (as described in S2) of R1, the resin was swollen in dichloromethane (DCM, 10 min), the solvent removed and a solution containing 4-Nitrophenyl chloroformate (101 mg, 0.500 mmol, 2.00 equiv.) and DIPEA (174 μL, 1.00 mmol, 4.00 equiv.) in anhydrous DCM (3 mL) was added to the resin. One hour after reaction, the resin was washed five times with DCM. A solution of L-Glutamic acid di-tert-butyl ester hydrochloride (148 mg, 0.500 mmol, 2.00 equiv.) and DIPEA (174 μL, 1.00 mmol, 4.00 equiv.) in anhydrous DCM (3 mL) was added to the resin and the mixture was incubated for 1 h to obtain the urea R2. Afterwards, the Alloc group was deprotected by the addition of $Pd(PPh_3)_4$ (66.4 mg, 0.058 mmol, 0.23 equiv.) and $PhSiH_3$ (308 μL, 2.50 mmol, 10 equiv.) in anhydrous DCM (3 mL). The mixture was incubated for 1 hour at room temperature. The solvent was removed and the resin was washed with DCM (5×) and DMF (5×) to remove residual reagents. Fmoc-3-(2-naphthyl)-L-alanine (219 mg, 0.500 mmol, 2.00 equiv.) was amide-coupled to the resin (2 equiv. HATU and 4 equiv. DIPEA, overnight) to afford intermediate R3. R3 was Fmoc deprotected and reacted with trans-4-(Fmoc-aminomethyl) cyclohexanecarboxylic acid (237 mg, 0.625 mmol, 2.50 equiv.) as described in S4 (2.4 equiv. HATU and 5 equiv. DIPEA, overnight) to afford intermediate R4. At this point part of the resin was stored and the synthesis was continued with approx. 0.18 mmol.

After Fmoc removal, 6-(Fmoc-amino)caproic acid (191 mg, 0.54 mmol, 3.00 equiv.) was amide-coupled to the resin (2.8 equiv. HATU and 6 equiv. DIPEA, 3 h) to obtain R5. After Fmoc deprotection, approx. 0.024 mmol of resin was cleaved via the general cleavage cocktail (95:2.5:2.5 TFA:$H_2O$:TIPS). Cleavage fractions were pooled and dried under reduced pressure for subsequent purification by RP-HPLC (gradient of 90:10 to 0:100 in 18 min water/ACN+0.1% TFA). Compound 11 was obtained as a white solid after lyophilization (5.1 mg, 0.007 mmol, 27.6% yield). m/z calculated for $C_{39}H_{56}N_6O_{10}$: $[M+H]^+$ 769,4131, detected: 769.41.

The remaining 0.15 mmol of resin were reacted with Fmoc-Cys(Trt)-OH (264 mg, 0.45 mmol, 3.00 equiv.) via the general amide coupling protocol (2.8 equiv. HATU and 6 equiv. DIPEA, 3 h). After Fmoc deprotection, the resin was cleaved twice using the second described cleavage cocktail (50:45:2.5:2.5 TFA:DCM:$H_2O$:TIPS). The fractions were combined and precipitated via the given protocol. The palette was redissolved in DMF and purified via RP-HPLC (gradient of 90:10 to 0:100 in 18 min water/ACN+0.1% TFA) to yield compound 12 as a white solid after lyophilization (31 mg, 0.035 mmol, 24% yield). m/z calculated for $C_{42}H_{62}N_7O_{11}S$: $[M+H]^+$ 872.4223, detected: 872.4.

Synthesis of Compound 23

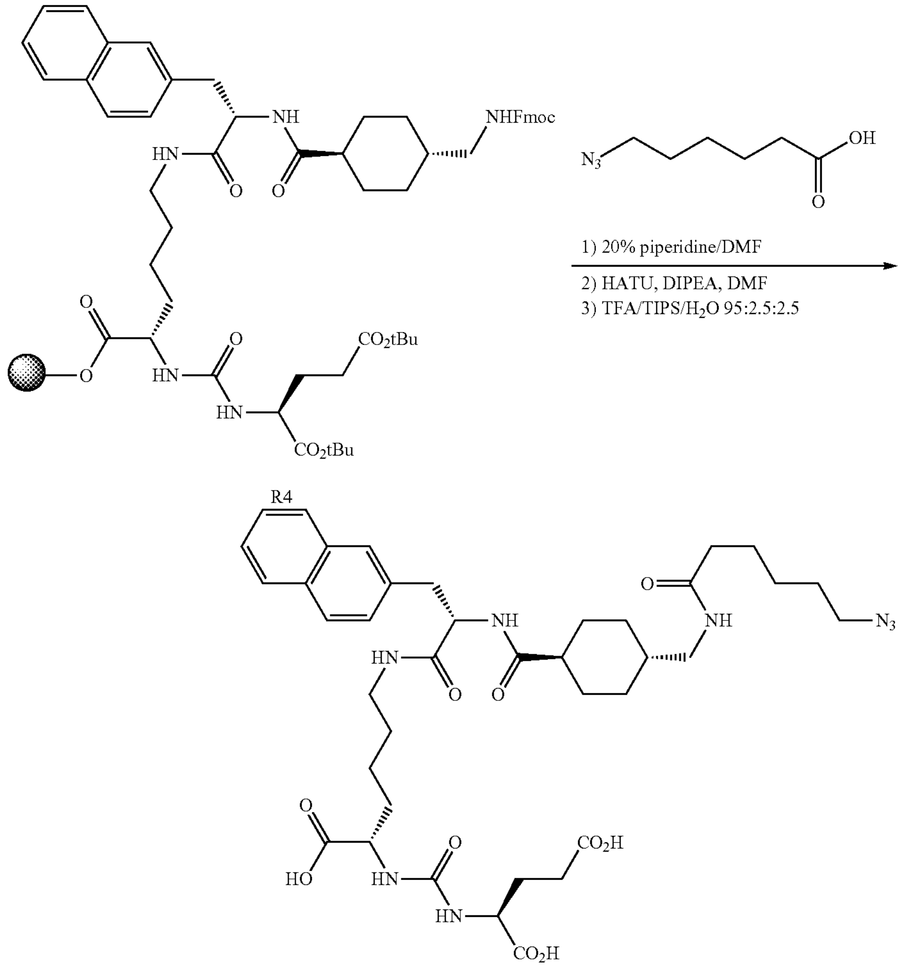

R4

23

Resin intermediate R4 (0.1 mmol, 1.0 equiv.) was subjected to general Fmoc removal conditions, and 6-Azidohexanoic acid (63 mg, 0.4 mmol, 4.00 equiv.) was amide-coupled to the resin (3.8 equiv. HATU and 8 equiv. DIPEA, 3 h). The resin was cleaved twice via the general cleavage cocktail (95:2.5:2.5 TFA:$H_2O$:TIPS). Cleavage fractions were pooled and dried under reduced pressure for subsequent purification by RP-HPLC (gradient of 90:10 to 0:100 in 18 min water/ACN+0.1% TFA). Compound 23 was obtained as a white solid after lyophilization (10.1 mg, 0.013 mmol, 13% yield). m/z calculated for $C_{39}H_{53}N_8O_{10}$: $[M-H]^-$ 793.39, detected: 793.3.

Synthesis of Compound 13

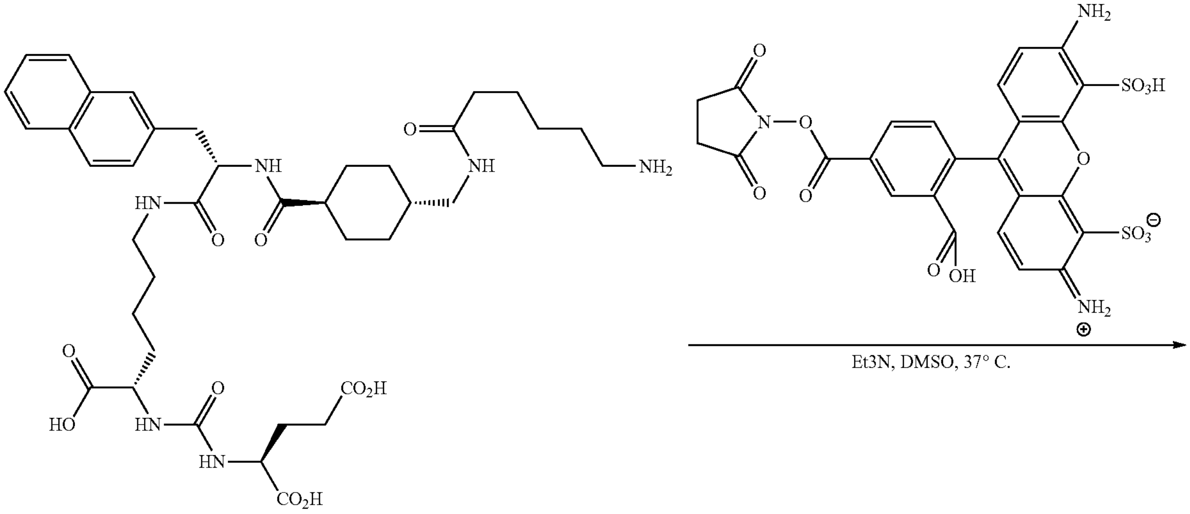

11

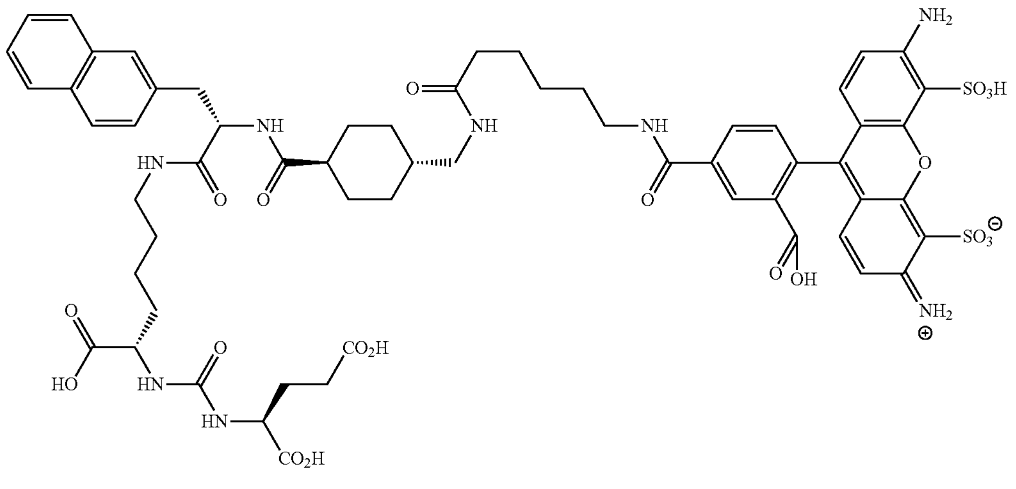

13

Stock solutions of compounds 11 and NHS-Alexa488 were prepared (5 mM in DMSO). The stock solutions were mixed 1:1 (75 μL, 375 nmol) in a 1.5 mL Eppendorf tube and triethylamine (2.1 μL, 22.5 μmol, 60 eq.) was added. The mixture was incubated in a shaker incubator for 1 h at 37° C. The crude solution was diluted with DMSO (200 μL) and was purified by RP-HPLC to yield the product after lyophilization as an orange solid (0.24 mg, 187 nmol, 50% yield). m/z calculated for $C_{60}H_{67}N_3O_{20}S_2$ $[M-H]^-$: 1283.39, detected: 1283.3.

Synthesis of Compound 14

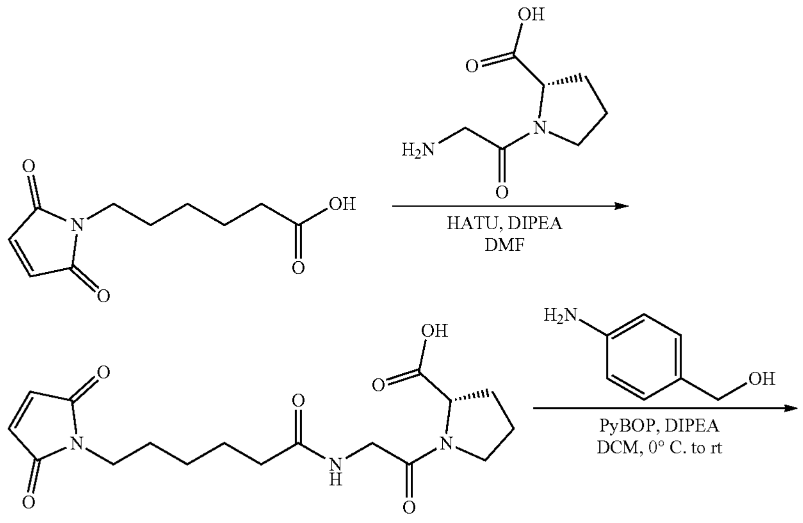

I1

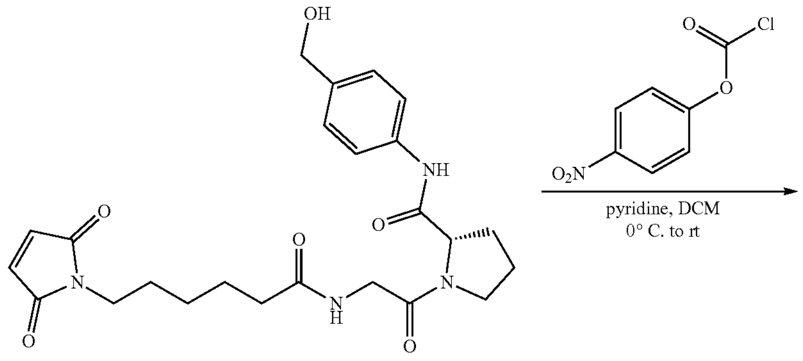

I2

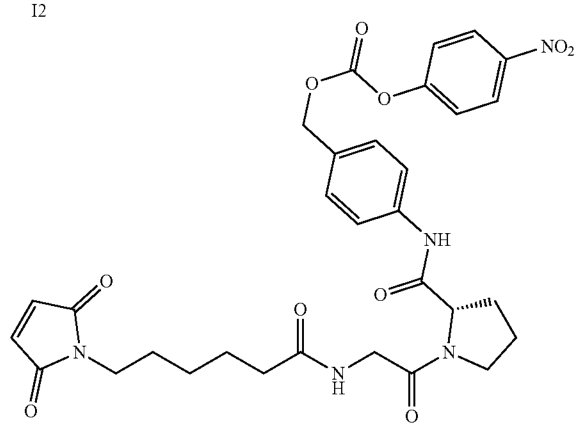

14

6-maleimidohexanoic acid (52.8 mg, 0.25 mmol, 1.00 equiv.) was loaded into a 5 mL round-bottom flask coupled with a magnetic stirring bar. The solid was dissolved in DMF (1.0 mL, 0.25 M) and HATU (95.1 mg, 0.25 mmol, 1.00 equiv.) and DIPEA (87.1 µL, 0.50 mmol, 2.00 equiv.) were added to the solution. The mixture was stirred for 30 min at room temperature before the addition of solid Gly-Pro (86.1 mg, 0.50 mmol, 2.00 equiv.). The reaction was further stirred for 2-4 hours (until completion was noted by LC-MS). The crude mixture was directly loaded onto the column of the RP-MPLC and was purified with the described gradient conditions to yield I1 after lyophilization as a white solid (62 mg, 0.17 mmol, 68% yield). m/z calculated for $C_{17}H_{22}N_3O_6$ $[M-H]^-$: 364.15, detected: 364.1.

Intermediate I1 (62.1 mg, 0.17 mmol, 1.00 equiv.), 4-aminobenzyl alcohol (31.3 mg, 0.25 mmol, 1.50 equiv.) and PyBOP (133 mg, 0.255 mmol, 1.5 equiv.) were loaded into a 5 mL round-bottom flask coupled with a magnetic stirring bar and were dissolved in DCM (1 mL, 0.17 M) and cooled to 0° C. DIPEA (59.2 μL, 0.34 mmol, 2.00 equiv.) was added dropwise to the reaction mixture, which was allow warm up to room temperature and was stirred overnight (16 h). The solution was diluted with DCM, transferred into a separatory funnel, and washed with a sat. aq. solution of $NaHCO_3$, 1M HCl, and brine. The organic phase was dried over anhydrous $Na_2SO_4$, filtered and concentrate under reduced pressure to afford a yellow oil. The crude was purified via flash column chromatography (95:5 DCM/MeOH) to afford I2 as a yellow solid (14 mg, 0.03 mmol, 17% yield). m/z calculated for $C_{24}H_{30}N_4O_5$[M-OH]$^+$: 453.22, detected: 453.3.

Intermediate I2 (14.1 mg, 0.03 mmol, 1.00 equiv.) was dissolved in a mixture of dry pyridine (3.6 μL, 0.04 mmol, 1.5 equiv.) and dry DCM (0.3 mL, 0.1 M). The solution was cooled at 0° C., then 4-nitrophenyl chloroformate (13.3 mg, 0.066 mmol, 2.20 equiv.) was added as a solution in dry DCM (0.1 mL). The reaction was stirred at room temperature for 1 h then directly purified via column chromatography (95:5 DCM/MeOH) to afford compound 14 as a white solid (17 mg, 0.027 mmol, 89% yield).

m/z calculated for $C_{31}H_{34}N_5O_{10}$ [M+H]$^+$ 636.23; observed 636.2.

Synthesis of Compound 15

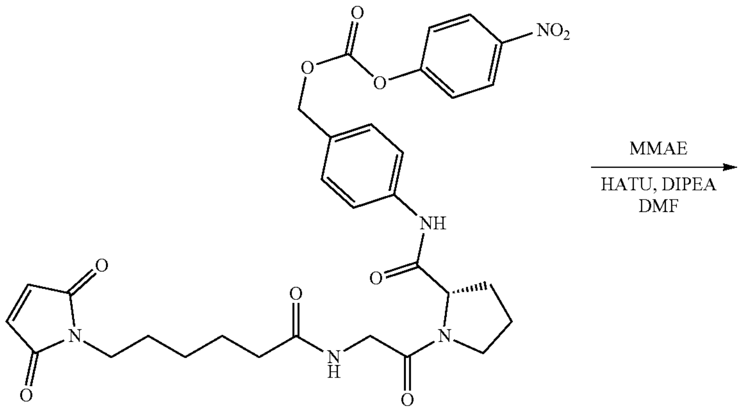

14

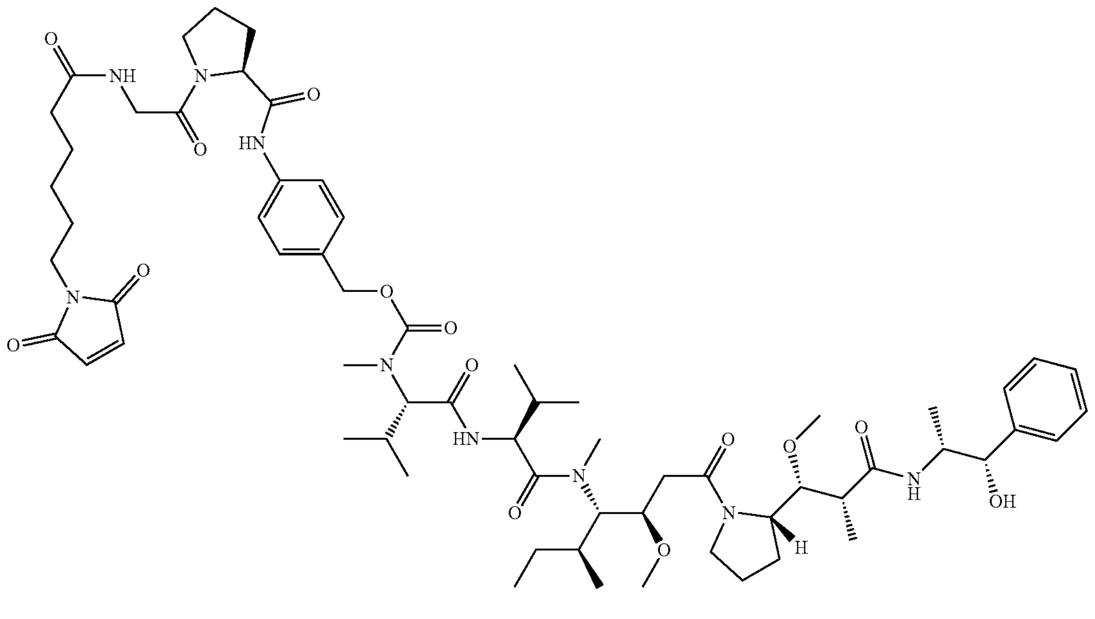

15

Compound 15 was prepared via GP1 (5 μmol scale) from compound 14 and MMAE as the respective payload. The product was a white solid after lyophilization (3.2 mg, 2.6 μmol, 53% yield). m/z calculated for $C_{64}H_{96}N_9O_{14}$ $[M+H]^+$ 1214.71; observed 1214.7.

Synthesis of Compound 16

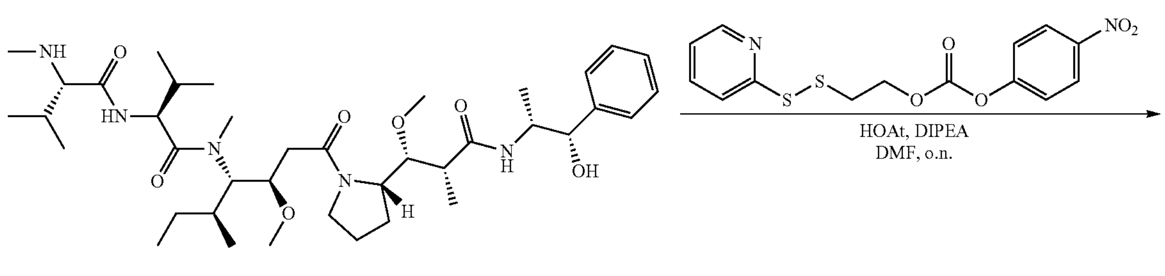

MMAE

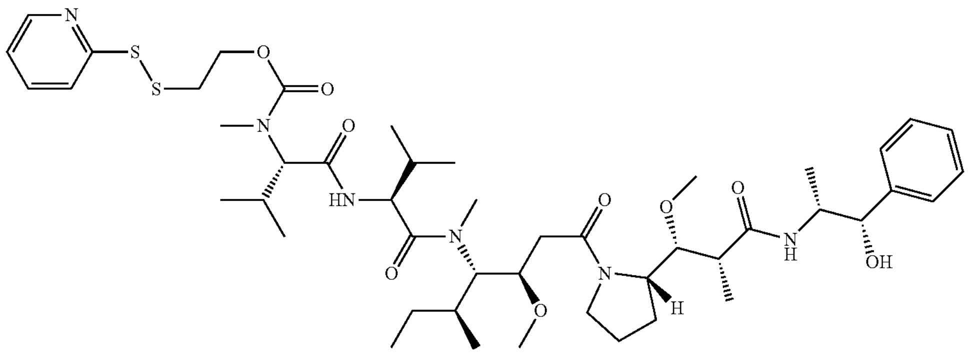

16

Compound 16 was prepared via GP1 (5 μmol scale) from commercially available 4-Nitrophenyl 2-(pyridin-2-yldisulfanyl)ethyl carbonate (Combi-Blocks) and MMAE as the respective payload. The product was a white solid after lyophilization (3.2 mg, 3.4 μmol, 69% yield). m/z calculated for $C_{47}H_{75}N_6O_9S_2$ $[M+H]^+$ 931.50; observed 931.5.

Synthesis of Compound 17

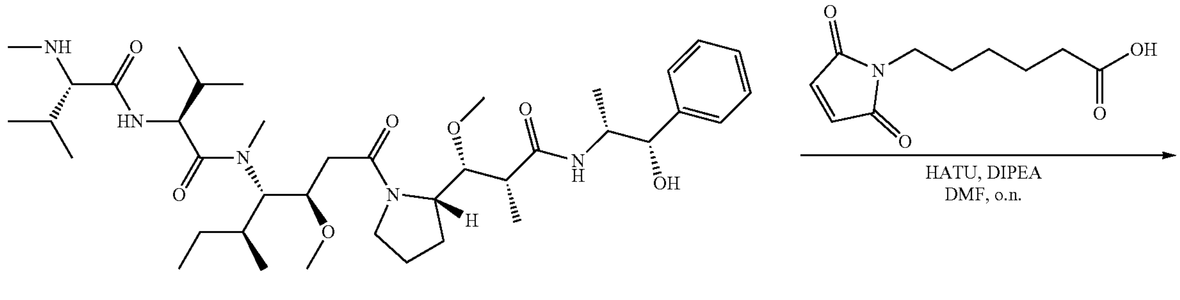

MMAE

-continued

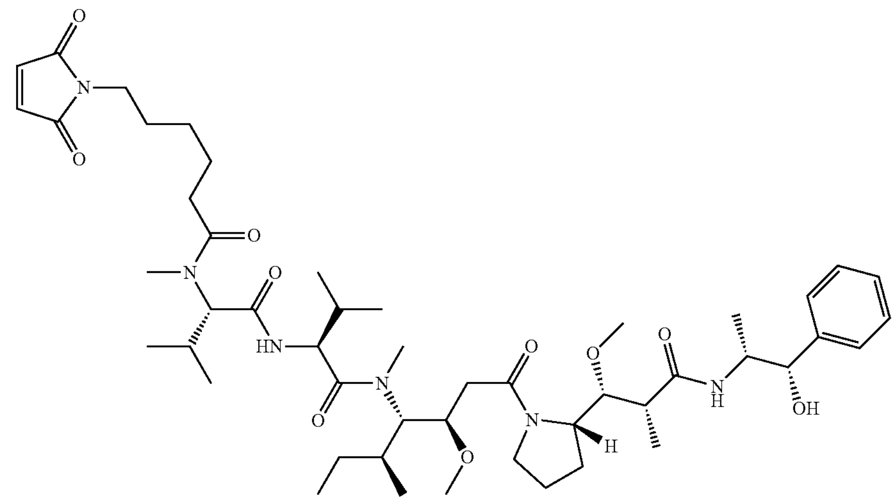

17

6-maleimidohexanoic acid (1.3 mg, 6.0 μmol, 1.2 equiv.) and HATU (1.9 mg, 5 μmol, 1.0 equiv.) were weighed into an Eppendorf tube and dissolved in DMF (0.1 mL, 0.05 M). DIPEA (1.7 μL, 10 μmol, 2.0 equiv.) was added, and the solution was incubated in a shaker incubator for 20 min at room temperature. MMAE (3.6 mg, 5.0 μmol, 1.00 equiv.) was loaded into a separate Eppendorf tube, with the necessary precaution, and the pre-activated carboxylic acid mixture was added to it. The reaction was further incubated overnight at room temperature (16 h). The crude solution was diluted with DMF (200 μL) and was purified by RP-HPLC to yield the product after lyophilization as a white solid (4 mg, 4.4 μmol, 88% yield). m/z calculated for $C_{49}H_{79}N_6O_{10}$ $[M+H]^+$: 911.58, detected: 911.5.

Synthesis of Compound 18

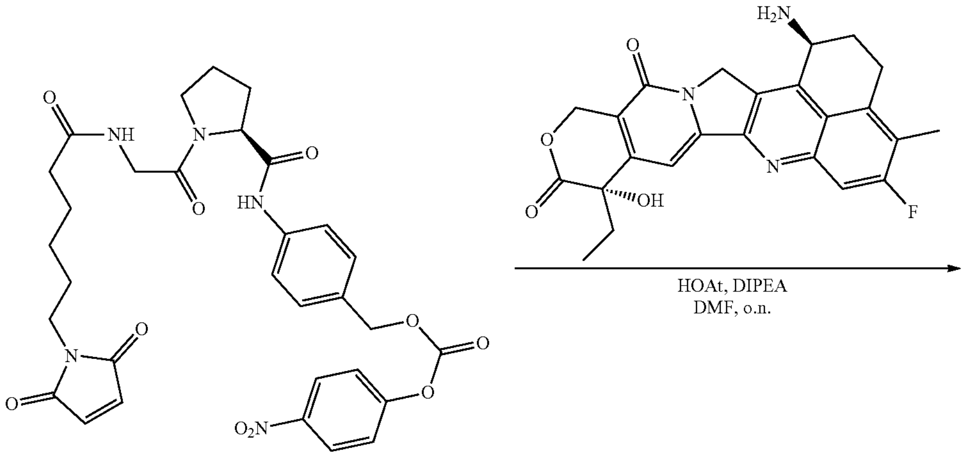

14

-continued
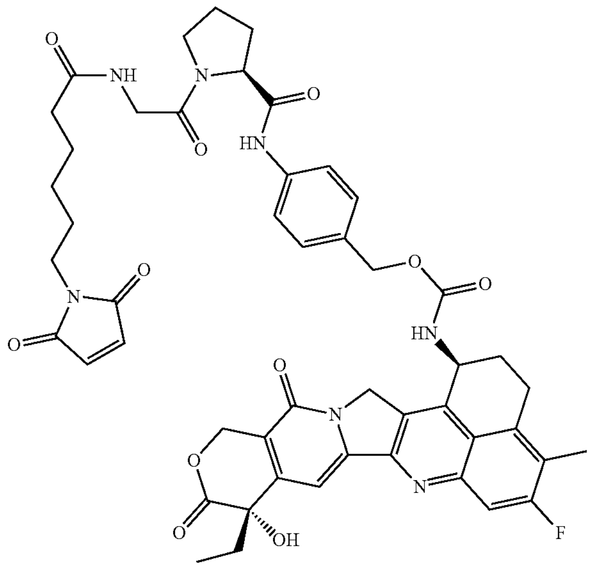
18
Compound 18 was prepared via GP1 (5 μmol scale) from compound 14 and Exatecan as the respective payload. The product was an off-white solid after lyophilization (2.4 mg, 2.6 μmol, 52% yield). m/z calculated for $C_{49}H_{51}FN_7O_{11}$ $[M+H]^+$ 932.36; observed 932.4.
Synthesis of Compound 19
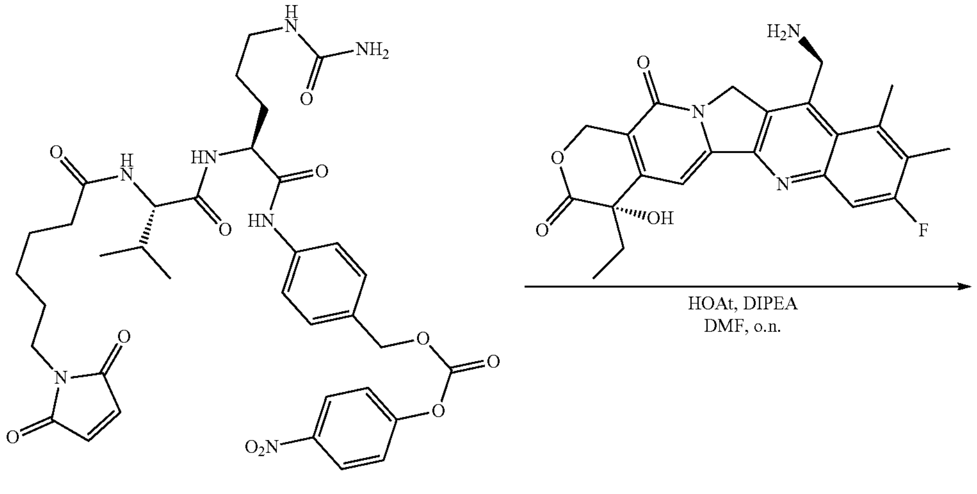

-continued
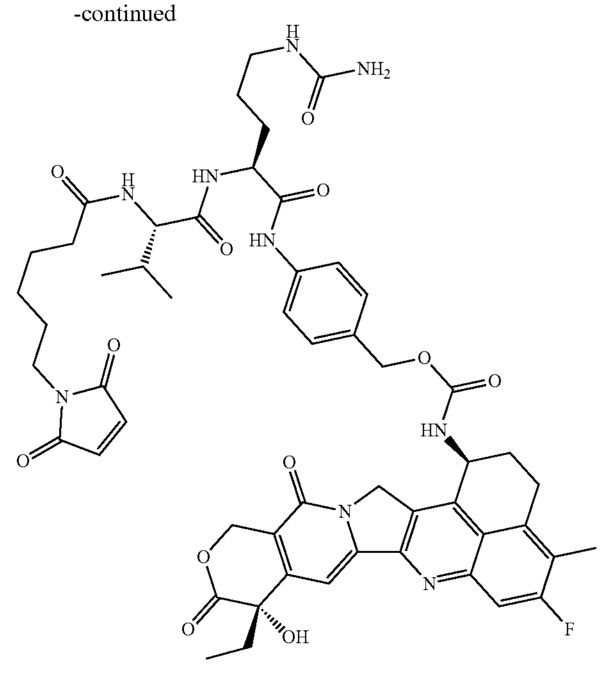
19
Compound 19 was prepared via GP1 (5 μmol scale) from commercially available MC-Val-Cit-PAB-PNP and Exatecan as the respective payload. The product was a pale-yellow solid after lyophilization (2.0 mg, 1.9 μmol, 38% yield). m/z calculated for $C_{53}H_{61}FN_9O_{12}$ $[M+H]^+$ 1034.44; observed 1034.4.
Synthesis of Compound 20
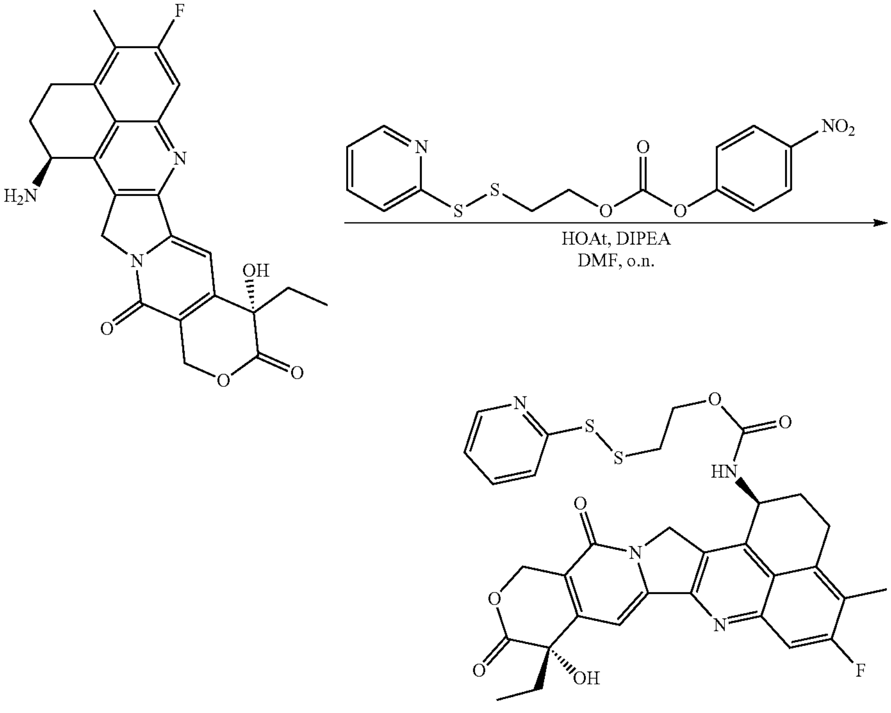
20

Compound 20 was prepared via GP1 (5 μmol scale) from commercially available 4-Nitrophenyl 2-(pyridin-2-yldisulfanyl)ethyl carbonate (Combi-Blocks) and Exatecan as the respective payload. The product was a yellow solid after lyophilization (2.7 mg, 4.2 μmol, 83% yield). m/z calculated for $C_{32}H_{30}FN_4O_6S_2$ $[M+H]^+$ 649.16; observed 649.2.

Synthesis of Compound 21

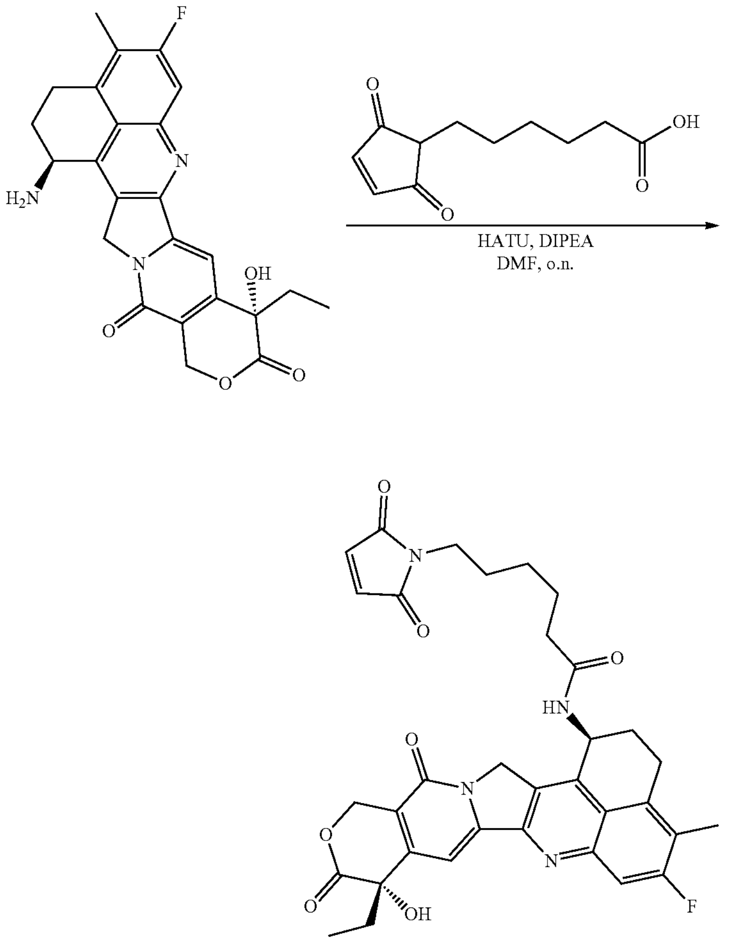

21

6-maleimidohexanoic acid (1.3 mg, 6.0 μmol, 1.2 equiv.) and HATU (1.9 mg, 5 μmol, 1.0 equiv.) were weighed into an Eppendorf tube and dissolved in DMF (0.1 mL, 0.05 M). DIPEA (1.7 μL, 10 μmol, 2.0 equiv.) was added, and the solution was incubated in a shaker incubator for 20 min at room temperature. Exatecan Mesylate (2.7 mg, 5.0 μmol, 1.00 equiv.) was loaded into a separate Eppendorf tube, with the necessary precaution, and the pre-activated carboxylic acid mixture was added to it. The reaction was further incubated overnight at room temperature (16 h). The crude solution was diluted with DMF (200 μL) and was purified by RP-HPLC to yield the product after lyophilization as a white solid (4 mg, 4.4 μmol, 88% yield). m/z calculated for $C_{49}H_{79}N_6O_{10}$ $[M+H]^+$: 911.58, detected: 911.5.

Synthesis of Compound 22

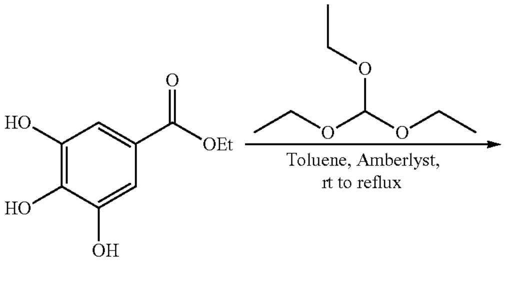

-continued

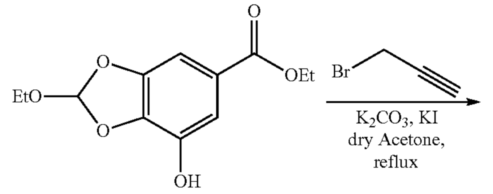

I3

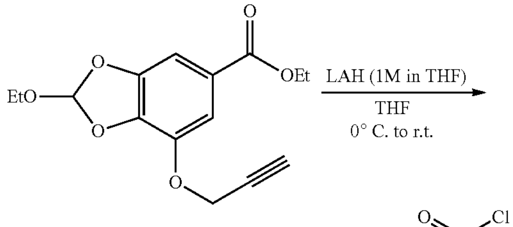

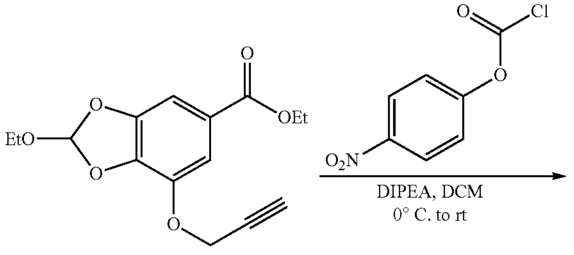

I5

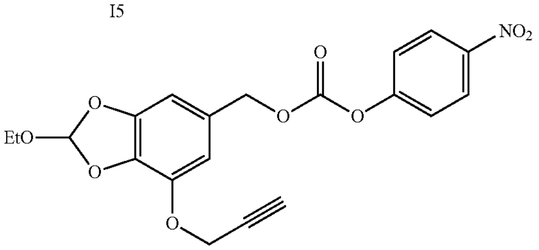

22

Amberlyst® (62 mg) was suspended in dry toluene (50 mL, 0.1 M) into a dried 250 mL round-bottom flask coupled with a magnetic stirring bar, under an Argon atmosphere. The suspension was stirred for 30 min and ethyl gallate (991 mg, 5.00 mmol, 1.00 equiv.) and triethyl orthoformate (2.5 mL, 15 mmol, 3.0 equiv.) were added at room temperature. The mixture was heated to reflux and left to stir overnight (16 h). The solution was left to cool down to room temperature, filtered through a pad of Celite and toluene was evaporated under reduced pressure. The crude residue was purified via normal-phase MPLC (0-30% gradient of EtOAc in Hexane) to yield I3 as a white solid (1.1 g, 4.3 mmol, 86% yield).

I3 (1.09 g, 4.30 mmol, 1.00 equiv.), $K_2CO_3$ (1.78 g, 12.9 mmol, 3.00 equiv.), and KI (714 mg, 4.30 mmol, 1.00 equiv.) were loaded into a dried, 250 mL round-bottom flask coupled with a magnetic stirring bar, under an Argon atmosphere. The solids were suspended in dry Acetone (43 mL, 0.1 M) and stirred for 20 min. Propargyl bromide (1.44 mL, 12.9 mmol, 3.00 equiv.) was then added and the mixture was refluxed overnight (16 h). Acetone was evaporated under reduced pressure and the crude was solubilized in EtOAc (50 mL), transferred into a separatory funnel, and washed with water (2×25 mL) and brine (25 mL). The organic phase was collected, dried over anhydrous $Na_2SO_4$, filtered, and concentrated under reduced pressure. The crude residue was purified via normal-phase MPLC (0-20% gradient of EtOAc in Hexane) to yield I4 as a white solid (1.1 g, 3.8 mmol, 88% yield).

I4 (1.11 g, 3.80 mmol, 1.00 equiv.) was loaded into a dried 250 mL round-bottom flask coupled with a magnetic stirring bar, under an Argon atmosphere. The solid was solubilized in dry THF (51 mL, 0.075 M) and the solution was cooled down to 0° C. A solution of $LiAlH_4$ in THF (1M, 11.4 mL, 11.4 mmol, 3.00 equiv.) was added slowly and the mixture was allowed to warm up to room temperature and stirred for an additional 1 h. Then, an aqueous solution of HCl (0.5 M) was added until a pH of 7-8 was observed. The mixture was then filtered into a separatory funnel and the filtrated was extracted with EtOAc (2×30 mL). The combined extracts were washed with water (25 mL) and brine (25 mL), dried over anhydrous $Na_2SO_4$, filtered, and concentrated under reduced pressure to yield I5 as a white solid (900 mg, 3.6 mmol, 95% yield).

Intermediate I5 (250 mg, 1.00 mmol, 1.00 equiv.) was loaded into a dried, 25 mL round-bottom flask coupled to a magnetic stirring bar and was dissolved in a mixture of DIPEA (0.52 mL, 3.00 mmol, 3.00 equiv.) and dry DCM (5 mL, 0.2 M). The solution was cooled to 0° C., then 4-nitrophenyl chloroformate (403 mg, 2.00 mmol, 2.00 equiv.) was added as a solution in dry DCM (1 mL). The reaction was stirred at room temperature for 1 h and DCM was concentrated under reduced pressure. The crude residue was purified via normal-phase MPLC (0-10% gradient of EtOAc in Hexane) to afford compound 22 as an off-white solid (308 mg, 0.74 mmol, 74% yield). m/z calculated for $C_{20}H_{18}NO_9$ $[M+H]^+$ 416.10; observed 416.1.

Synthesis of Compound 24

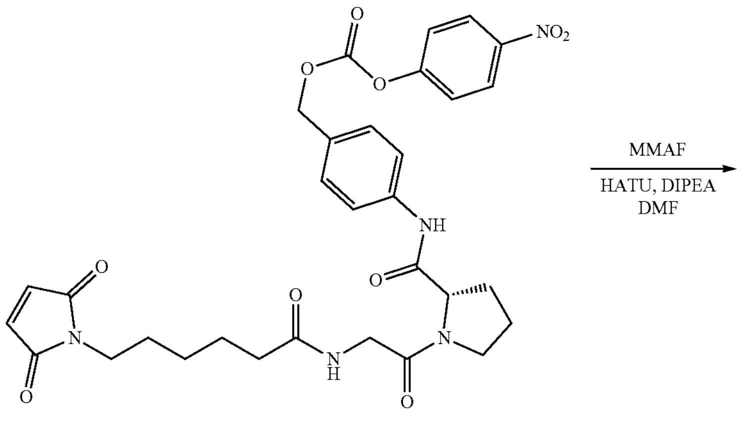

14

-continued
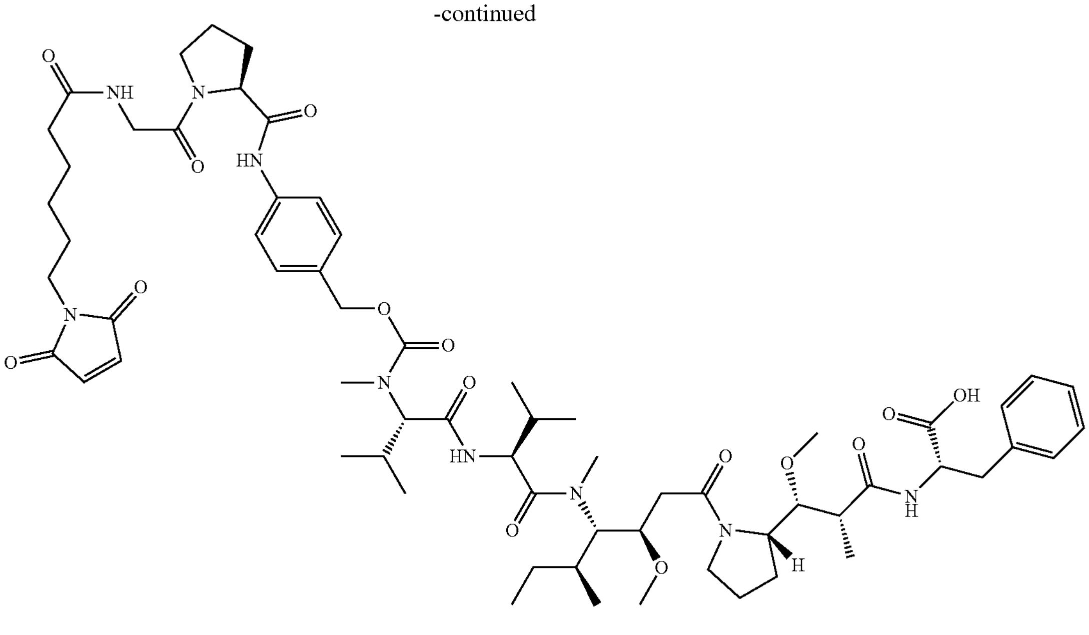
24
Compound 24 was prepared via GP1 (on a 3 μmol scale) from compound 14 and MMAF. After lyophilization, the product was obtained as a white solid (2.0 mg, 1.6 μmol, 54% yield). m/z calculated for $C_{64}H_{92}N_{9}O_{15}$ [M−H]$^-$ 1226.67; m/z observed 1226.6.
Synthesis of Compound 25
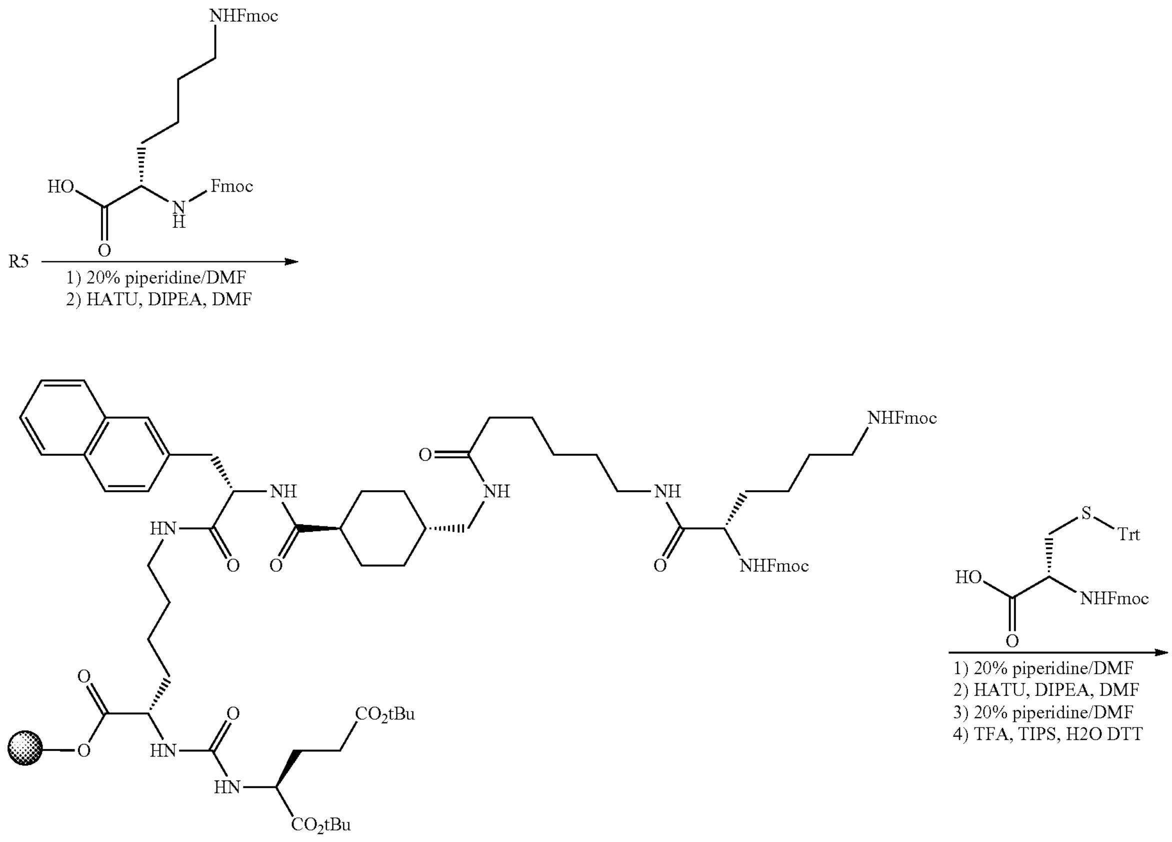
R6

-continued

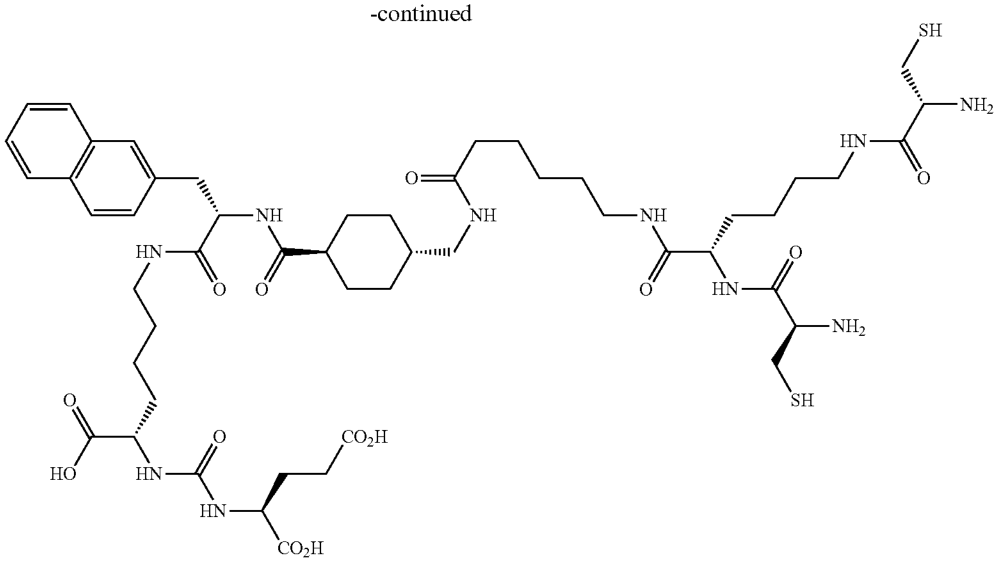

25

R5 (48 pprox. 0.05 mmol of resin) was reacted with N-2,N-6-bis(9-fluorenylmethyloxycarbonyl)-L-lysine (88.6 mg, 0.15 mmol, 3.00 equiv.) via the general amide coupling protocol (2.8 equiv. HATU and 6 equiv. DI PEA, 2 h) to obtain R6. Fmoc deprotection was performed, and the intermediate was treated with Fmoc-Cys(Trt)-OH (176 mg, 0.30 mmol, 6.00 equiv.) following the general amide coupling protocol (5.8 equiv. HATU and 12 equiv. DIPEA, 2 h). After a second Fmoc deprotection, the resin was cleaved twice using the second described cleavage cocktail (50:45:2.5:2.5 TFA:DCM:thioanisole:TIPS). The fractions were combined and precipitated via the given protocol. The palette was redissolved in DMF and purified via RP-HPLC (gradient of 90:10 to 0:100 in 18 min water/CAN+0.1% TFA) to yield compound 25 as a white solid after lyophilization (3.5 mg, 5.4 μmol, 11% yield). m/z calculated for $C_{51}H_{79}N_{10}O_{13}S_2$: $[M+H]^+$ 1103.53, detected: 1103.5.

Compound 26

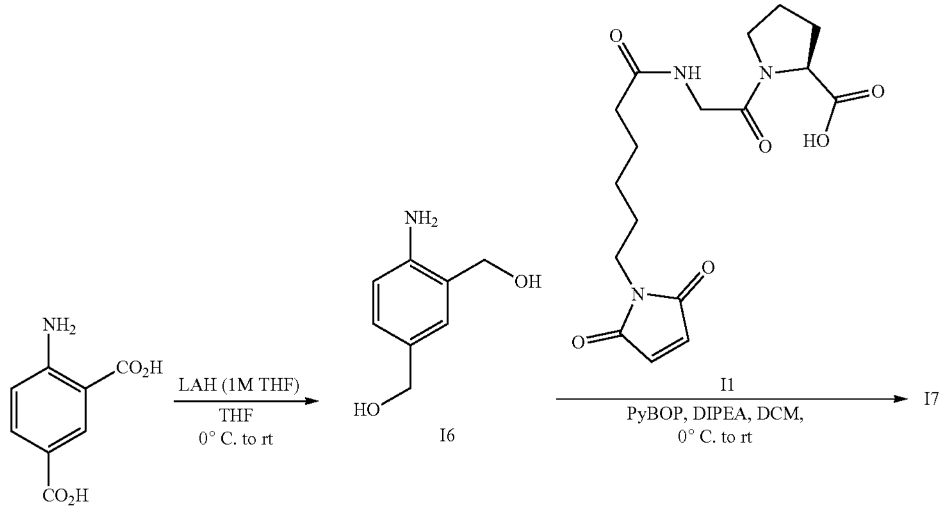

-continued
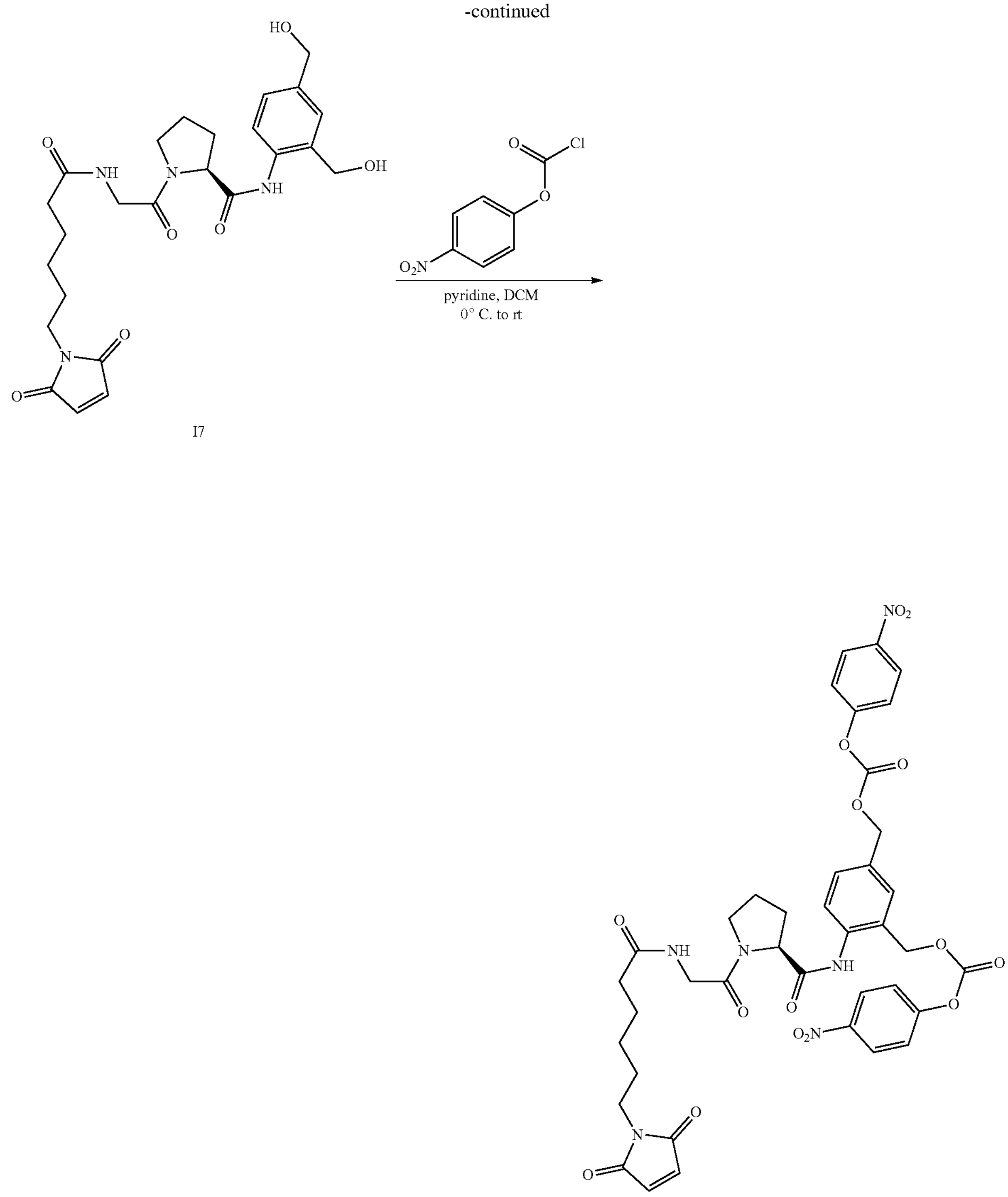
I7
26
Compound 26 may be synthesised by the route shown above.

Compound 27
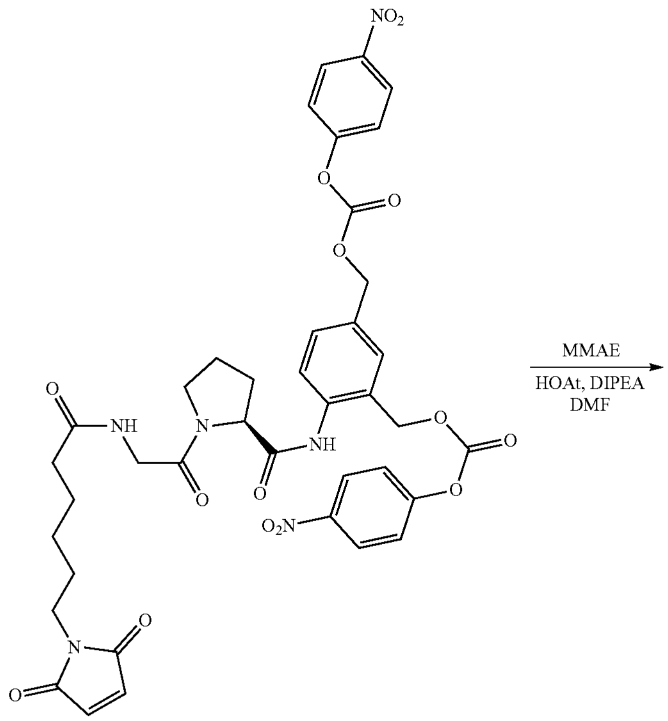
26
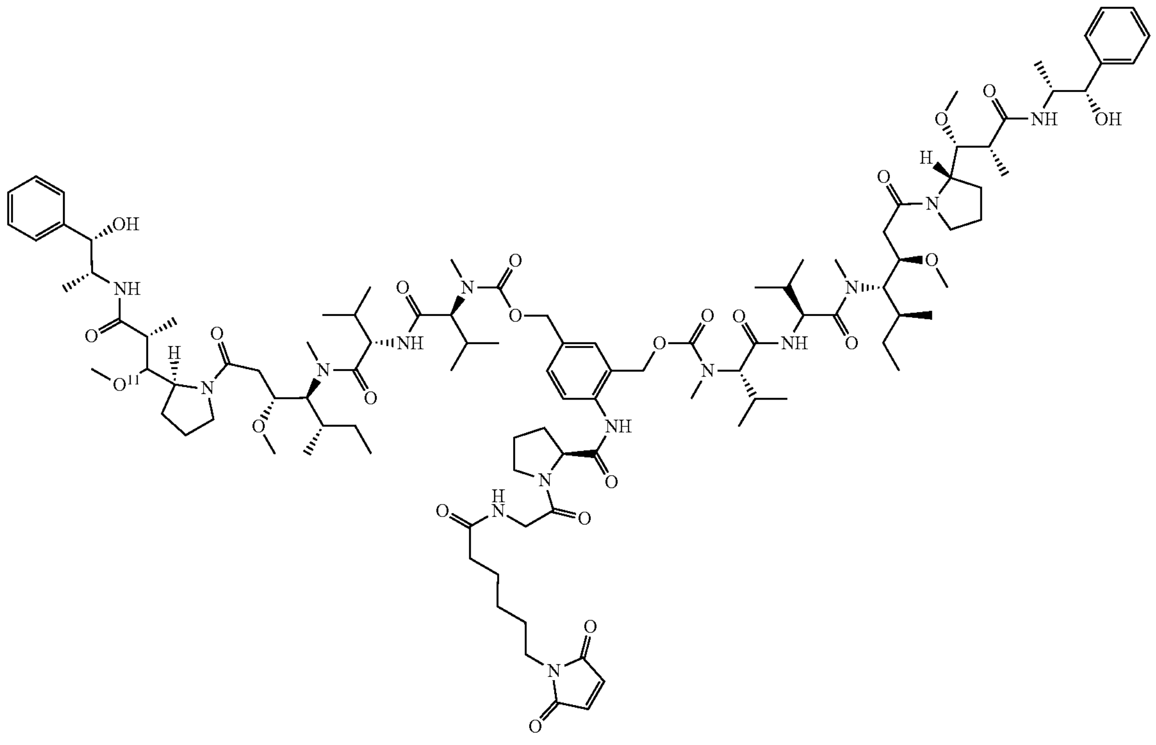
27

Compound 27 may be synthesised by the reaction shown above.

Example 1—Synthesis of Conjugates

Synthesis of Conjugate 1

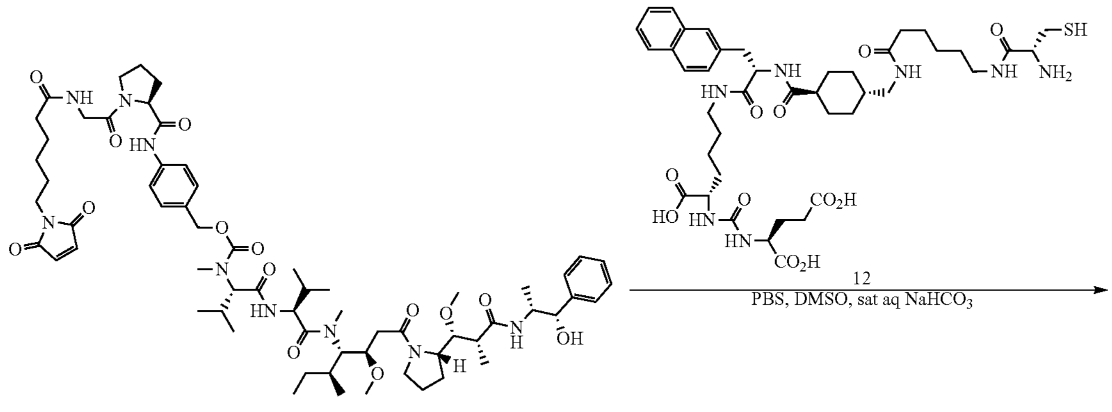

12

15

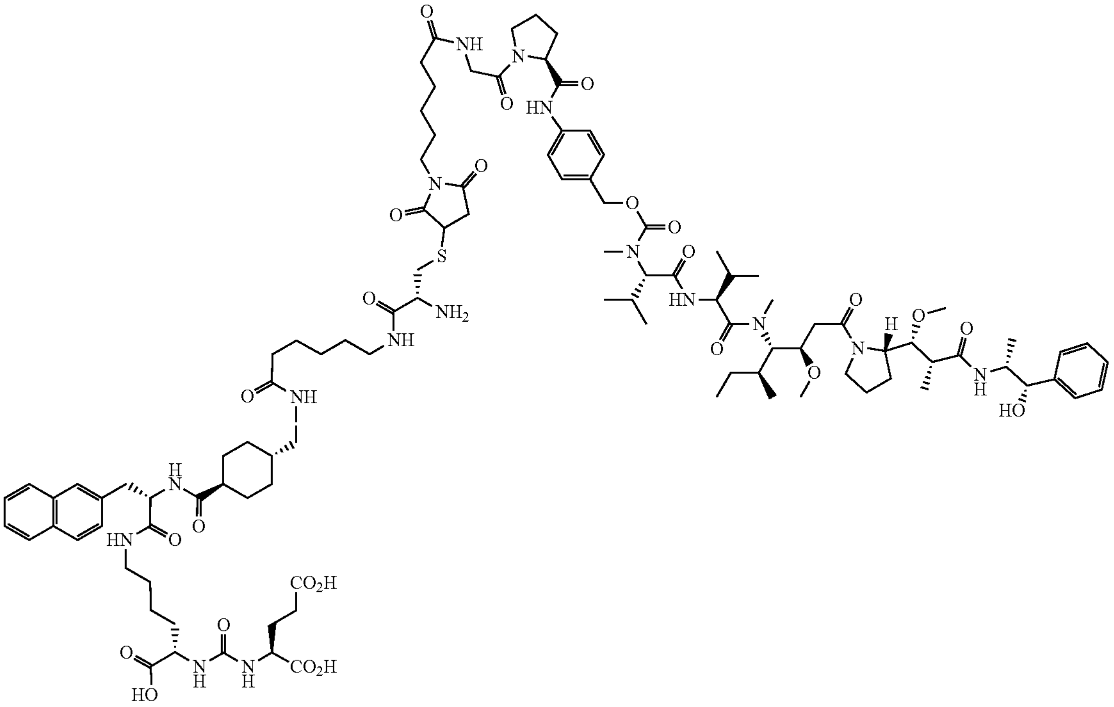

1

Conjugate 1 was prepared via GP2 (1.8 μmol scale) from compounds 12 and 15. The product was a white solid after lyophilization (2.0 mg, 0.96 μmol, 53% yield).

Figure 2A:
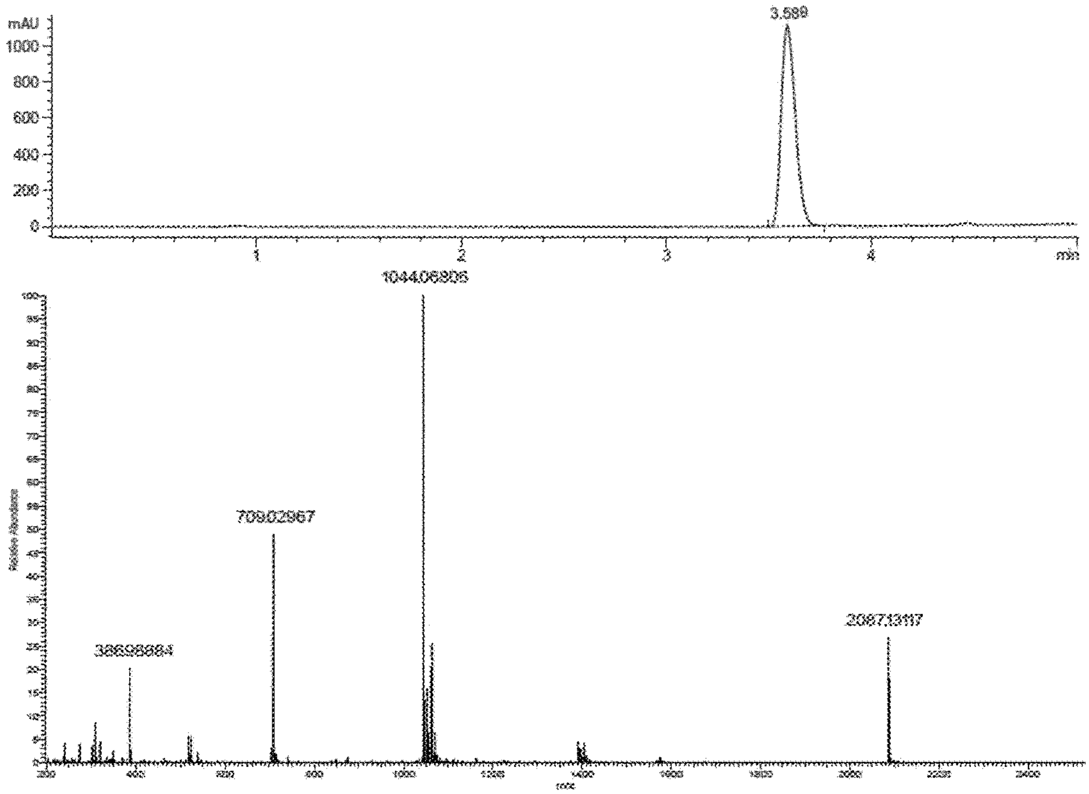
FIG. 2 shows the chromatograms and high-resolution MS data of Conjugate 1 (FIG. 2A), Conjugate 2 (FIG. 2B), Conjugate 3 (FIG. 2C), Conjugate 4 (FIG. 2D) as well as the chromatograms of Conjugate 5 (FIG. 2E), Conjugate 6 (FIG. 2F) and Conjugate 7 (FIG. 2G).

HRMS (ESI+), m/z calculated for $C_{106}H_{158}N_{16}O_{25}S$ $[M+2H]^{2+}$ 1044.06637; observed 1044.06807. The LC-MS chromatogram and high-resolution MS data are shown in FIG. 2A.

Figure 2B:
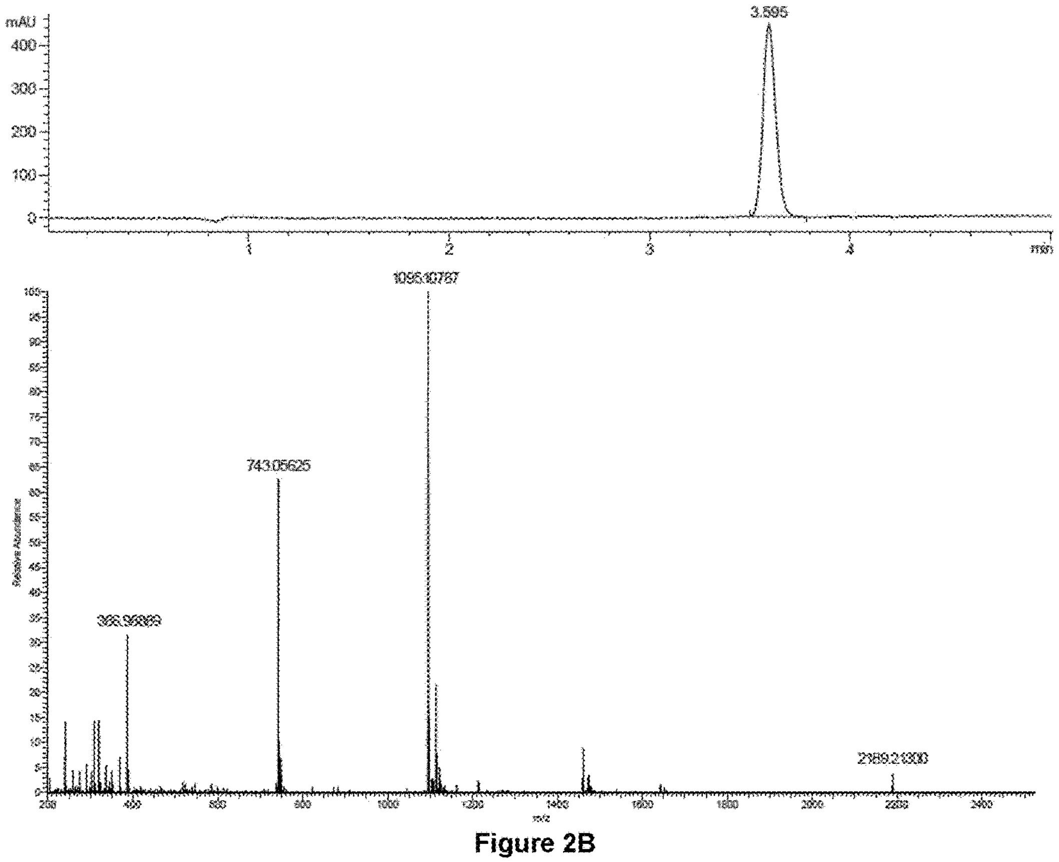

Synthesis of Conjugate 2 (Comparative)
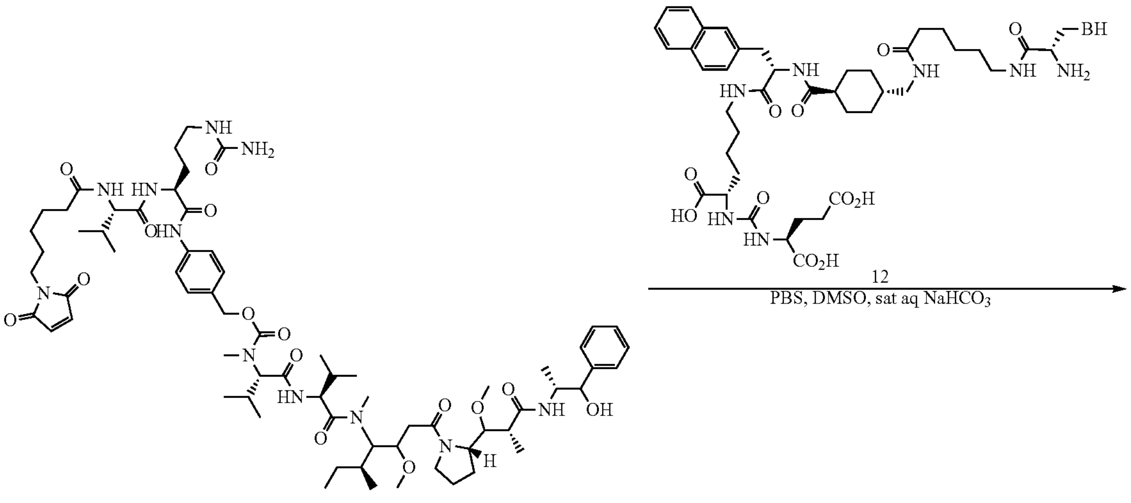
MC-Val-Cit-PAB-MMAE
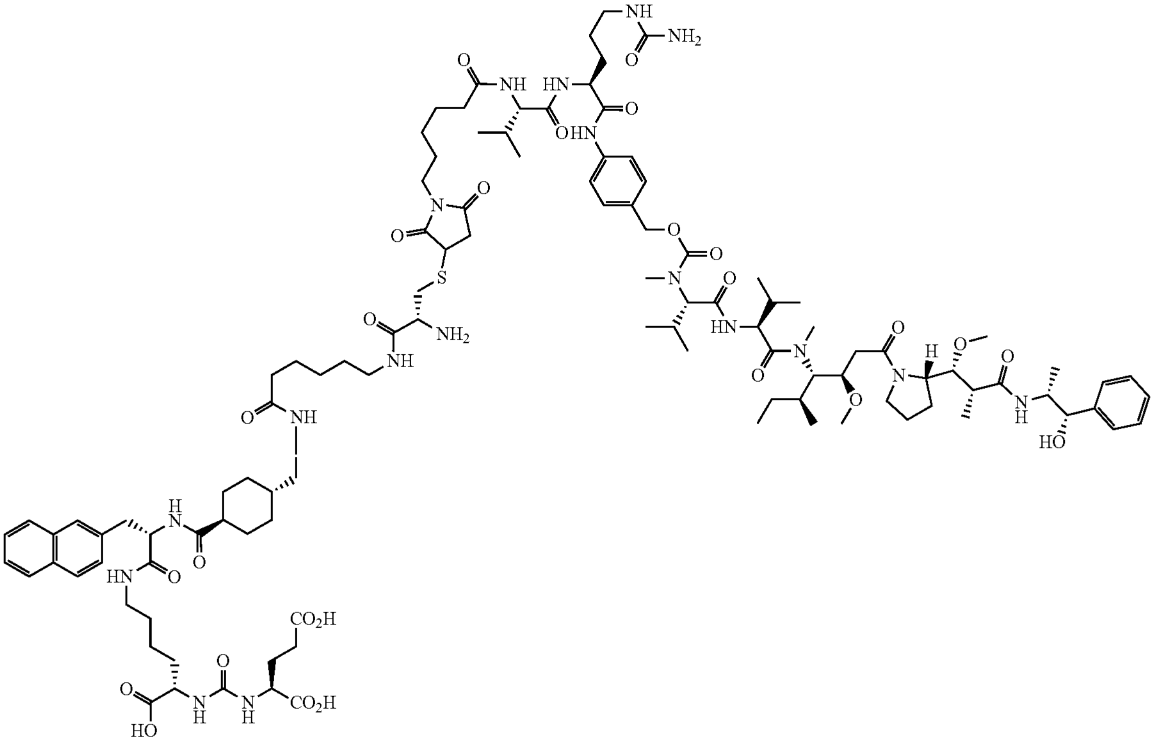
2
Conjugate 2 was prepared via GP2 (1.5 μmol scale) from compound 12 and MC-Val-Cit-PAB-MMAE. The product was a white solid after lyophilization (2.0 mg, 0.91 μmol, 61% yield).
HRMS (ESI+), m/z calculated for $C_{110}H_{168}N_{18}O_{26}S$ $[M+2H]^{2+}$ 1095.10602; observed 1095.10787. The LC-MS chromatogram and high-resolution MS data are shown in FIG. 2B.

Figure 2C:
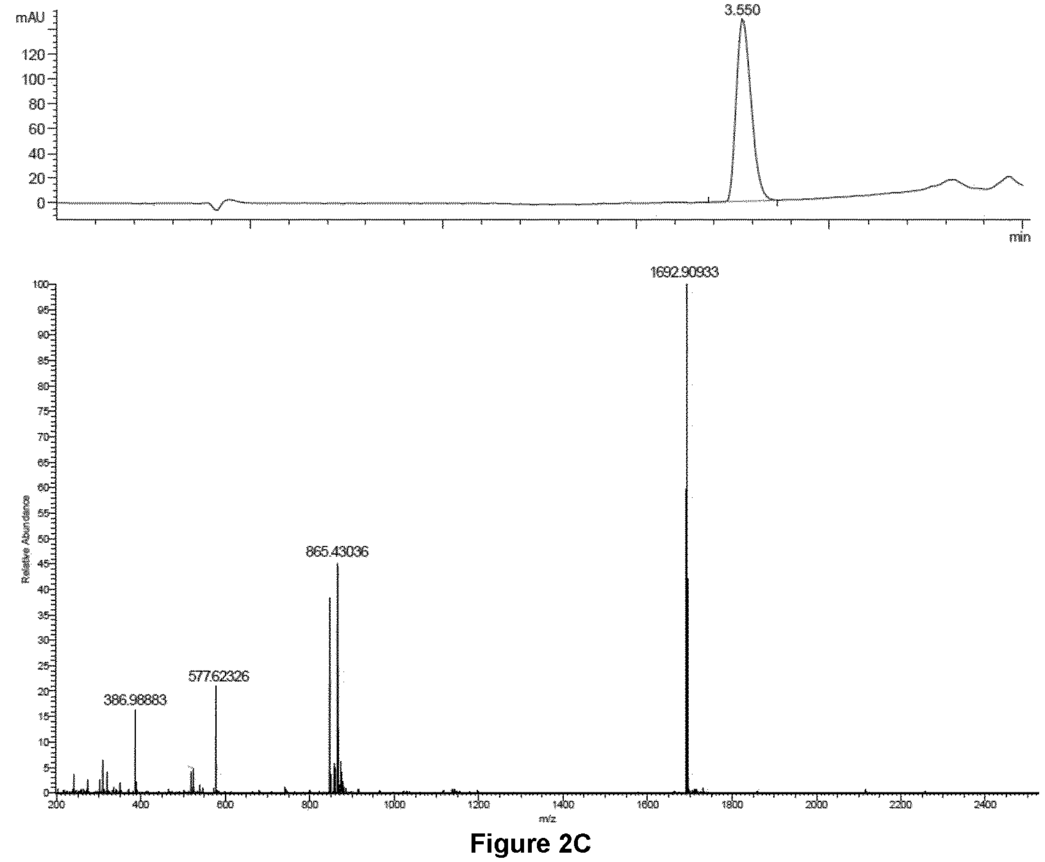

Synthesis of Conjugate 3 (Comparative)
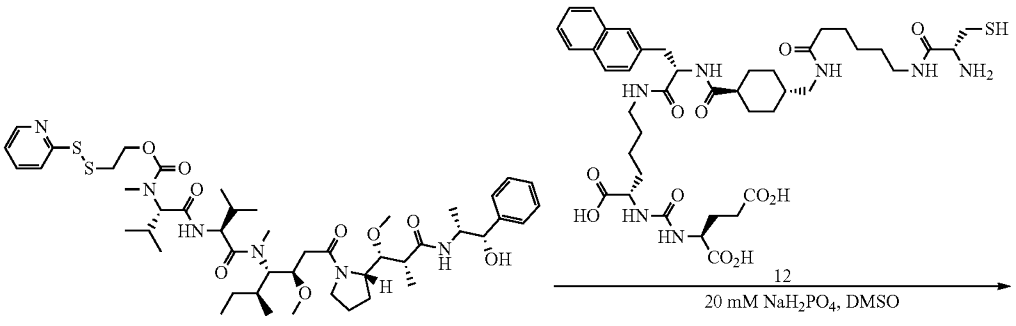
16
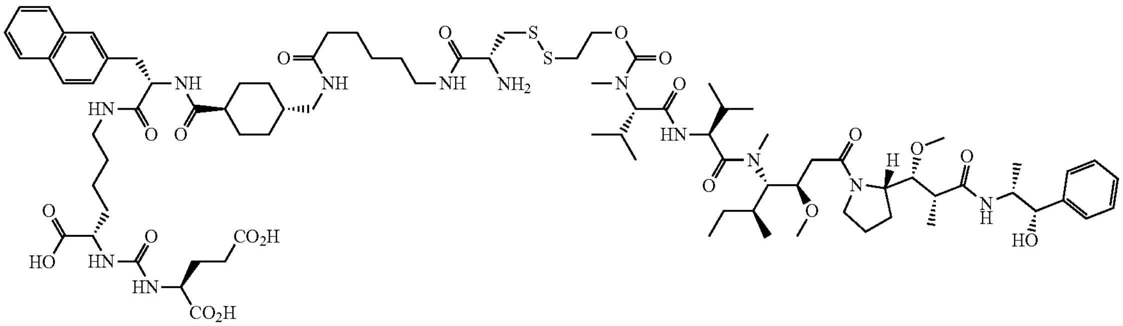
3
Conjugate 3 was prepared via GP3 (1.7 μmol scale) from compounds 12 and 16. The product was a white solid after lyophilization (1.3 mg, 0.77 μmol, 45% yield).
HRMS (ESI+), m/z calculated for $C_{84}H_{131}N_{12}O_{20}S_2[M+H]^+$ 1691.90385; observed 1691.90761. The LC-MS chromatogram and high-resolution MS data are shown in FIG. 2C.
Synthesis of Conjugate 4 (Comparative)
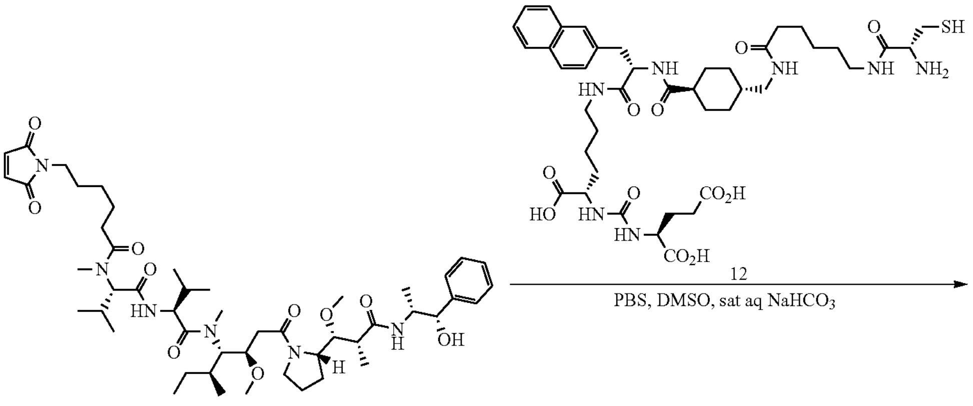
17

Figure 2D:
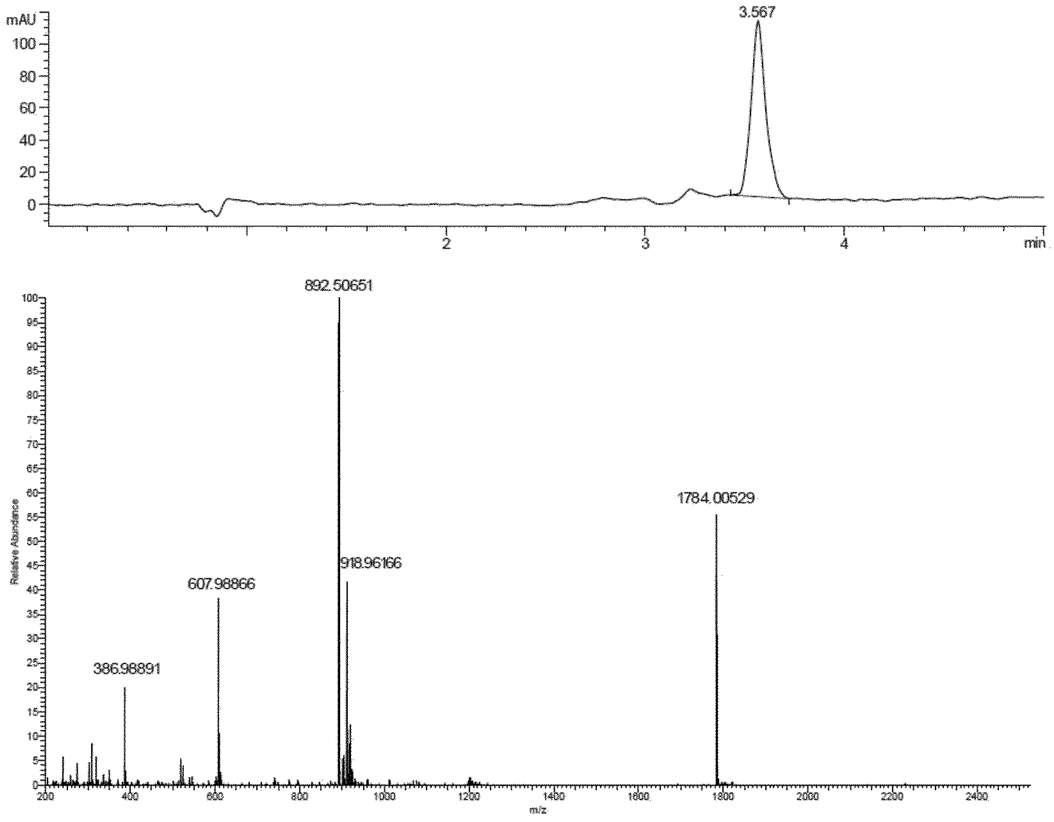

-continued
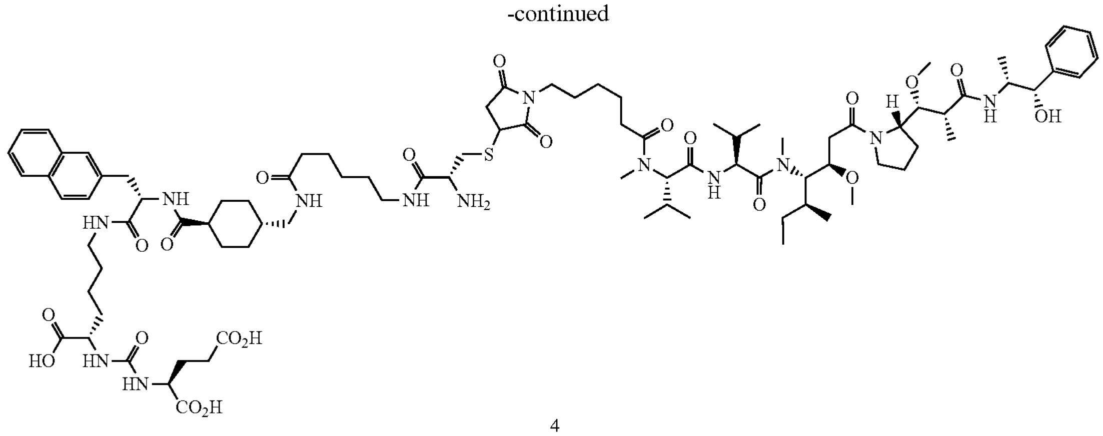
4
Conjugate 4 was prepared via GP2 (1.7 μmol scale) from compounds 12 and 17. The product was a white solid after lyophilization (1.7 mg, 0.95 μmol, 56% yield).
HRMS (ESI+), m/z calculated for $C_{91}H_{140}N_{13}O_{21}S$ $[M+H]^+$ 1783.00020; observed 1783.00239. The LC-MS chromatogram and high-resolution MS data are shown in FIG. 2D.
Synthesis of Conjugate 5
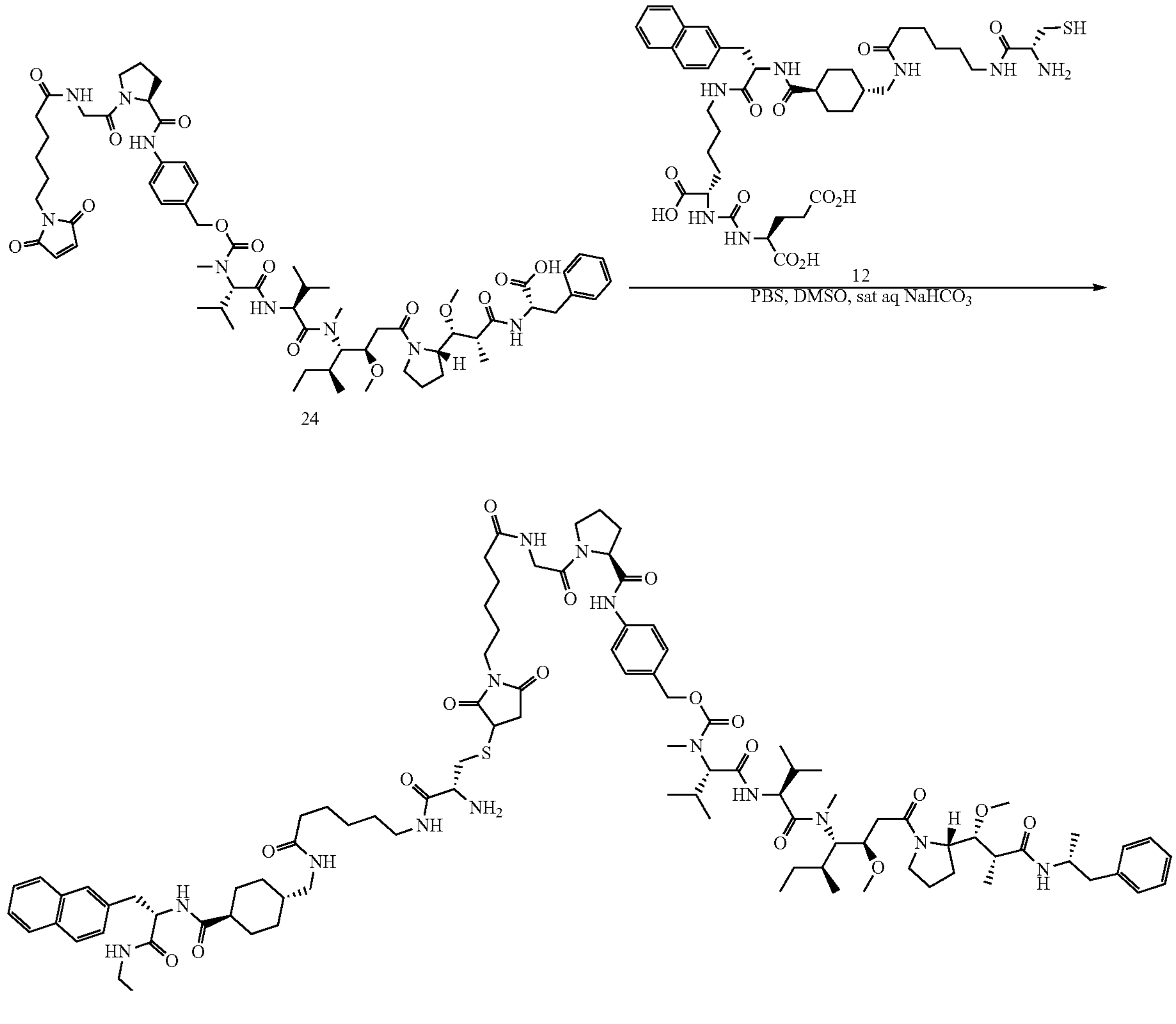
12
24

Figure 2E:
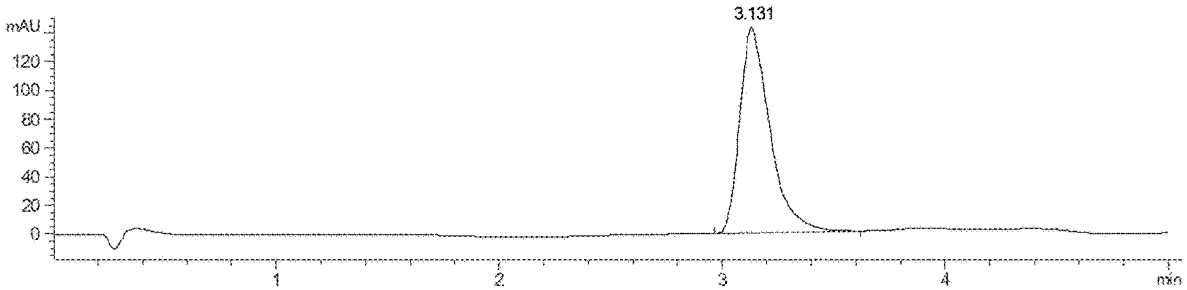

-continued
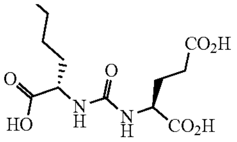
Conjugate 5 was prepared via GP2 (on a 1 μmol scale) from compounds 12 and 24. After lyophilization, the product was obtained as a white solid (1.0 mg, 0.48 μmol, 48% yield). m/z calculated for $C_{106}H_{156}N_{16}O_{26}S$ $[M+2H]^{2+}$ 1051.05; m/z observed 1051.1. The LC-MS chromatogram is shown in FIG. 2E.
Synthesis of Conjugate 6
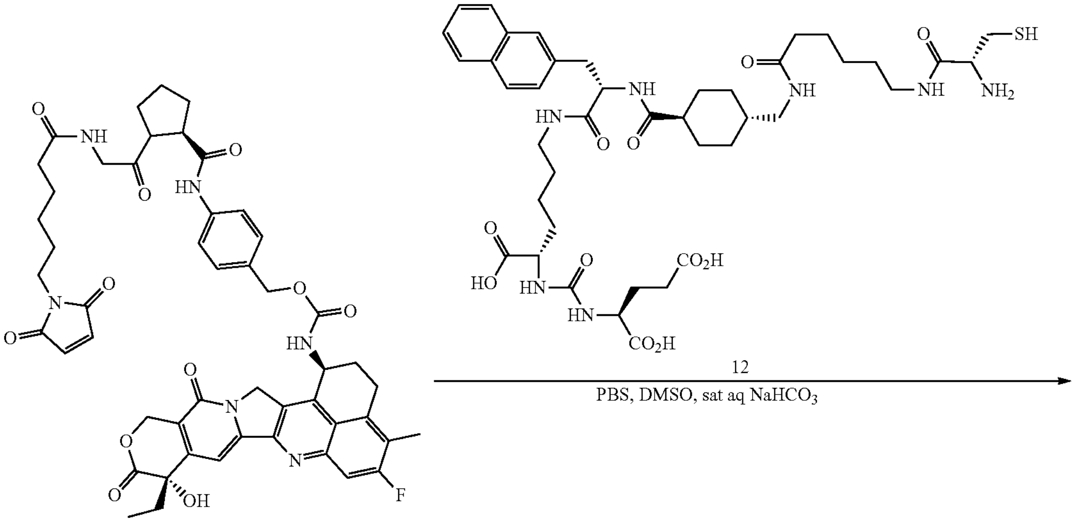
18
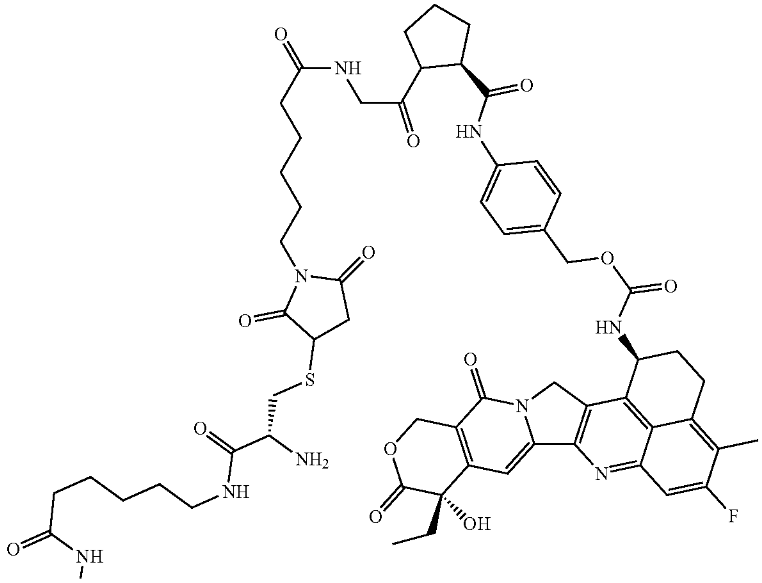

Figure 2F:
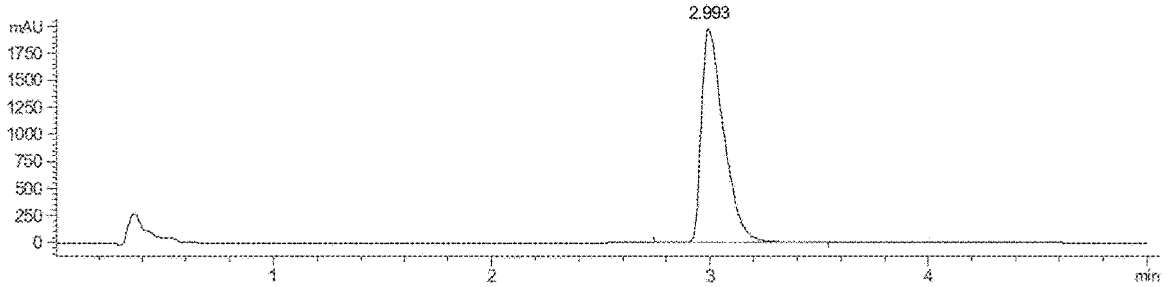

-continued
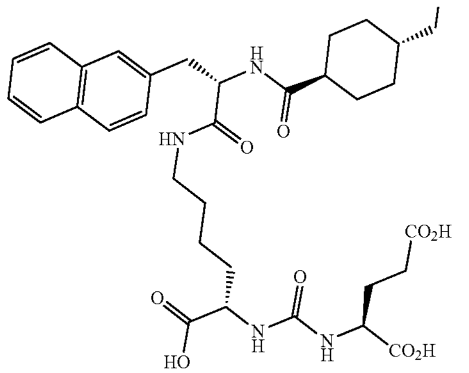
6
Conjugate 6 was prepared via GP2 (on a 1.1 μmol scale) from compounds 12 and 18. After lyophilization, the product was obtained as a yellow solid (1.1 mg, 0.61 μmol, 55% yield). m/z calculated for $C_{91}H_{112}FN_{14}O_{22}S$ $[M+H]^+$ 1804.78; m/z observed 1804.7.
The LC-MS chromatogram is shown in FIG. 2F.
Synthesis of Conjugate 7
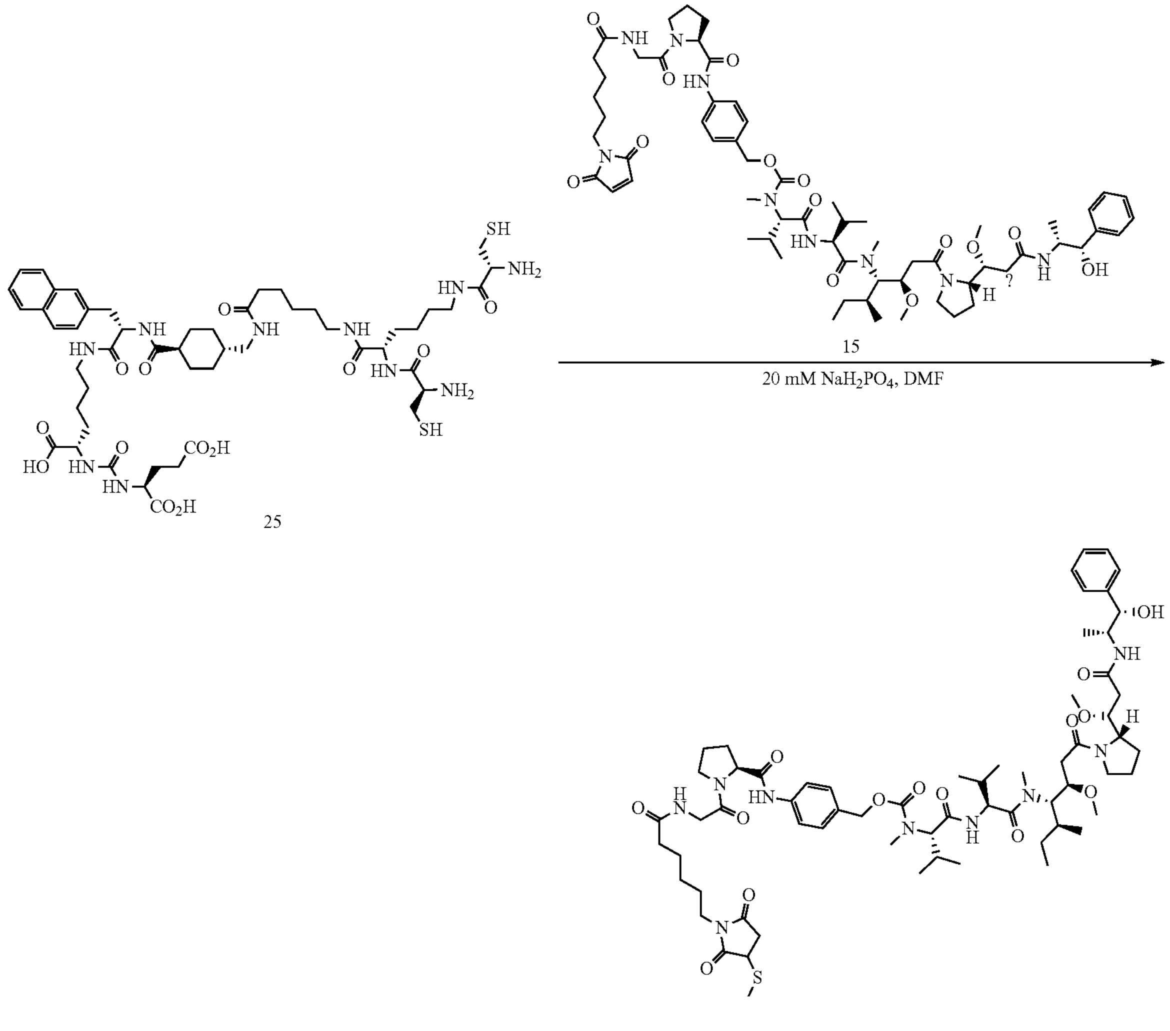
25
15

Figure 2G:
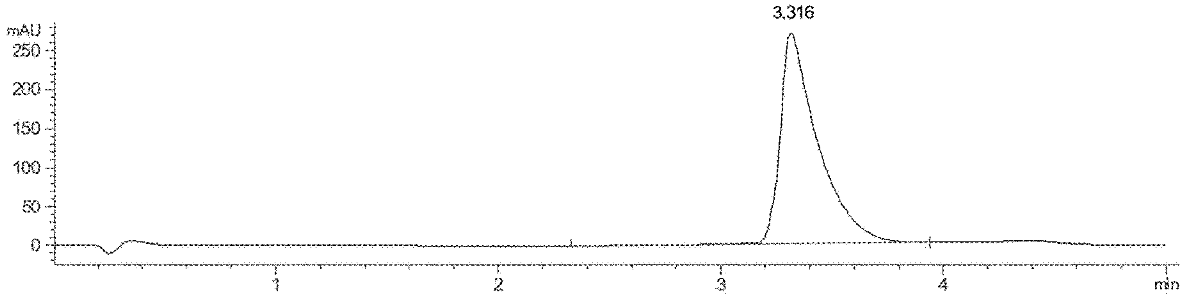

-continued
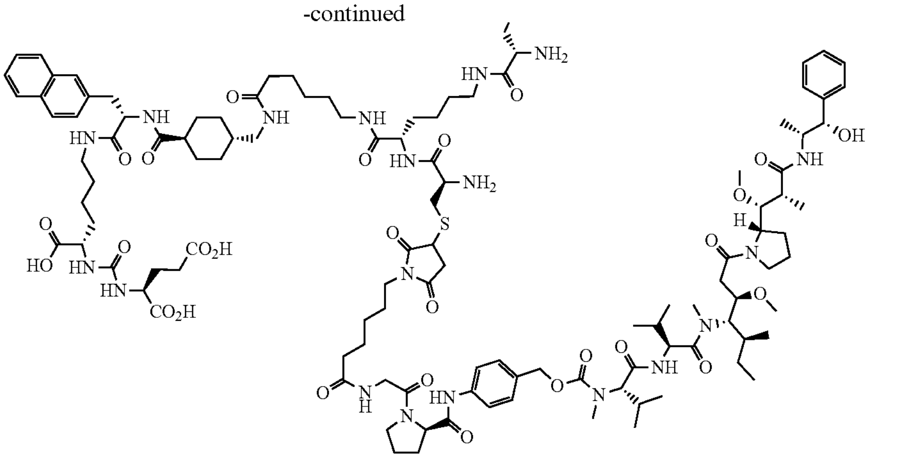
7
Conjugate 7 was prepared via GP2 (on a 2 μmol scale) from compounds 15 and 25. After lyophilization, the product was obtained as a white solid (3.0 mg, 0.85 μmol, 48% yield). m/z calculated for $C_{179}H_{270}N_{28}O_{41}S_2[M+2H]^{2+}$ 1766.97; m/z observed 1766.7.
The LC-MS chromatogram is shown in FIG. 2G.
Conjugate 8
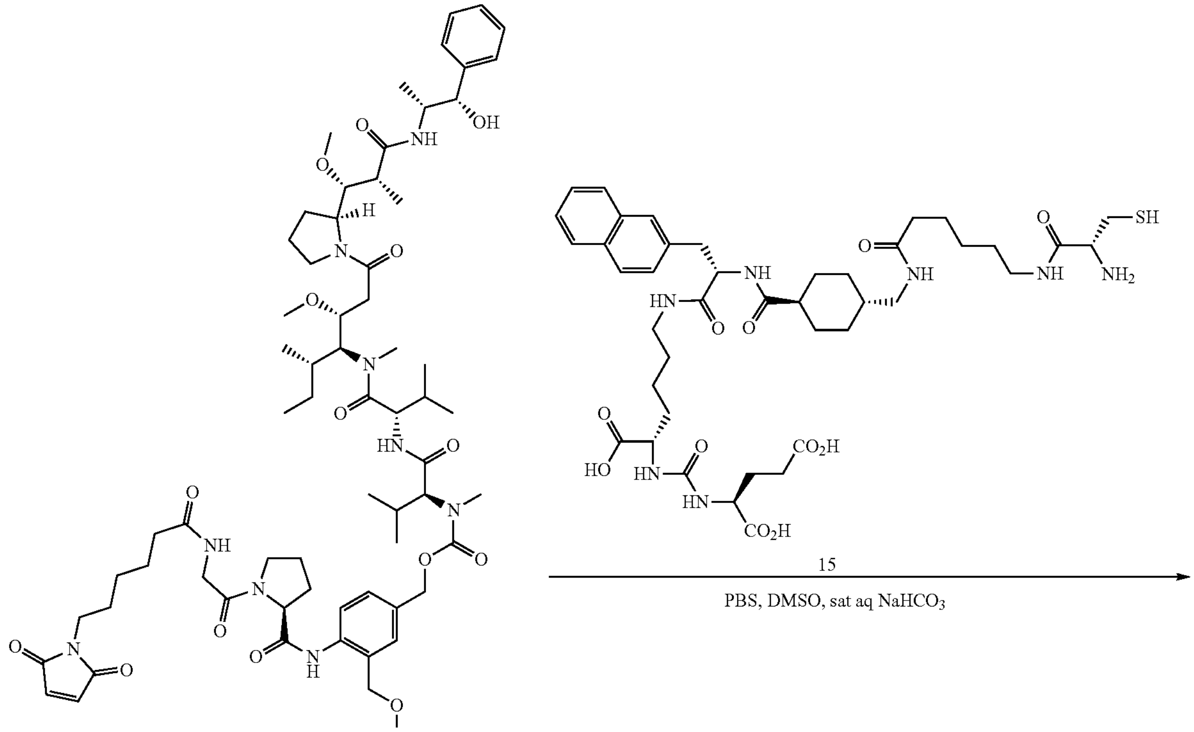

-continued
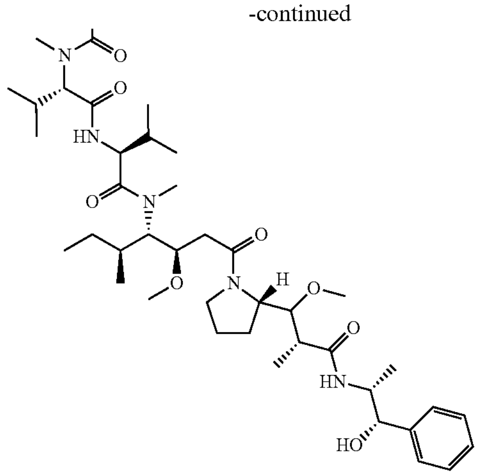
27
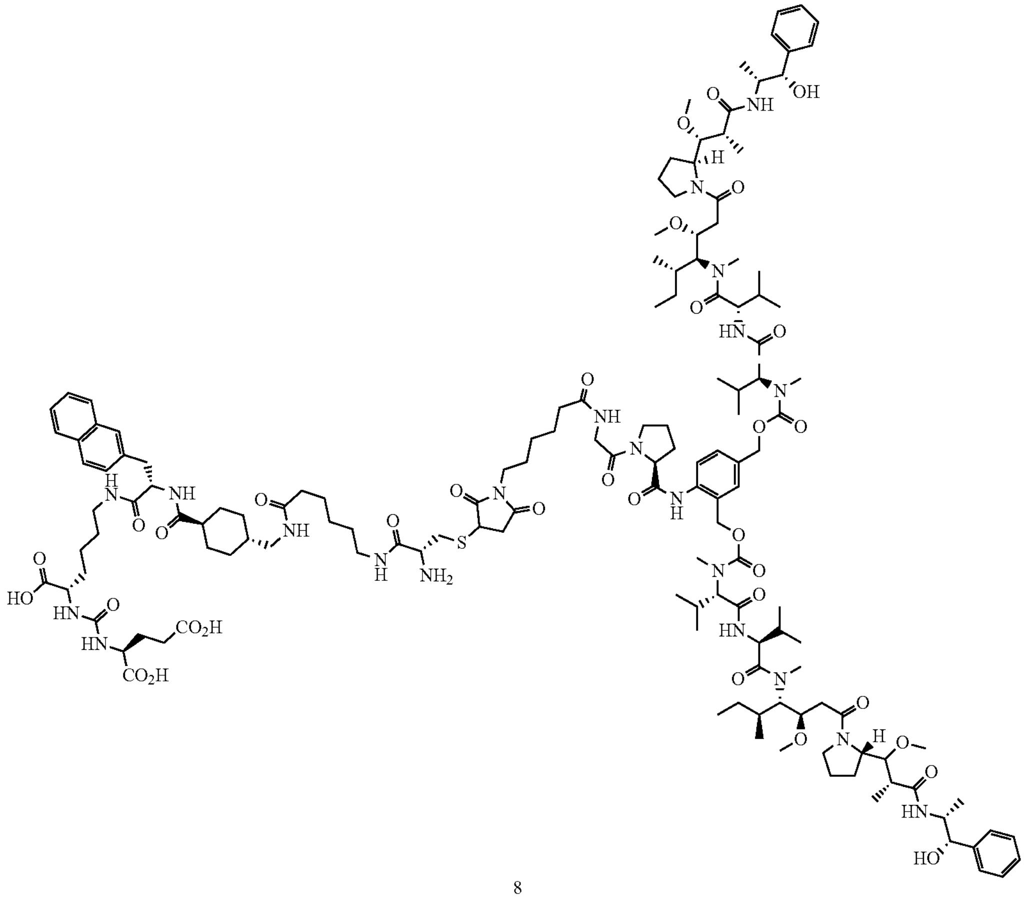
8

Conjugate may be synthesised by the reaction shown above.
Conjugates 9 and 10
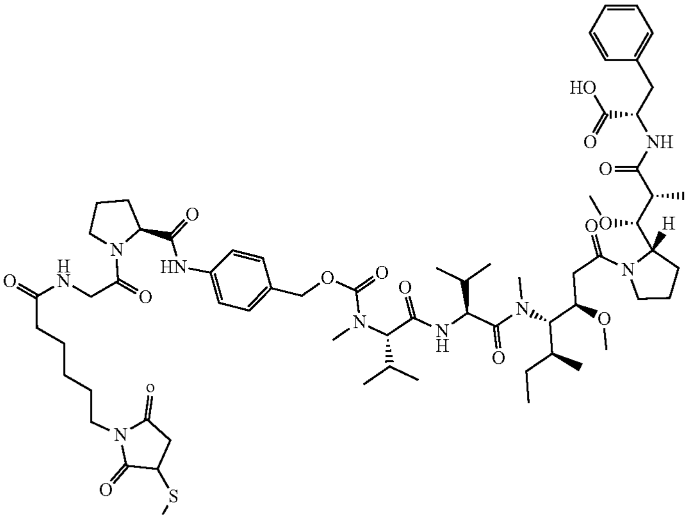
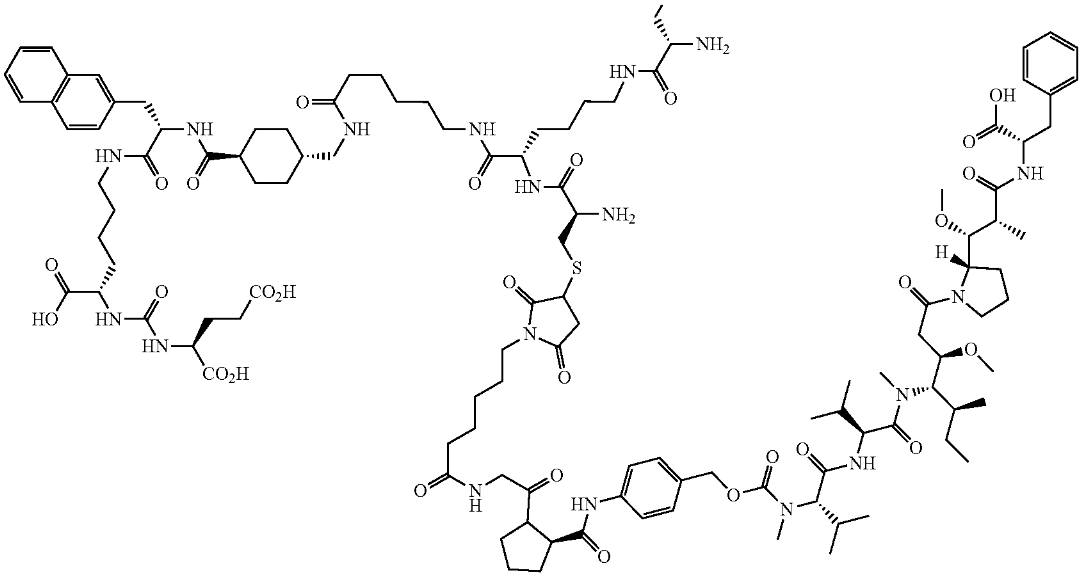
Conjugate 9
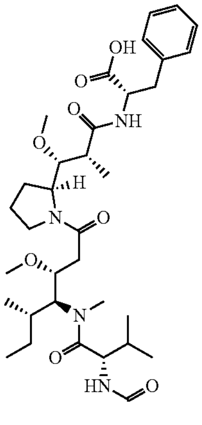

-continued

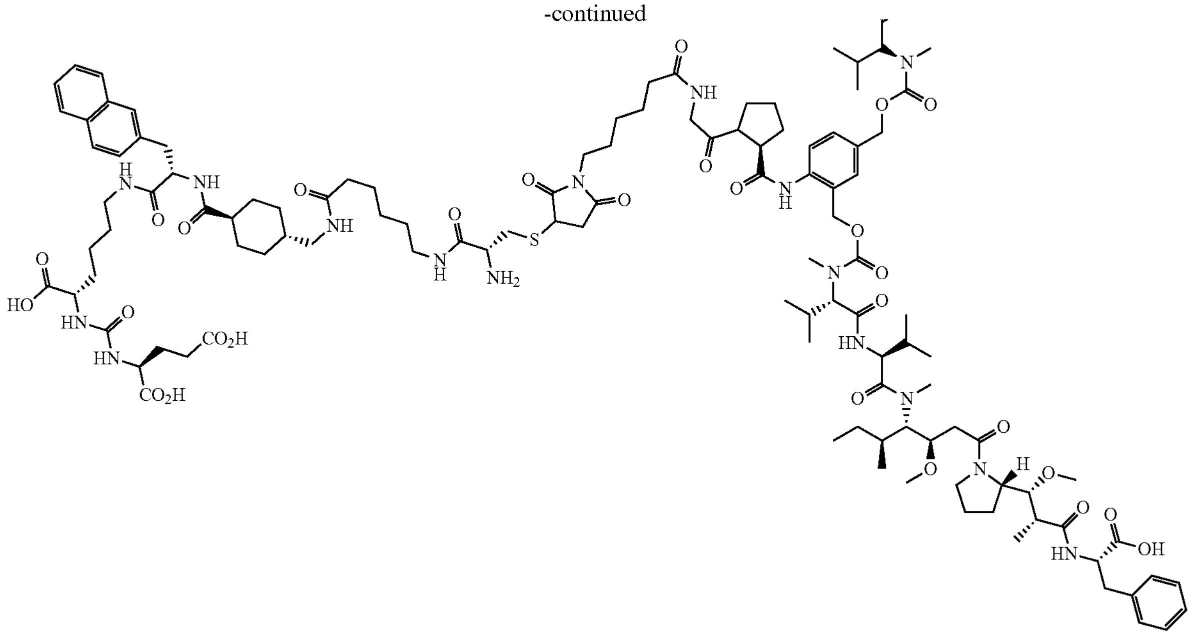

Conjugate 10

Conjugates 9 and 10 may be synthesized by analogous routes to those shown above.

Example 2—MMAE Release from Different Conjugates in LNCaP Tumor Model

Implantation of Subcutaneous Tumors

LNCaP tumor cells were grown to 80% confluence and detached with Trypsin-EDTA 0.05%. Cells were resuspended in PBS at a density of $30\times10^6$ cells/mL. The cell suspension was further diluted 1:1 with Matrigel. 200 µL of LNCaP cells ($3\times10^6$ cells) were injected subcutaneously in the left flank of female athymic Balb/c AnNRj-Foxn1 mice (6 to 8 weeks of age). Tumors were grown until volumes of 200-300 $mm^3$ were observed.

SMDC Injections and Organ Extraction 0.1 ml of 50 µM solutions (2% DMSO, PBS) of the four Conjugates (1-4) were injected intravenously into 4 of the mice (1 mouse per SMDC). The animals were sacrificed after 24 h and the following organs were extracted: blood, LNCaP tumor (PSMA+), heart, lungs, liver, kidney, spleen, stomach. The blood fraction was centrifuged, and the plasma (supernatant) was extracted. The organs were preserved at −80° C. before being used for further analysis.

Sample Preparation and MS Quantification

Frozen plasma or mouse tissues (~50 mg) were thawed and treated with 600 µL of an aqueous solution containing 95% acetonitrile (ACN), and 0.1% HCOOH were added to induce protein precipitation. 50 µL of a solution of d8-MMAE, 50 nM) was added as internal standard. Samples were then homogenized with a tissue lyser for 15 minutes at 30 Hz. After homogenization, samples were centrifuged (21'000 g for 10 minutes). The supernatant was collected and dried at room temperature with a rotary evaporator. Pellets were then resuspended in 1 mL of an aqueous solution containing 3% ACN and 0.1% of TFA and subsequently purified on Oasis HLB SPE columns. Eluates were dried under vacuum at room temperature. Dry pellets were resuspended in 0.4 mL of an aqueous solution containing 3% ACN and 0.1% of TFA and further purified using Macro-Spin SPE columns. Eluates were dried under reduced pressure at room temperature. Dry samples were finally resuspended in 30 µL of an aqueous solution containing 3% of ACN and 0.1% of HCOOH. Each sample (1.5 µL, 5% of the total) was then injected in the nanoLCHR-MS system. Chromatographic separation was carried out on a Acclaim PepMap RSLC column (50 µm×15 cm, particle size 2 µm, pore size 100 Å) with a gradient program from 95% A (0.1% HCOOH), 5% B (ACN, 0.1% HCOOH) to 5% A, 95% B in 45 minutes on an Easy nanoLC 1000. Sample clean-up and concentration was carried out on a Acclaim PepMAP 100 precolumn (75 µm×2 cm, particle size 3 µm, pore size 100 µm. The LC system was coupled to a QExactive mass spectrometer via a Nano Flex ion source. Ionization was carried out with 2 kV of spray voltage, 250° C. of capillary temperature, 60 S-lens RF level. The mass spectrometer was operating in targeted Single Ion Monitoring mode (t-SIM) following the molecular ion 718.5113 m/z. The detector was working in a positive ionization mode with the following parameters: resolution 70'000 (FWHM at 200 m/z); AGC target of $5\times10^4$; maximum injection time of 200 ms; isolation window 14 m/z; isolation offset 5 m/z. Peak areas of analytes and internal standards were integrated, and corresponding ratios were calculated. The ratios were then transformed into pmol/g of wet tissue using single-concentration external calibration points and corrected by the total weight of the sample analysed. The percentage of injected dose per gram (% ID/g) was finally calculated by normalizing the value based on the total dose injected into the mouse. Data analysis was carried out with Thermo Xcalibur Qual Browser v2.2

Results

FIG. 1A-D shows the quantitative biodistribution values of MMAE release 24 hours after intravenous injection of the four Conjugates. Significant release of MMAE was only seen with Conjugate 1. The release was contained with the LNCap tumour. There was almost no release of MMAE from the comparative Conjugates 2 to 4 which did not comprise Gly-Pro. The results were confirmed for Conjugate 1 and for Conjugate 2 when the experiment was repeated with three mice each (FIG. 1E-F).

Example 3—MMAE Release from Different Conjugates in HT1080.hPSMA Tumor Model

Implantation of Subcutaneous Tumors

HT1080.hPSMA tumor cells were grown to 90% confluence and detached with Trypsin-EDTA 0.05%. Cells were resuspended in Hank's Balanced Salt Solution (HBSS) at a density of $5\times10^7$ cells/mL. 100 μL of HT1080.hPSMA cells ($5\times10^6$ cells) were injected subcutaneously in the right flank of female athymic Balb/c AnNRj-Foxn1 mice (6 to 8 weeks of age). Tumors were grown until ~250 $mm^3$ volume (average).

SMDC Injections and Organ Extraction

Comparison study: 0.1 mL of 50 μM solutions (2% DMSO, PBS, 250 nmol/kg) of the four conjugates (1 to 4) were injected intravenously. The animals were sacrificed in groups of 3 after 24 h, and blood and the following organs were extracted: HT1080.hPSMA tumor, heart, lungs, liver, kidney, spleen, stomach. The blood fraction was centrifuged, and the plasma (supernatant) was extracted. The organs were stored at −80° C. before being used for further analysis.

Timepoint study: 0.1 mL of a 50 μM solution (2% DMSO, PBS, 250 nmol/kg) of conjugate 1 was injected intravenously into the tail vein of the mice. The animals were sacrificed in groups of 3 after 6 h, 24 h, 48 h, and 72 h, and blood and the following organs were extracted: HT1080.hPSMA tumor, heart, lungs, liver, kidney, spleen, stomach. The blood fraction was centrifuged, and the plasma (supernatant) was extracted. The organs were stored at −80° C. before being used for further analysis.

Sample Preparation and MS Quantification

Frozen plasma (50 μL) and mouse tissues (~50 mg) were thawed, and 500 μL of PBS was added. Samples were kept on ice, and 50 μL solution of internal standard ($d_8$-MMAE, 50 nM) was added. Samples were then homogenized at 4° C. with a tissue lyser for 2 minutes at 30 Hz for 4 cycles. After homogenization, samples were centrifuged (21'000 g, 10 min). Subsequently, 100 μL of supernatants were collected and added to 900 μL of acetonitrile (ACN) to induce protein precipitation. After centrifugation (21'000 g, 10 min), 800 μL of supernatants were collected and dried at room temperature with a vacuum centrifuge. Pellets were then resuspended in 20 μL of an aqueous solution containing 3% ACN and 0.1% of HCOOH, and 5 μL were injected into the UHPLC-MS system. Chromatographic separation was carried out on a Hypersil Gold C18 column (100 mm×2.1 mm, 1.9 μm particle size, 175 Å pore size) column temperature was set at 50° C. and a flow rate of 700 μL/min with a gradient program from 95% A (water+0.1% HCOOH), 5% B (ACN+0.1% HCOOH) to 35% of A in 2.5 minutes, from 35% A to 5% A in 0.4 minutes and 5% A was kept for 1.3 minutes before reconditioning at 95% A. The LC system was coupled to a Q-Exactive mass spectrometer via an Ion Max HESI Source. Ionization was carried out with a spray voltage of 3.5 kV; Sheath gas 40 units; Aux gas 10 units; capillary temperature of 380° C.; Aux gas temperature 450° C.; S-lens RF level 60. The mass spectrometer was operating in targeted Single Ion Monitoring mode (t-SIM) following the molecular ion 718.5113 m/z. The detector was working in positive ionization mode with the following parameters: resolution 70'000 (FWHM at 200 m/z); AGC target of $5\times10^4$; maximum injection time of 200 ms; isolation window 14 m/z; isolation offset 5 m/z. Peak areas of analytes and internal standards were integrated, and corresponding ratios were calculated. The ratios were then transformed into pmol/g of wet tissue using single-concentration external calibration points and corrected by the total weight of the sample analysed. The percentage of injected dose per gram (% ID/g) was finally calculated by normalizing the value based on the total dose injected into the mouse. Data analysis was performed with Skyline v22.2.0.351.

Results

Figure 3:
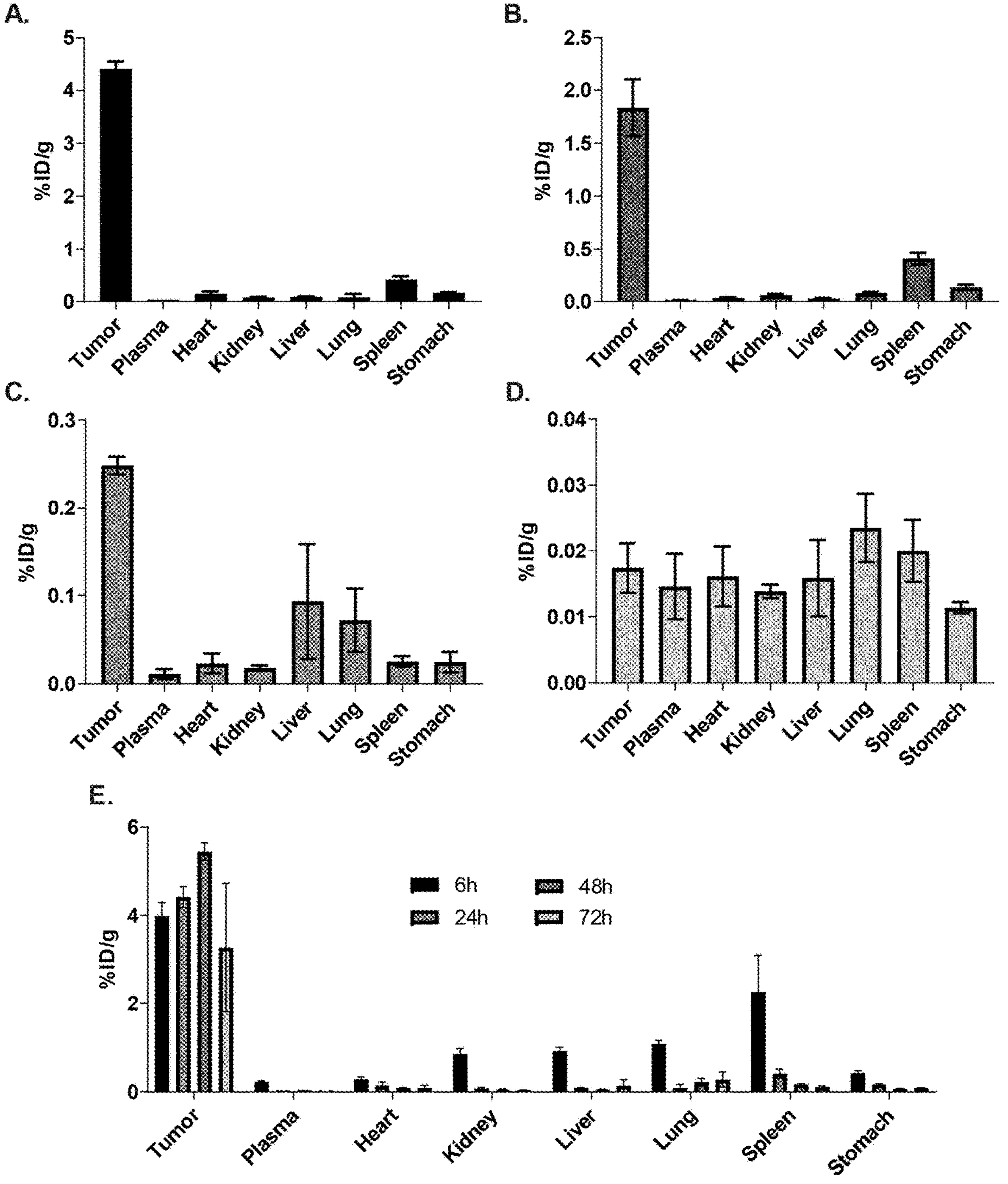
FIG. 3 shows the efficacy of in vivo drug release after systemic administration of a conjugate of the invention (Conjugate 1 (FIG. 3A)) and comparative Conjugates 2 (FIG. 3B), 3 (FIG. 3C) and 4 (FIG. 3D) in the HT1080.hPSMA tumor model.

FIGS. 3A to 3D show the quantitative biodistribution values of MMAE release 24 hours after intravenous injection of the four conjugates. The highest release of MMAE was observed with Conjugate 1 (4.5% ID/g) (FIG. 3A), followed by Conjugate 2 (1.7% ID/g) (FIG. 3B). In contrast, Conjugates 3 and 4 showed no significant release (<0.3% ID/g) (FIGS. 3C and 3D). The release was contained within the HT1080.hPSMA tumor.

There was significantly lower or no release of MMAE from the comparative Conjugates 2, 3 and 4.

Additionally, FIG. 3E shows a timepoint study of the MMAE release of Conjugate 1, which suggests stable payload accumulation in the tumors over an extended time.

Example 4—Comparative Therapeutic Experiments of Different Conjugates in HT1080.hPSMA Tumor Model Implantation of Subcutaneous Tumors HT1080.hPSMA tumor cells were grown to 90% confluence and detached with Trypsin-EDTA 0.05%. Cells were resuspended in Hank's Balanced Salt Solution (HBSS) at a $5\times10^7$ cells/mL density. 100 μL of HT1080.hPSMA cells ($5\times10^6$ cells) were injected subcutaneously in the right flank of female athymic Balb/c AnNRj-Foxn1 mice (6 to 8 weeks of age). Tumors were grown until volumes of −100 $mm^3$.

Schedule of Treatment

Tumor-bearing mice were randomized into groups of 5 and 0.1 mL of 50 μM solutions (2% DMSO, PBS, 250 nmol/kg) of the four conjugates (1 to 4), or saline solution (0.9% NaCl) was injected intravenously three times with 1-day break in between (days 8, 10, and 12 after tumor implantation).

Results

FIG. 4A describes the tumor volume change over the course of the therapy, outlining the contrasting therapeutic efficacy of Conjugates 1 to 4. Administration of Conjugate 1 was clearly superior as it led to significant shrinkage of the tumors of all 5 mice in the group and, ultimately, 1/5 complete remissions. The second best was Conjugate 2, which promoted a tumor growth retardation but did not lead to shrinkage of the tumor mass. In contrast, Conjugates 3 and 4 didn't display any therapeutic efficacy, as their growth pattern was similar to the saline negative control. These therapy results are in line with the MMAE payload release studies reported in Example 2 and Example 3 confirming that there is a direct correlation between MMAE release and the therapeutic performance of the conjugates.

FIG. 4B shows the body weight change (%) of the therapy groups associated with Conjugates 1-4 and the saline control. Conjugate 1 displayed the lowest toxicity compared to the other three conjugates of the invention (2-4).

Example 5—Payload Study and Combination Therapy in HT1080.hPSMA Tumor Model

Implantation of Subcutaneous Tumors

HT1080.hPSMA tumor cells were grown to 90% confluence and detached with Trypsin-EDTA 0.05%. Cells were resuspended in Hank's Balanced Salt Solution (HBSS) at a $5\times10^7$ cells/mL density. 100 μL of HT1080.hPSMA cells ($5\times10^6$ cells) were injected subcutaneously in the right flank of female athymic Balb/c AnNRj-Foxn1 mice (6 to 8 weeks of age). Tumors were grown until an average volumes of ~100 $mm^3$ was reached.

Schedule of Treatment

Tumor-bearing mice were randomized into groups of 3 or 4 animals. A 50 μM solution (2% DMSO, 250 nmol/kg; 100 μL) of Conjugate 1, 5, or 6, L19-IL2 (SEQ ID NO: 10, 0.5 mg/mL, 2.5 mg/kg; 100 μL), PBS (100 μL), or L19-IL2 buffer ($NaH_2PO_4$ 6.7 mM, NaCl 20 mM, KCl 1.8 mM, Mannitol 133 mM, Tween80 0.1% v/v, Glycerol 1% w/v; 100 μL) was injected intravenously (i.e., systemic administration through tail-vein) with the following schedule:

Groups of Conjugates 1, 5, or 6: two separate injections with a 3-day break in between (day 7 and day 11 after tumor implantation).

L19-IL2 group: three separate injections with a 1-day break in between (day 8, day 10, and day 12 after tumor implantation).

Combination therapy groups: two separate injections of Conjugate 1, 5, or 6 with a 3-day break in between (day 7 and day 11 after tumor implantation) and three separate injections of L19-IL2 with a 1-day break in between (day 8, day 10, and day 12 after tumor implantation).

Vehicle group: two separate injections of PBS with a 3-day break in between (day 7 and day 11 after tumor implantation) and three separate injections of L19-IL2 buffer with a 1-day break in between (day 8, day 10, and day 12 after tumor implantation).

Results

Figure 5:
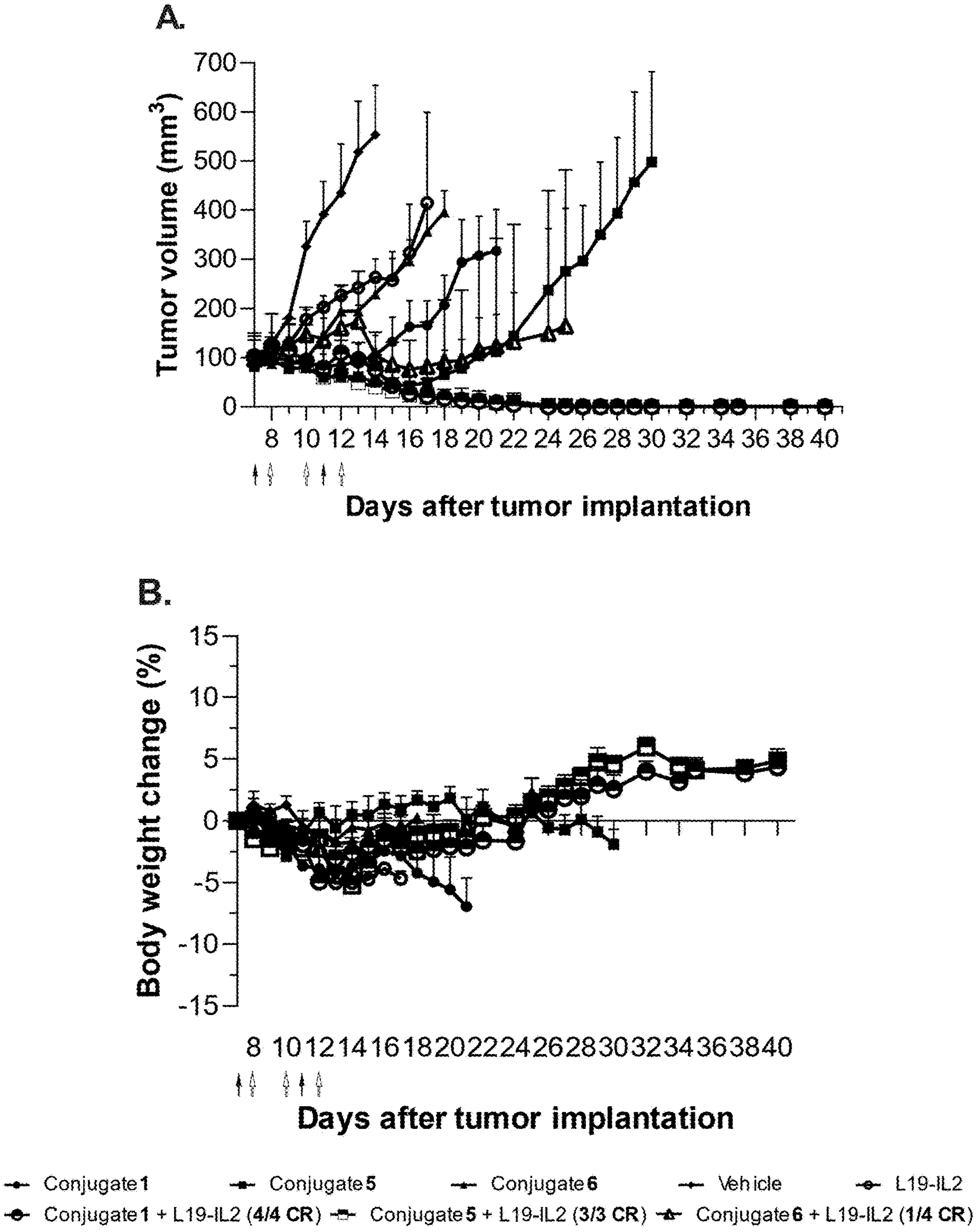
FIG. 5 shows the therapeutic efficacy of Conjugate 1, 5, or 6 (black arrows) and L19-IL2 (white arrows) in Balb/c nude mice bearing HT1080.hPSMA xenografts: Graph (A) compares the therapeutic activity of (i) single agents (Conjugates 1, 5, 6, and L19-IL2), (ii) combination of L19-IL2 with Conjugates 1, 5, 6, and (iii) vehicle group; and Graph (B) outlines the percentage change in body weight over the course of the experiment (n=3/4).

FIG. 5A presents changes in tumor volume over the course of the combination therapy, outlining the therapeutic efficacy of the different conjugates and their synergy with L19-IL2. Monotherapy with Conjugate 5 proved to be the best, leading to the highest and prolonged in vivo anti-tumor activity. Conjugate 1 showed slightly lower anti-cancer efficacy as compared to Conjugate 5. Conjugate 6 showed significantly worse in vivo anti-tumor activity compared to both Conjugates 1 and 5. No cures were observed in the single-agent groups, as the utilized dosing schedule was diluted in order to highlight the potentiating effect of the L19-IL2 combination. All animals in the Conjugate 1+L19-IL2 and the Conjugate 5+L19-IL2 groups displayed complete responses (durable cancer cures) while only one out of 4 mice in the Conjugate 6+L19-IL2 was cured. By contrast, treatment with L19-IL2 monotherapy showed only a slight tumor growth retardation.

FIG. 5B presents body weight changes (%) of the therapy groups associated with single agent (Conjugates 1, 5, 6, or L19-IL2), combination of SMDCs+L19-IL2, and the vehicle-treated groups. No significant signs of toxicity were observed in the different treatment arms (no body weight loss observed).

Example 6—MMAE Release from Conjugate 7

Implantation of Subcutaneous Tumors

HT1080.hPSMA tumor cells were grown to 90% confluence and detached with Trypsin-EDTA 0.05%. Cells were resuspended in Hank's Balanced Salt Solution (HBSS) at a $5\times10^7$ cells/mL density. 100 μL of HT1080.hPSMA cells ($5\times10^6$ cells) were injected subcutaneously in the right flank of female athymic Balb/c AnNRj-Foxn1 mice (6 to 8 weeks of age). Tumors were grown until ~250 $mm^3$ volume (average).

SMDC Injections and Organ Extraction 0.1 mL of a 50 μM solution (2% DMSO, PBS, 250 nmol/kg) of Conjugate 7 was injected intravenously into the tail vein of the mice. The animals were sacrificed after 6 h, 24 h, 48 h, or 72 h (n=3/group), and blood and the following organs were extracted: HT1080.hPSMA tumor, heart, lungs, liver, kidney, spleen, stomach. The blood fraction was centrifuged, and the plasma (supernatant) was extracted. The organs were stored at −80° C. before being used for further analysis.

Sample Preparation and MS Quantification

Frozen plasma (50 μL) and mouse tissues (~50 mg) were thawed, and 500 μL of PBS was added. Samples were kept on ice, and 50 μL solution of internal standard ($d_8$-MMAE, 50 nM) was added. Samples were then homogenized at 4° C. with a tissue lyser for 2 minutes at 30 Hz for 4 cycles. After homogenization, samples were centrifuged (21'000 g, 10 min). Subsequently, 100 μL of supernatants were collected and added to 900 μL of acetonitrile (ACN) to induce protein precipitation. After centrifugation (21'000 g, 10 min), 800 μL of supernatants were collected and dried at room temperature with a vacuum centrifuge. Pellets were then resuspended in 20 μL of an aqueous solution containing 3% ACN and 0.1% of HCOOH, and 5 μL were injected into the UHPLC-MS system. Chromatographic separation was carried out on a Hypersil Gold C18 column (100 mm×2.1 mm, 1.9 μm particle size, 175 Å pore size) column temperature was set at 50° C. and a flow rate of 700 μL/min with a gradient program from 95% A (water+0.1% HCOOH), 5% B (ACN+0.1% HCOOH) to 35% of A in 2.5 minutes, from 35% A to 5% A in 0.4 minutes and 5% A was kept for 1.3 minutes before reconditioning at 95% A. The LC system was coupled to a Q-Exactive mass spectrometer via an Ion Max HESI Source. Ionization was carried out with a spray voltage of 3.5 kV; Sheath gas 40 units; Aux gas 10 units; capillary temperature of 380° C.; Aux gas temperature 450° C.; S-lens RF level 60. The mass spectrometer was operating in targeted Single Ion Monitoring mode (t-SIM) following the molecular ion 718.5113 m/z. The detector was working in positive ionization mode with the following parameters: resolution 70'000 (FWHM at 200 m/z); AGC target of $5\times10^4$; maximum injection time of 200 ms; isolation window 14 m/z; isolation offset 5 m/z. Peak areas of analytes and internal standards were integrated, and corresponding ratios were calculated. The ratios were then transformed into pmol/g of wet tissue using single-concentration external calibration points and corrected by the total weight of the sample analysed. The percentage of injected dose per gram (% ID/g) was finally calculated by normalizing the value based on the total dose injected into the mouse. Data analysis was performed with Skyline v22.2.0.351.

Figure 6:
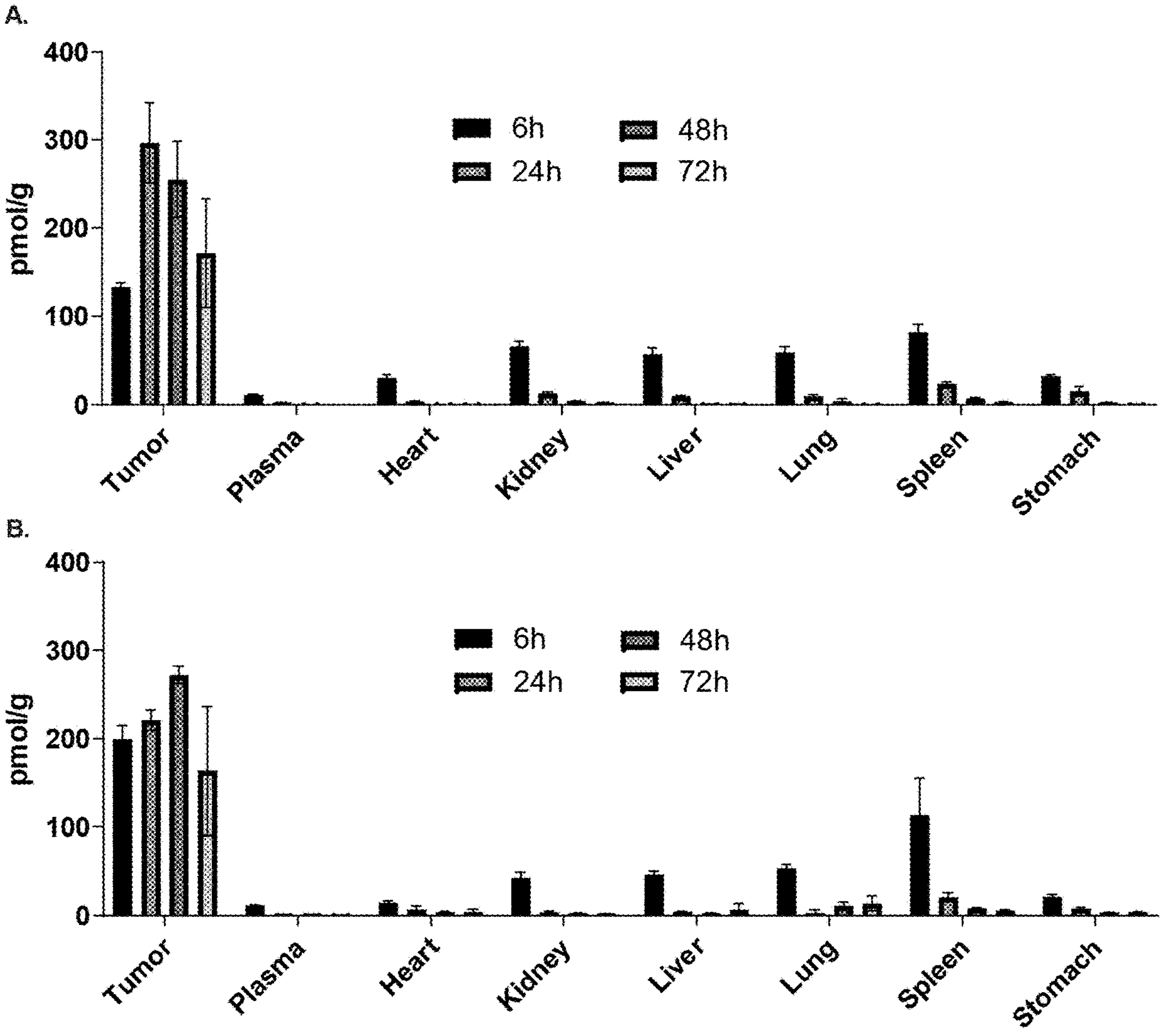
FIG. 6 shows the in vivo MMAE release in the HT1080.hPSMA tumor model after systemic administration of Conjugate 7 (FIG. 6A) and Conjugate 1 (FIG. 6B) at different time points (6 h, 24 h, 48 h, 72 h) (n=3).

FIG. 6A shows the quantitative biodistribution values of MMAE release 6 h, 24 h, 48 h, and 72 h after intravenous injection of Conjugate 7. FIG. 6B shows the quantitative biodistribution values of MMAE release 6 h, 24 h, 48 h, and 72 h after intravenous injection of Conjugate 1. The highest accumulation point was observed at 24 h, with an average pmol/g of approx. 300. The respective values for 48 h and 72 h were comparable for both conjugates, while Conjugate 1 had higher release at 6 h (200 pmol/g vs 133 pmol/g).

REFERENCES

A number of publications are cited above in order to more fully describe and disclose the invention and the state of the art to which the invention pertains. Full citations for these references are provided below. The entirety of each of these references is incorporated herein.

| | Reference | Doi |
|---|---|---|
| Edosada 2006 | Edosada, C, et al., Enzyme Catalysts and Regulation, 281(11), 7437-7444, 2006 | 10.1074/jbc.M511112200 |
| Fattorusso 1999 | Fattorusso, R, et al., (1999) *Structure*, 7, 381-390 | 10.1016/S0969-2126(99)80051-3 |
| Israeli 1993 | Israeli, R, et al., Cancer Research 53, 227-233, 1993 | ISSN: 1538-7445 |
| Neri 1995 | Neri, D, et al., (1995) J Mol Biol, 246, 367-373 | 10.1006/jmbi.1994.0091 |
| Sartor 2021 | Sartor, O, et al., N Engl J Med 2021; 385: 1091-1103 | 10.1056/NEJMoa2107322 |
| Scher 2015 | Scher HI, et al., PLoS One. 2015 Oct. 13; 10(10): e039440 | 10.1371/journal.pone.0139440 |
| Sung 2021 | Sung H, et al., CA Cancer J Clin. 2021 May; 71(3): 209-249 | 10.3322/caac.21660 |

Statements

1. A conjugate of Formula I:

Formula I

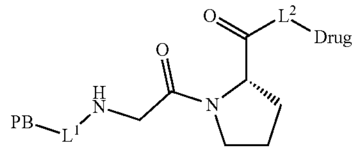

Gly-Pro or a pharmaceutically acceptable salt thereof, wherein:

PB is a PSMA binding moiety which has a molecular weight of below 1000 Da;

$L^1$ is a linker covalently attaching PB to Gly-Pro, said linker being a saturated or a partially or fully unsaturated framework comprising C and H atoms and at least one heteroatom, wherein said framework has end points of attachment 'a' and 'b' and a length between 6 and 30 atoms (via the shortest path between PB and Gly-Pro) between 'a' and 'b'; wherein said framework may include one or more straight and/or branched chains and/or rings and is optionally substituted on any available C atom(s) by one or more F;

$L^2$ is a either a single bond or a self-immolative linker; and

Drug is a cytotoxic agent linked to Gly-Pro.

2. The conjugate according to statement 1, wherein PB is of formula II:

Formula II

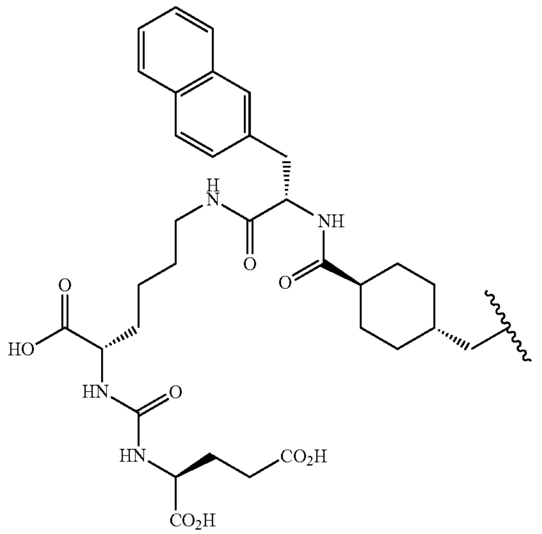

wherein the wavy bond represents a point of attachment to linker $L^1$.

3. The conjugate according to either statement 1 or statement 2, wherein $L^2$ is a self-immolative linker.
4. The conjugate according to statement 3, wherein the self-immolative linker is para-aminobenzyloxycarbonyl.
5. The conjugate according to statement 3, wherein the self-immolative linker is derived from (4-amino-1,3-phenylene)dimethanol.
6. The conjugate according to any one of statements 1 to 5, wherein Drug is selected from the group consisting of: an auristatin, a camptothecin, a DNA minor groove binding agent, a DNA minor groove alkylating agent, an enediyne, a lexitropsin, a duocarmycin, a taxane, a puromycin, a dolastatin, a maytansinoid and a vinca alkaloid.

7. The conjugate according to statement 6, wherein Drug is a camptothecin.

8. The conjugate according to statement 7, wherein Drug is exatecan having the following structure:

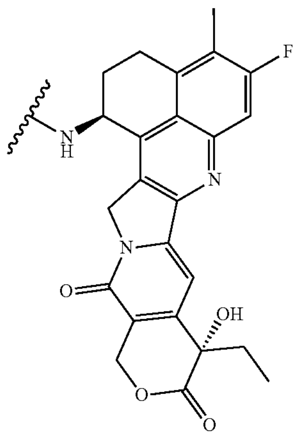

Exatecan wherein the wavy bond represents a point of attachment to linker $L^2$.

9. The conjugate according to statement 6, wherein Drug is an auristatin.

10. The conjugate according to statement 9, wherein Drug is monomethyl auristatin E having the following structure:

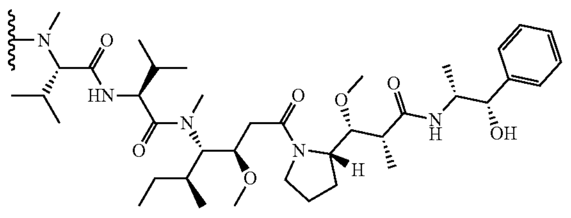

MMAE wherein the wavy bond represents a point of attachment to linker $L^2$

11. The conjugate according to statement 9, wherein Drug is monomethyl auristatin F having the following structure:

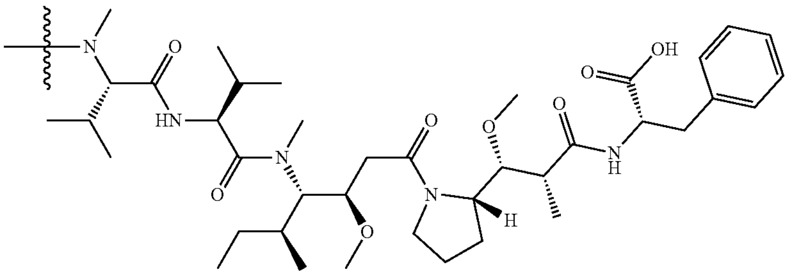

MMAF wherein the wavy bond represents a point of attachment to linker $L^2$.

12. The conjugate according to any one of statements 1 to 11, wherein $L^1$ is a saturated or partially unsaturated framework.

13. The conjugate according to any one of statements 1 to 12, wherein $L^1$ comprises C and H atoms and at least two heteroatoms.

14. The conjugate according to any one of statements 1 to 13, wherein $L^1$ comprises C and H atoms and at least one N heteroatom.

15. The conjugate according to any one of statements 1 to 14, wherein $L^1$ comprises C and H atoms and at least two heteroatoms.

16. The conjugate according to any one of statements 1 to 15, wherein $L^1$ comprises C and H atoms and at least four heteroatoms.

17. The conjugate according to any one of statements 1 to 16, wherein $L^1$ comprises C and H atoms and at least six heteroatoms.

18. The conjugate according to any one of statements 1 to 17, wherein $L^1$ comprises C and H atoms and at least two N heteroatoms, at least two O heteroatoms and at least one S heteroatom.

19. The conjugate according to any one of statements 1 to 18, wherein the framework of $L^1$ includes from 1 to 12 heteroatoms.

20. The conjugate according to any one of statements 1 to 19, wherein the framework of $L^1$ includes from 2 to 12 heteroatoms.

21. The conjugate according to any one of statements 1 to 20, wherein the framework of $L^1$ includes from 4 to 12 heteroatoms.

22. The conjugate according to any one of statements 1 to 21, wherein $L^1$ has a minimum length from 8 to 26 atoms between ‘a’ and ‘b’.

23. The conjugate according to any one of statements 1 to 22, wherein the total number of C and hetero atoms in $L^1$ is from 8 to 30.

24. The conjugate according to any one of statements 1 to 23, wherein the total number of C and hetero atoms in $L^1$ is from 10 to 28 or 14 to 70.

25. The conjugate according to any one of statements 1 to 24, wherein the framework of $L^1$ includes one or more straight and/or branched chains and/or rings (wherein the total number of branches is from 0 to 7) that are optionally substituted on any available C atom(s) by one or more F.

26. The conjugate according to any one of statements 1 to 25, wherein the framework of $L^1$ includes one or more straight and/or branched chains and/or rings (wherein the total number of branches is from 3 to 7) that are optionally substituted on any available C atom(s) by one or more F.

27. The conjugate according to any one of statements 1 to 26, wherein the framework of $L^1$ includes one or more straight and/or branched chains and/or rings (wherein the total number of branches is 5 to 7) that are optionally substituted on any available C atom(s) by one or more F.

28. The conjugate according to statement 27, wherein the total number of branches is 6.

29. The conjugate according to any one of statements 1 to 28, wherein the branches are selected from $NH_2$ and =O.

30. The conjugate according to any one of statements 1 to 29, wherein the total number of branches is 6, 5 branches consist of =O and 1 branch consists of $NH_2$.

31. The conjugate according to any one of statements 1 to 24, wherein the framework of $L^1$ includes one or more straight and/or branched chains and/or rings (wherein the total number of branches is from 0 to 14) that are optionally substituted on any available C atom(s) by one or more F.

32. The conjugate according to any one of statements 1 to 24 and 31, wherein the framework of $L^1$ includes one or more straight and/or branched chains and/or rings (wherein the total number of branches is from 6 to 14) that are optionally substituted on any available C atom(s) by one or more F.

33. The conjugate according to any one of statements 1 to 24, 31 and 32, wherein the framework of $L^1$ includes one or more straight and/or branched chains and/or rings (wherein the total number of branches is 10 to 14) that are optionally substituted on any available C atom(s) by one or more F.

34. The conjugate according to statement 33, wherein the total number of branches is 12.

35. The conjugate according to any one of statements 1 to 24 and 31 to 34, wherein the branches are selected from $NH_2$ and =O.

36. The conjugate according to any one of statements 1 to 24 and 31 to 35, wherein the total number of branches is 12, 10 branches consist of =O and 2 branches consist of $NH_2$.

37. The conjugate according to any one of statements 1 to 36, wherein a ring in the framework of $L^1$ comprises one or two heteroatoms.

38. The conjugate according to statement 37, wherein the heteroatoms in the ring are selected from N and O.

39. The conjugate according to statement 37, wherein the heteroatoms in the ring are N.

40. The conjugate according to any one of statements 1 to 39, wherein the framework of $L^1$ comprises a single ring.

41. The conjugate according to any one of statements 1 to 39, wherein the framework of $L^1$ comprises a single ring with a single N heteroatom.

42. The conjugate according to any one of statements 1 to 41, wherein the framework of $L^1$ comprises one or more functional groups selected from:

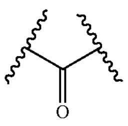

Carbonyl

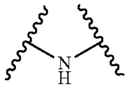

Amino

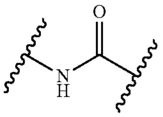

Amide

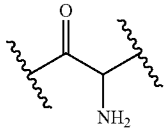

α-amino ketone

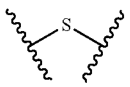

Thio

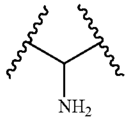

Amine

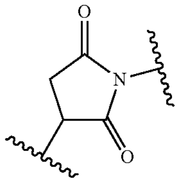

Succinimidyl

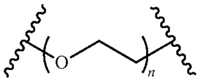

Ethylene glycol
(n = 1 to 6)

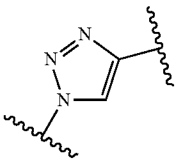

or

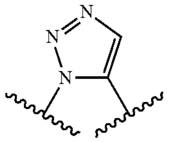

1,2,3-Triazole

43. The conjugate according to any one of statements 1 to 41, wherein $L^1$ is of Formula III:

$^{PB}$-($L^1$-1)-($L^1$-2)-($L^1$-3)-* Formula III wherein $^{PB}$- represents the point of attachment to moiety PB; and -* represents the point of attachment to Gly-Pro;

wherein together the groups $L^1$-1, $L^1$-2 and $L^1$-3 form a linker framework.

44. The conjugate according to statement 43, wherein $L^1$-1 is of formula IV:

Formula IV

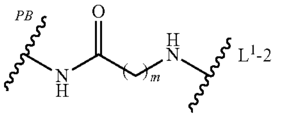

wherein m is 1 to 6.

45. The conjugate according to statement 44, wherein m is 5.

46. The conjugate according to any one of statements 43 to 45, wherein $L^1$-2 is:

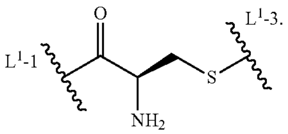

47. The conjugate according to any one of statements 43 to 45, wherein $L^1$-2 is:

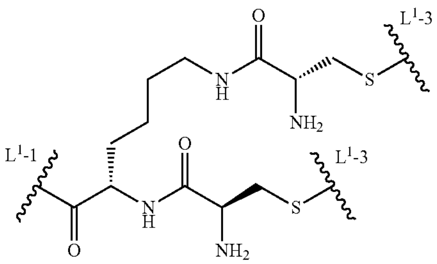 [SMILES: *SC[C@@H](N)C(=O)N[C@@H](CCCCNC(=O)[C@@H](N)CS*)C(*)=O]

$L^1$-1 represents the point of attachment to $L^1$-1; and each $L^1$-3 represents the point of attachment to each $L^1$-3.

48. The conjugate according to any one of statements 43 to 47, wherein $L^1$-3 is of formula V:

Formula V

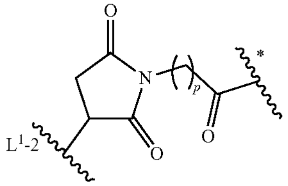

wherein p is 1 to 6 and

* represents the point of attachment to Gly-Pro.

49. The conjugate according to statement 48, wherein p is 5.

50. The conjugate according to statement 43, wherein $L^1$ is $L^1$-4:

$L^1$-4

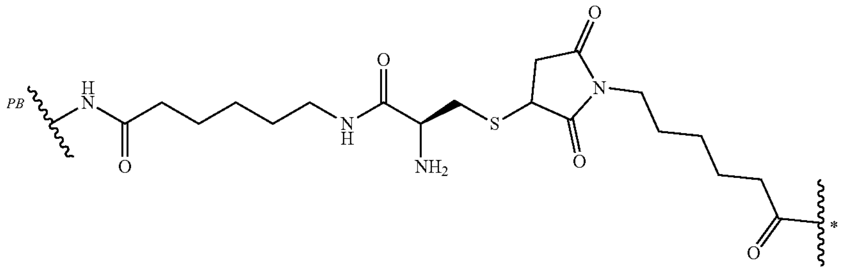

51. The conjugate according to statement 43, wherein $L^1$ is $L^1$-5:

$L^1$-5

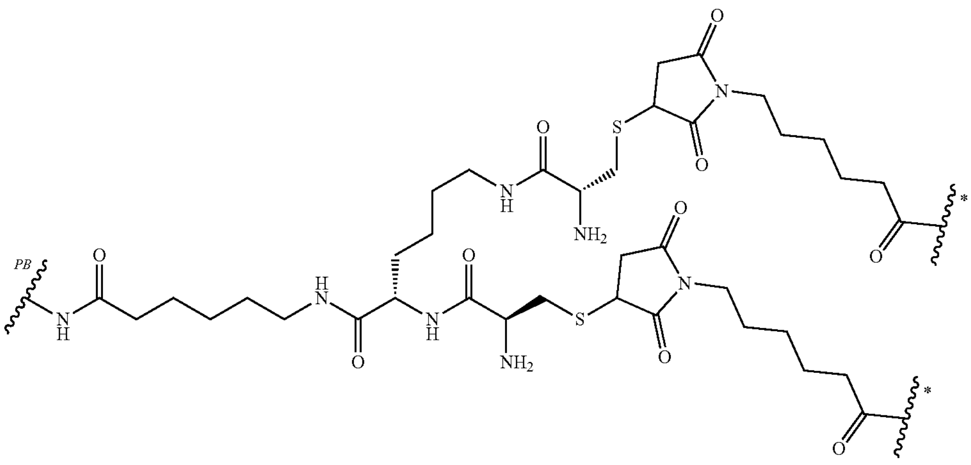

52. The conjugate according to statement 1, which is:
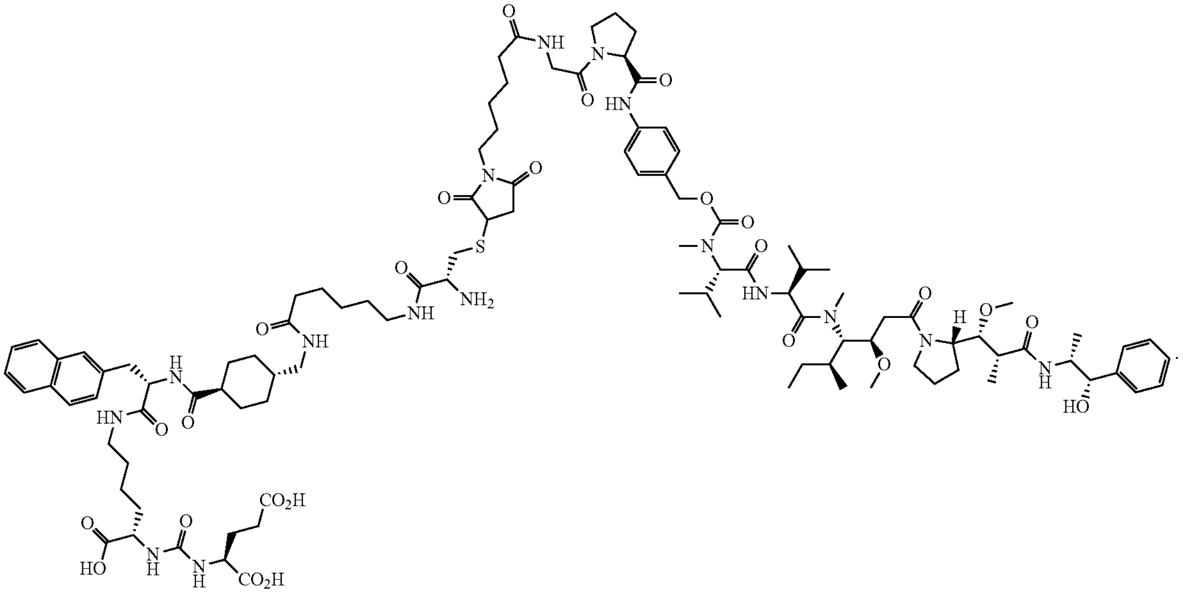
53. The conjugate according to statement 1, which is:
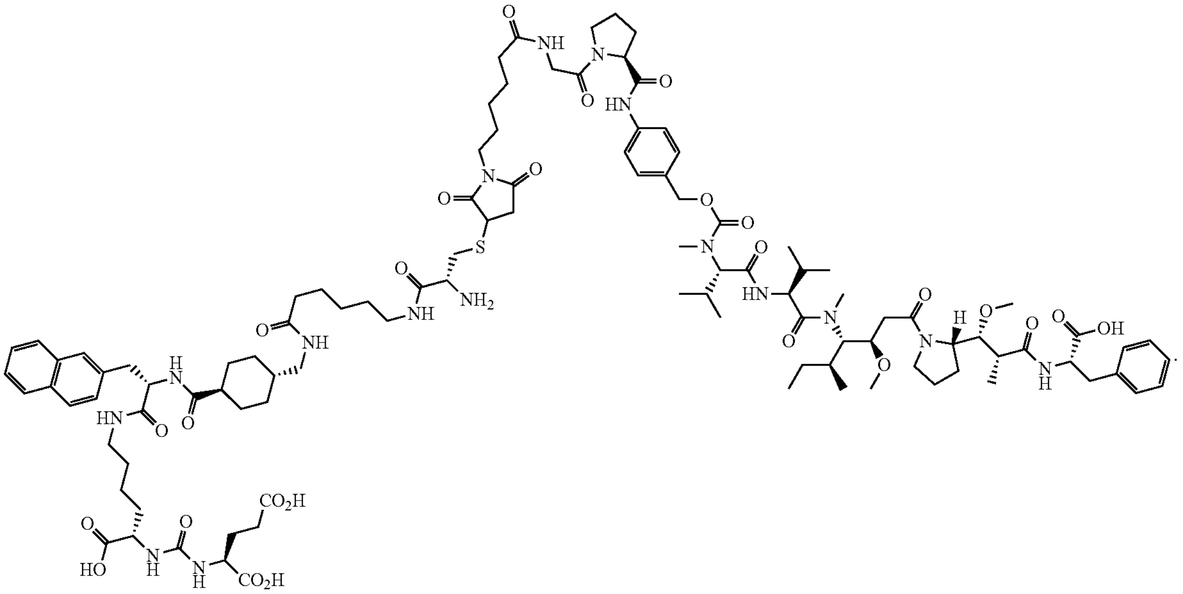

54. The conjugate according to statement 1, which is:
6
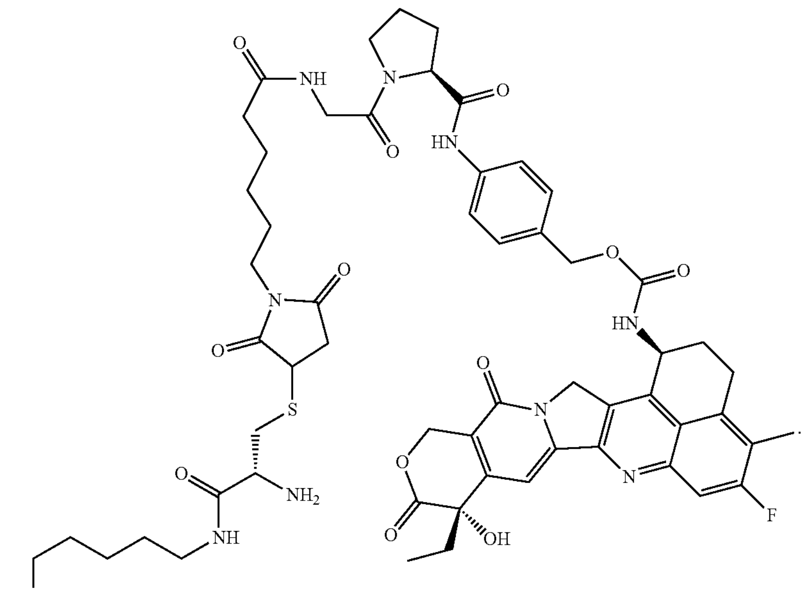
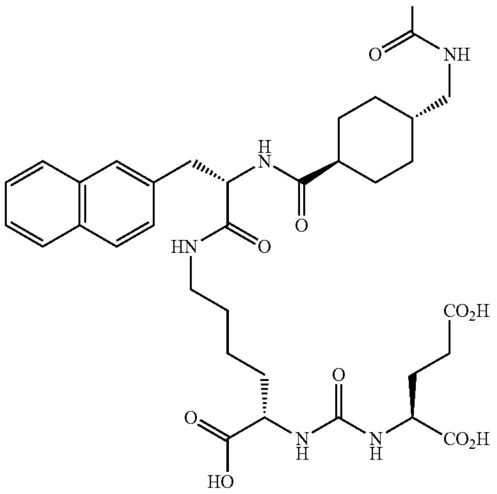

55. The conjugate according to statement 1, which is:

7

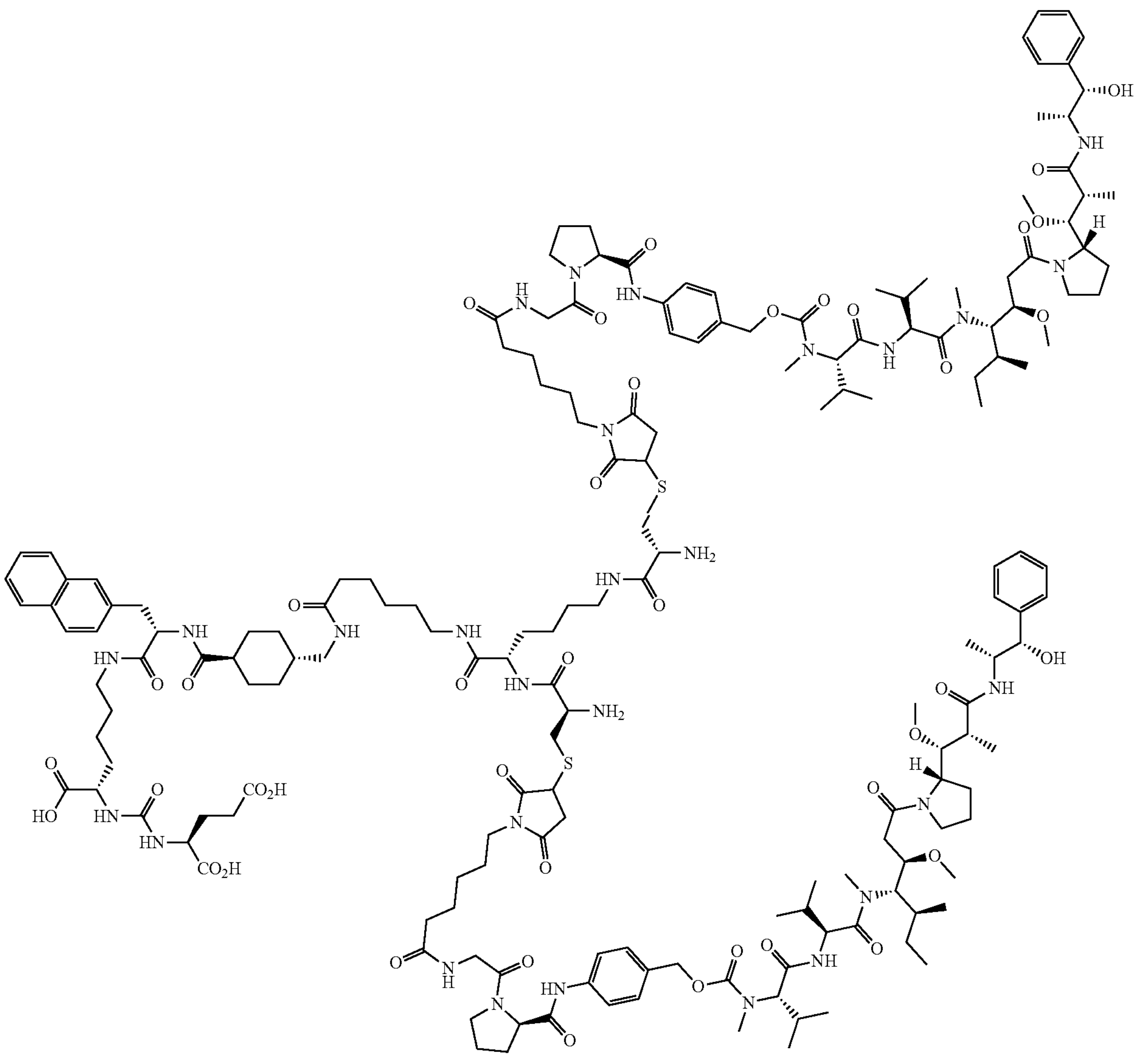

56. A pharmaceutical composition comprising the conjugate according to any one of statements 1 to 55 and a pharmaceutically acceptable excipient.

57. The conjugate according to any one of statements 1 to 55 or the pharmaceutical composition according to statement 56 for use in a method for treatment of the human or animal body.

58. The conjugate according to any one of statements 1 to 55 or the pharmaceutical composition according to statement 56 for use in a method or treatment or prophylaxis of a subject suffering from or having risk for malignancies characterized by PSMA overexpression.

59. The conjugate or the pharmaceutical composition for use according to statement 58, wherein the malignancy characterized by PSMA overexpression is prostate cancer, including metastatic prostate cancer, hormone sensitive prostate cancer (HSPC), and castration resistant prostate cancer (CRPC).

60. The conjugate or the pharmaceutical composition for use according to either statement 58 or statement 59, wherein said treatment or prophylaxis comprises the separate, sequential or simultaneous administration of i) said medicament comprising said conjugate of Formula I, or a pharmaceutically acceptable salt thereof, and ii) a therapeutic agent.

61. The conjugate or the pharmaceutical composition for use according to statement 60, wherein the therapeutic agent is an immunocytokine, such as an immunocytokine comprising a sequence having IL2 activity.

62. A method for treatment therapy or prophylaxis of malignancies characterized by PSMA overexpression comprising administering a therapeutically effective amount of the conjugate according to any one of statements 1 to 55 or the pharmaceutical composition according to statement 56 to a subject suffering from or having risk for said disease or disorder.

63. The method of statement 62, wherein the malignancy characterized by PSMA overexpression is prostate cancer, including metastatic prostate cancer, hormone sensitive prostate cancer (HSPC), and castration resistant prostate cancer (CRPC).
64. The method of either statement 62 or statement 63, wherein the method comprises administering to the subject a first amount of a conjugate of Formula I or a pharmaceutically acceptable salt thereof, and a second amount of a therapeutic agent.
65. The method of statement 64, wherein the therapeutic agent is an immunocytokine, such as an immunocytokine comprising a sequence having IL2 activity.
66. The use of a conjugate according to any one of statements 1 to 55 in the manufacture of a medicament for the treatment or prophylaxis of malignancies characterized by PSMA overexpression.
67. The use of statement 66, wherein the malignancy characterized by PSMA overexpression is prostate cancer, including metastatic prostate cancer, hormone sensitive prostate cancer (HSPC), and castrate resistant prostate cancer (CRPC).
68. The use of either statement 66 or statement 67, wherein said treatment or prophylaxis comprises the separate, sequential or simultaneous administration of i) said medicament comprising said conjugate of Formula I, or a pharmaceutically acceptable salt thereof, and ii) a therapeutic agent.
69. The use of statement 68, wherein the therapeutic agent is an immunocytokine, such as an immunocytokine comprising a sequence having IL2 activity.

The invention claimed is:

1. A conjugate of Formula I:

Formula I

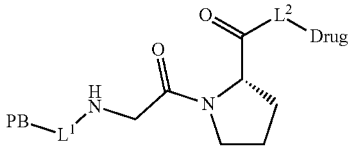

Gly-Pro or a pharmaceutically acceptable salt thereof, wherein:

PB is a PSMA binding moiety of Formula II:

Formula II

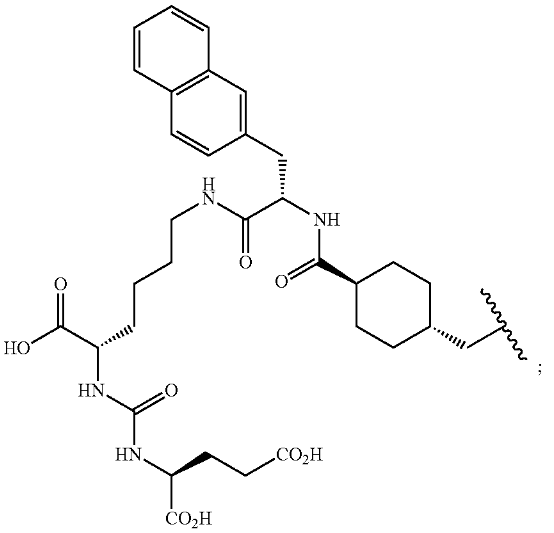

;

$L^1$ is a linker covalently attaching PB to Gly-Pro, said linker being $L^1$-4 or $L^1$-5:

$L^1$-4

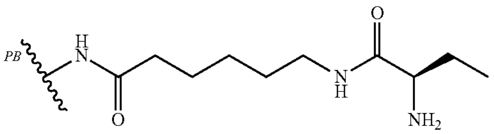

-continued

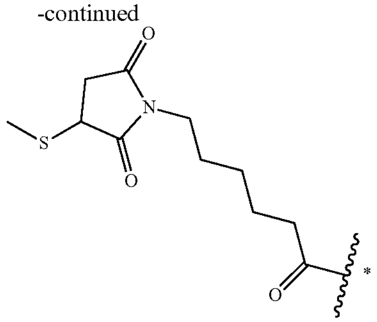

$L^1$-5

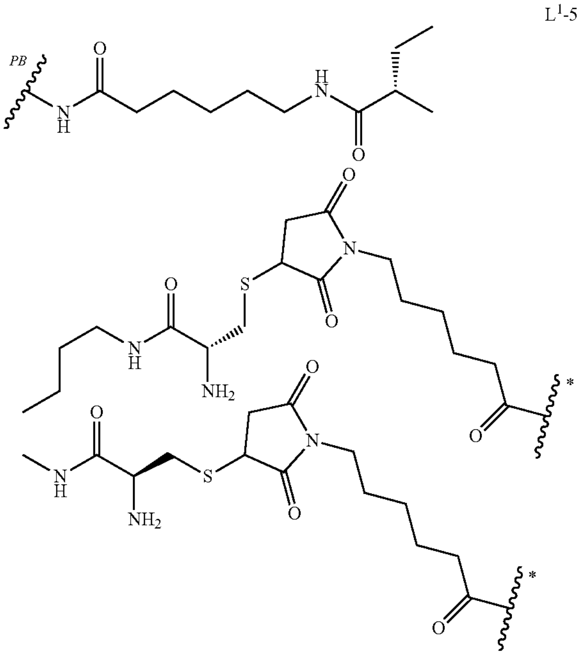

wherein * connects to N of the glycine in the Formula I;

$L^2$ is a self-immolative linker with the structure:

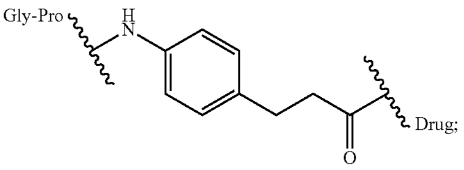 [SMILES: *Nc1ccc(CCC(*)=O)cc1]

and

Drug is a cytotoxic agent linked to Gly-Pro.

2. The conjugate according to claim 1, wherein Drug is selected from the group consisting of: auristatins, camptothecins, DNA minor groove binding agents, DNA minor groove alkylating agents, enediynes, lexitropsins, duocarmycins, taxanes, puromycins, dolastatins, maytansinoids and vinca alkaloids.

3. The conjugate according to claim 2, wherein Drug is exatecan having the following structure:

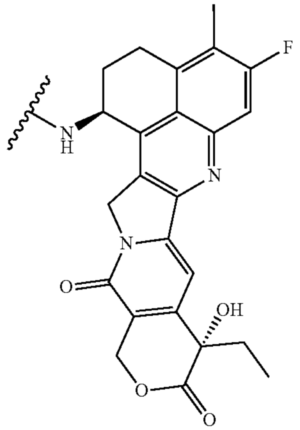

Exatecan wherein the wavy bond represents a point of attachment to linker $L^2$.

4. The conjugate according to claim 2, wherein Drug is monomethyl auristatin E having the following structure:

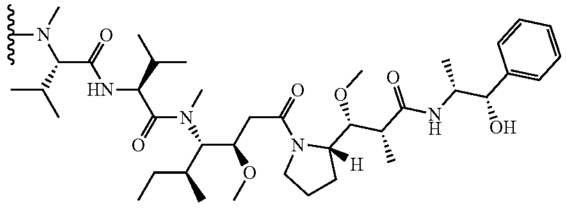

MMAE or monomethyl auristatin F having the following structure:

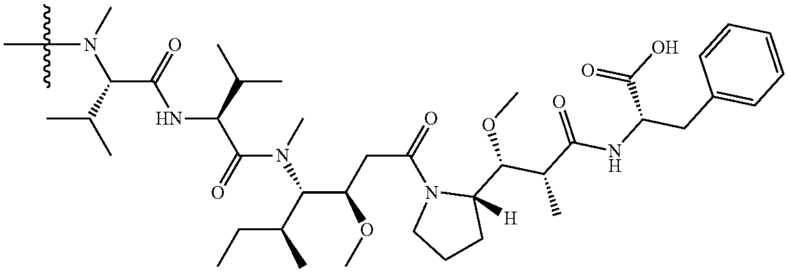

MMAF wherein the wavy bond represents a point of attachment to linker $L^2$.

5. The conjugate according to claim 1, which is 1, 5, 6 or 7:

1
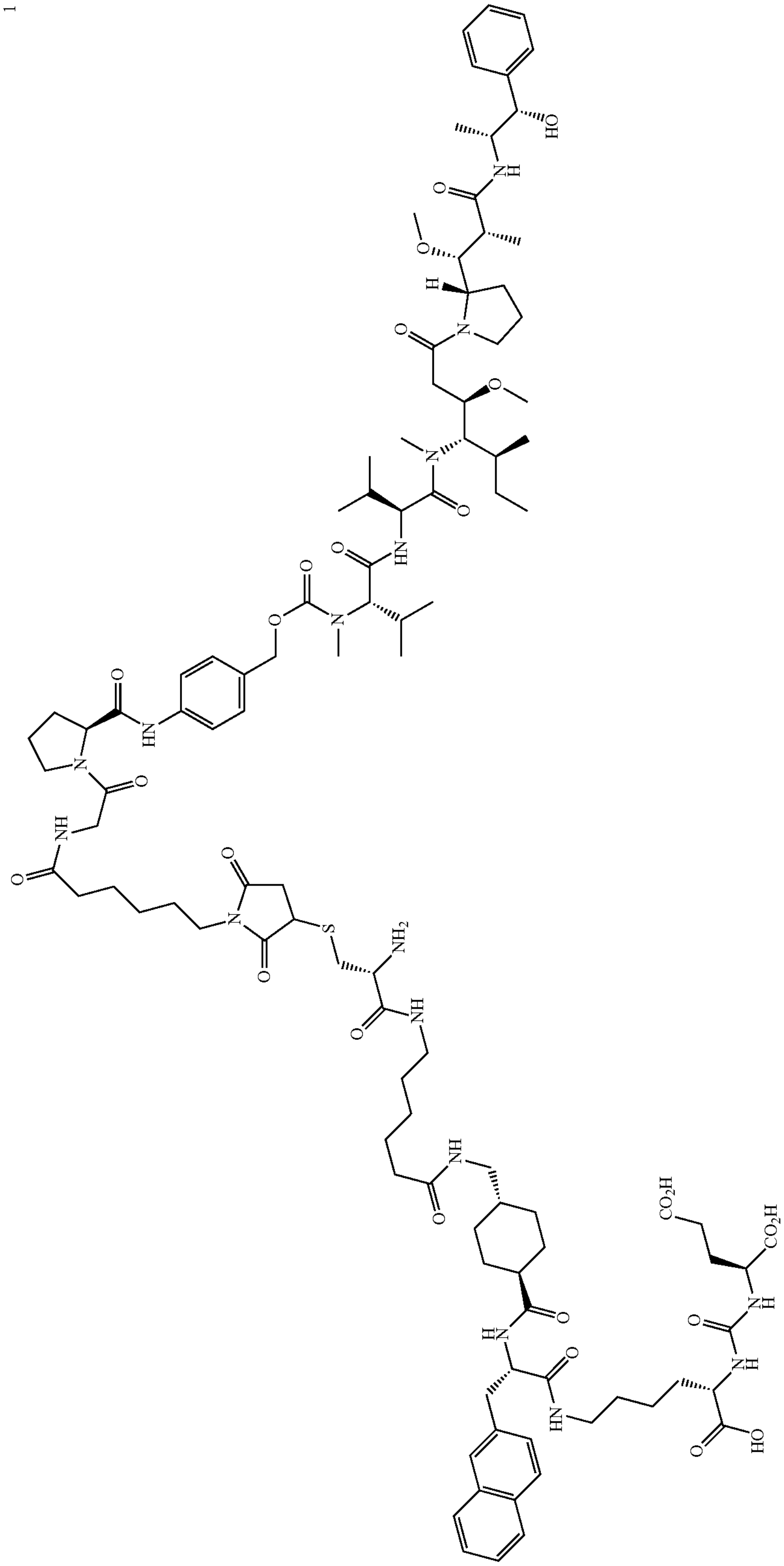

-continued
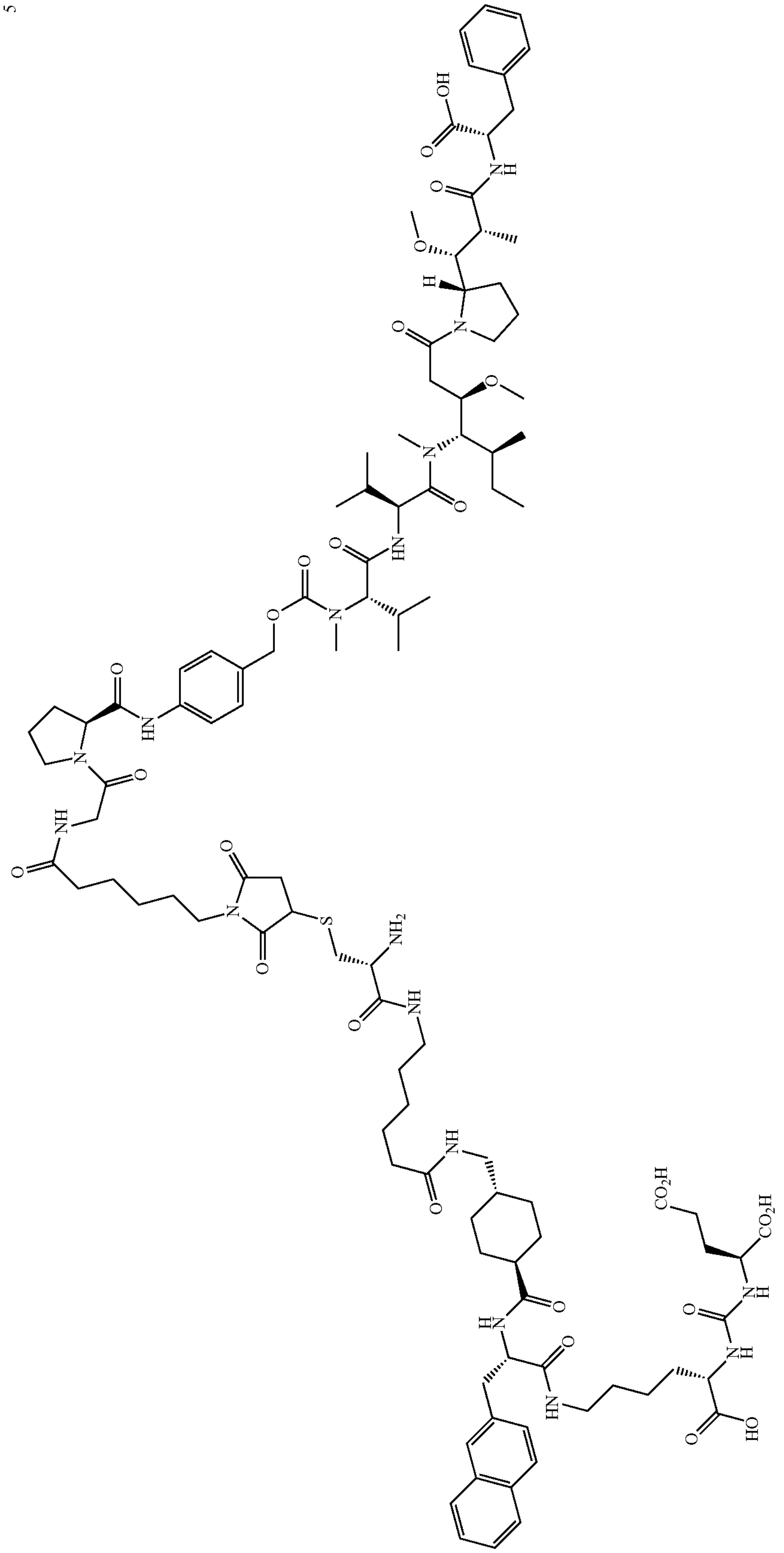

6
-continued
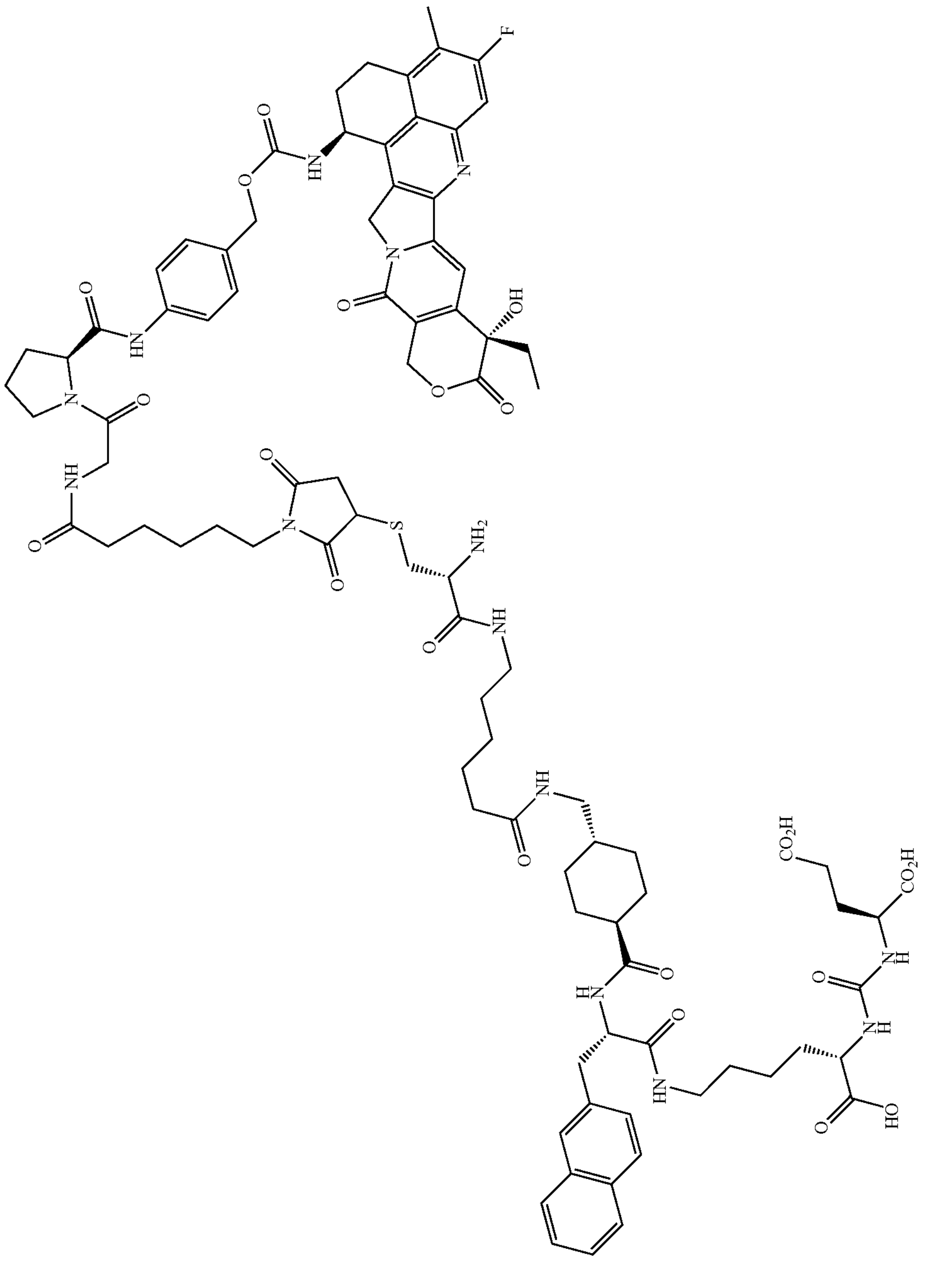

-continued
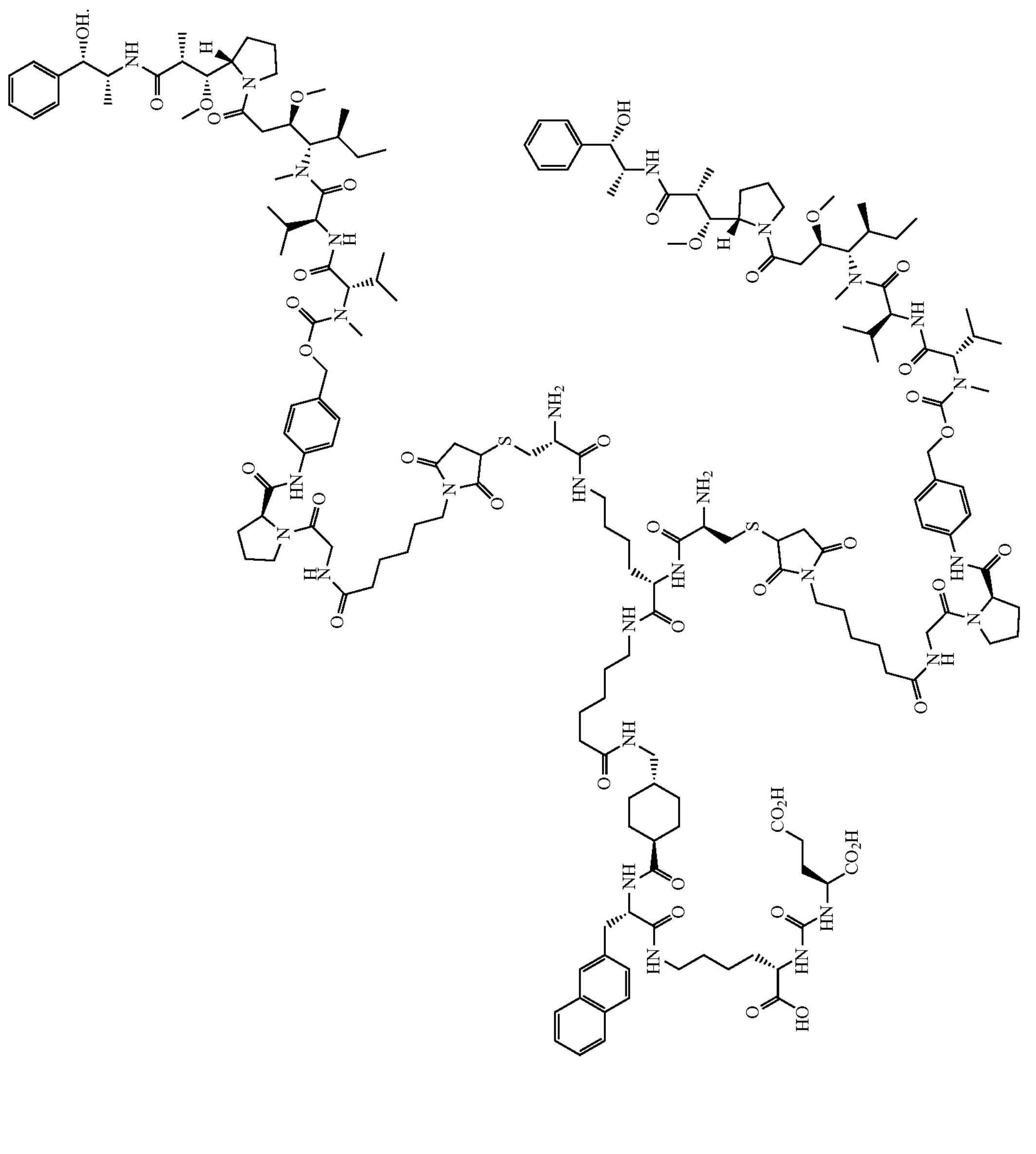
7

6. A pharmaceutical composition comprising the conjugate according to claim 1 and a pharmaceutically acceptable excipient.

7. A method of treatment of a subject suffering from a disease characterized by PSMA overexpression comprising administering a therapeutically effective amount of a conjugate of Formula I or a pharmaceutically acceptable salt thereof to a subject suffering from said disease wherein:

Formula I

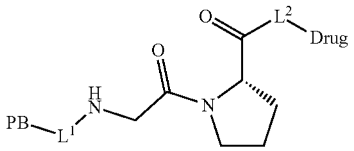

Gly-Pro

PB is a PSMA binding moiety of Formula II:

Formula II

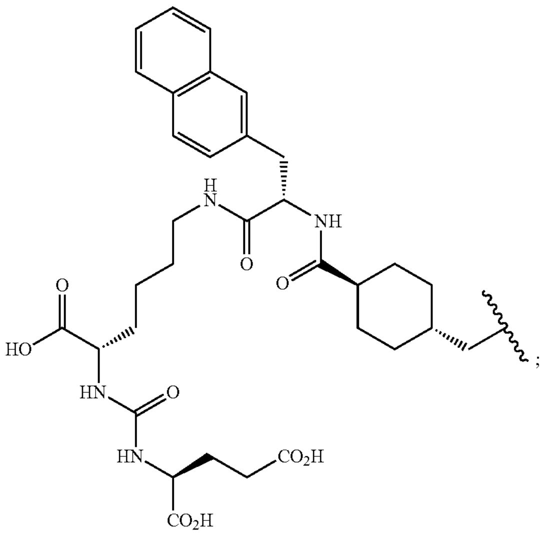

$L^1$ is a linker covalently attaching PB to Gly-Pro, said linker being $L^1$-4 or $L^1$-5:

$L^1$-4

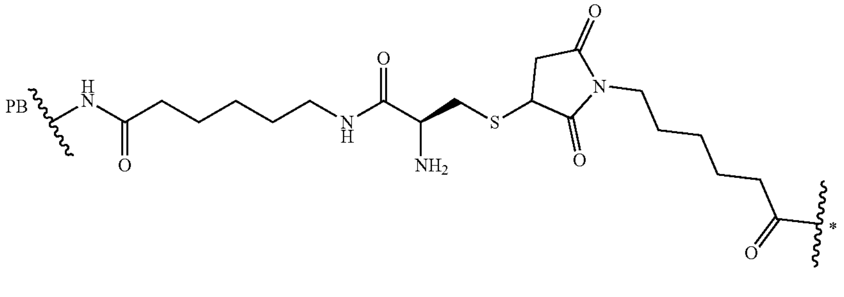

$L^1$-5

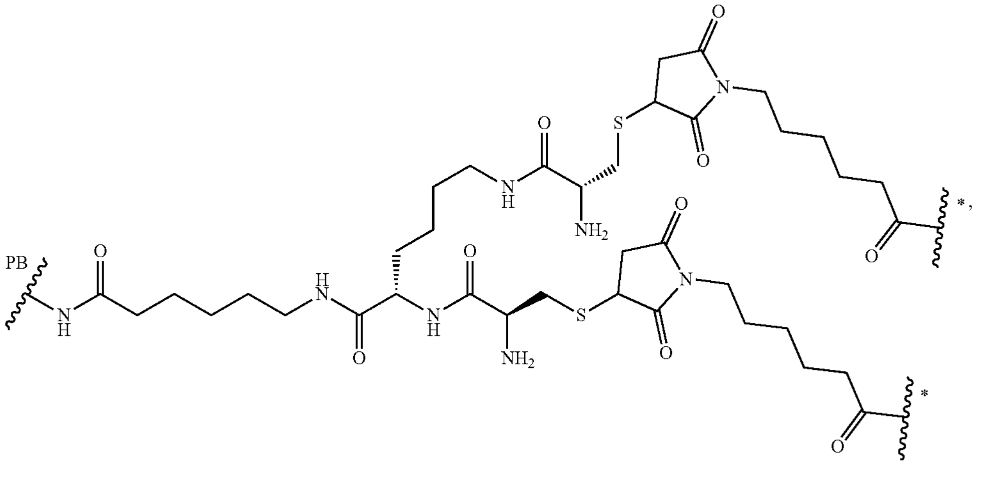

wherein * connects to N of the glycine in the Formula I; $L^2$ is a self-immolative linker with the structure:

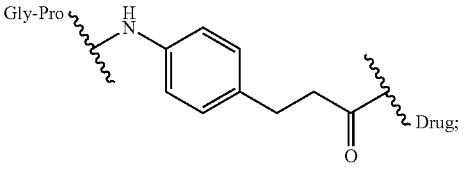 [SMILES: *Nc1ccc(CCC(*)=O)cc1]

and

Drug is a cytotoxic agent linked to Gly-Pro.

8. The method of treatment according to claim 7, wherein the disease characterized by PSMA overexpression is prostate cancer, including metastatic prostate cancer, hormone sensitive prostate cancer (HSPC), and castration resistant prostate cancer (CRPC).

9. The method of treatment according to claim 7, wherein said treatment comprises the separate, sequential or simultaneous administration of i) said conjugate of Formula I, or a pharmaceutically acceptable salt thereof, and ii) an immunocytokine comprising a sequence having IL2 activity.

* * * * *

SEQUENCE LISTING

```
Sequence total quantity: 16
SEQ ID NO: 1            moltype = AA  length = 5
FEATURE                 Location/Qualifiers
source                  1..5
                        mol_type = protein
                        organism = synthetic construct
SEQUENCE: 1
SFSMS                                                              5

SEQ ID NO: 2            moltype = AA  length = 17
FEATURE                 Location/Qualifiers
source                  1..17
                        mol_type = protein
                        organism = synthetic construct
SEQUENCE: 2
SISGSSGTTY YADSVKG                                                 17

SEQ ID NO: 3            moltype = AA  length = 7
FEATURE                 Location/Qualifiers
source                  1..7
                        mol_type = protein
                        organism = synthetic construct
SEQUENCE: 3
PFPYFDY                                                            7

SEQ ID NO: 4            moltype = AA  length = 12
FEATURE                 Location/Qualifiers
source                  1..12
                        mol_type = protein
                        organism = synthetic construct
SEQUENCE: 4
RASQSVSSSF LA                                                      12

SEQ ID NO: 5            moltype = AA  length = 7
FEATURE                 Location/Qualifiers
source                  1..7
                        mol_type = protein
                        organism = synthetic construct
SEQUENCE: 5
YASSRAT                                                            7

SEQ ID NO: 6            moltype = AA  length = 9
FEATURE                 Location/Qualifiers
source                  1..9
                        mol_type = protein
                        organism = synthetic construct
SEQUENCE: 6
QQTGRIPPT                                                          9

SEQ ID NO: 7            moltype = AA  length = 116
FEATURE                 Location/Qualifiers
source                  1..116
                        mol_type = protein
                        organism = synthetic construct
SEQUENCE: 7
EVQLLESGGG LVQPGGSLRL SCAASGFTFS SFSMSWVRQA PGKGLEWVSS ISGSSGTTYY  60
ADSVKGRFTI SRDNSKNTLY LQMNSLRAED TAVYYCAKPF PYFDYWGQGT LVTVSS      116
```

```
SEQ ID NO: 8           moltype = AA  length = 108
FEATURE                Location/Qualifiers
source                 1..108
                       mol_type = protein
                       organism = synthetic construct
SEQUENCE: 8
EIVLTQSPGT LSLSPGERAT LSCRASQSVS SSFLAWYQQK PGQAPRLLIY YASSRATGIP  60
DRFSGSGSGT DFTLTISRLE PEDFAVYYCQ QTGRIPPTFG QGTKVEIK              108

SEQ ID NO: 9           moltype = AA  length = 133
FEATURE                Location/Qualifiers
source                 1..133
                       mol_type = protein
                       organism = Homo sapiens
SEQUENCE: 9
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 10          moltype = AA  length = 386
FEATURE                Location/Qualifiers
source                 1..386
                       mol_type = protein
                       organism = synthetic construct
SEQUENCE: 10
EVQLLESGGG LVQPGGSLRL SCAASGFTFS SFSMSWVRQA PGKGLEWVSS ISGSSGTTYY  60
ADSVKGRFTI SRDNSKNTLY LQMNSLRAED TAVYYCAKPF PYFDYWGQGT LVTVSSGDGS  120
SGGSGGASEI VLTQSPGTLS LSPGERATLS CRASQSVSSS FLAWYQQKPG QAPRLLIYYA  180
SSRATGIPDR FSGSGSGTDF TLTISRLEPE DFAVYYCQQT GRIPPTFGQG TKVEIKEFSS  240
SSGSSSSGSS SSGAPTSSST KKTQLQLEHL LLDLQMILNG INNYKNPKLT RMLTFKFYMP  300
KKATELKHLQ CLEEELKPLE EVLNLAQSKN FHLRPRDLIS NINVIVLELK GSETTFMCEY  360
ADETATIVEF LNRWITFCQS IISTLT                                      386

SEQ ID NO: 11          moltype = AA  length = 12
FEATURE                Location/Qualifiers
source                 1..12
                       mol_type = protein
                       organism = synthetic construct
SEQUENCE: 11
GDGSSGGSGG AS                                                     12

SEQ ID NO: 12          moltype = AA  length = 5
FEATURE                Location/Qualifiers
source                 1..5
                       mol_type = protein
                       organism = synthetic construct
SEQUENCE: 12
GSSGG                                                             5

SEQ ID NO: 13          moltype = AA  length = 5
FEATURE                Location/Qualifiers
source                 1..5
                       mol_type = protein
                       organism = synthetic construct
SEQUENCE: 13
GGSGG                                                             5

SEQ ID NO: 14          moltype = AA  length = 15
FEATURE                Location/Qualifiers
source                 1..15
                       mol_type = protein
                       organism = synthetic construct
SEQUENCE: 14
GGGGSGGGGS GGGGS                                                  15

SEQ ID NO: 15          moltype = AA  length = 17
FEATURE                Location/Qualifiers
source                 1..17
                       mol_type = protein
                       organism = synthetic construct
SEQUENCE: 15
EFSSSSGSSS SGSSSSG                                                17

SEQ ID NO: 16          moltype = AA  length = 236
FEATURE                Location/Qualifiers
source                 1..236
                       mol_type = protein
                       organism = synthetic construct
```

-continued

| | | | | | | |
|---|---|---|---|---|---|---|
| SEQUENCE: 16 | | | | | | |
| EVQLLESGGG | LVQPGGSLRL | SCAASGFTFS | SFSMSWVRQA | PGKGLEWVSS | ISGSSGTTYY | 60 |
| ADSVKGRFTI | SRDNSKNTLY | LQMNSLRAED | TAVYYCAKPF | PYFDYWGQGT | LVTVSSGDGS | 120 |
| SGGSGGASEI | VLTQSPGTLS | LSPGERATLS | CRASQSVSSS | FLAWYQQKPG | QAPRLLIYYA | 180 |
| SSRATGIPDR | FSGSGSGTDF | TLTISRLEPE | DFAVYYCQQT | GRIPPTFGQG | TKVEIK | 236 |